United States Patent
Shukla et al.

(10) Patent No.: US 11,725,237 B2
(45) Date of Patent: Aug. 15, 2023

(54) POLYMORPHIC GENE TYPING AND SOMATIC CHANGE DETECTION USING SEQUENCING DATA

(71) Applicants: The Broad Institute Inc., Cambridge, MA (US); Dana-Farber Cancer Institute, Inc., Boston, MA (US); The General Hospital Corporation, Boston, MA (US)

(72) Inventors: Sachet Ashok Shukla, Newton, MA (US); Catherine Ju-Ying Wu, Brookline, MA (US); Gad Getz, Belmont, MA (US)

(73) Assignees: The Broad Institute Inc., Cambridge, MA (US); Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 722 days.

(21) Appl. No.: 15/037,394

(22) PCT Filed: Dec. 5, 2014

(86) PCT No.: PCT/US2014/068746
§ 371 (c)(1),
(2) Date: May 18, 2016

(87) PCT Pub. No.: WO2015/085147
PCT Pub. Date: Jun. 11, 2015

(65) Prior Publication Data
US 2016/0298185 A1   Oct. 13, 2016

Related U.S. Application Data

(60) Provisional application No. 61/912,305, filed on Dec. 5, 2013.

(51) Int. Cl.
*C12Q 1/6874* (2018.01)
*G16B 20/00* (2019.01)
(Continued)

(52) U.S. Cl.
CPC ......... *C12Q 1/6874* (2013.01); *C12Q 1/6827* (2013.01); *C12Q 1/6881* (2013.01);
(Continued)

(58) Field of Classification Search
None
See application file for complete search history.

(56) References Cited

U.S. PATENT DOCUMENTS 3,854,480 A   12/1974  Zaffaroni
3,870,790 A    3/1975  Lowey et al.
(Continued)

FOREIGN PATENT DOCUMENTS

CN   103180730 A     6/2013
EP    1486567 A1    12/2004
(Continued)

OTHER PUBLICATIONS

International Search Report dated Mar. 23, 2015, which issued during prosecution of International Application No. PCT/US2014/068746.
(Continued)

*Primary Examiner* — Lori A. Clow
(74) *Attorney, Agent, or Firm* — Foley Hoag LLP; DeAnn F. Smith; Thi K. Dio

(57) ABSTRACT

A system and method for determining the exact pair of alleles corresponding to polymorphic genes from sequencing data and for using the polymorphic gene information in formulating an immunogenic composition. Reads from a sequencing data set mapping to the target polymorphic genes in a canonical reference genome sequence, and reads mapping within a defined threshold of the target gene sequence locations are extracted from the sequencing data set. Additionally, all reads from the set data set are matched against a probe reference set, and those reads that match with a high degree of similarity are extracted. Either one, or a union of both these sets of extracted reads are included in a final extracted set for further analysis. Ethnicity of the individual may be inferred based on the available sequencing data which may then serve as a basis for assigning prior probabilities to the allele variants. The extracted reads are aligned to a gene reference set of all known allele variants. The allele variant that maximizes a first posterior probability or posterior probability derived score is selected as the first allele variant. A second posterior probability or posterior probability derived score is calculated for reads that map to one or more other allele variants and the first allele variant using a weighting factor. The allele that maximizes the second posterior probability or posterior probability score is selected as the second allele variant.

A system and method for identifying somatic changes in polymorphic loci using WES data. The exact pair of alleles corresponding to the polymorphic gene are determined as described using a normal or germline sample from an individual. A tumor or otherwise diseased sample is also retrieved from the individual and the corresponding WES data is generated. Reads corresponding to the polymorphic gene are extracted as described in the paragraph above. These reads are then aligned to the inferred pair of allele sequences. The alignment of the germline or normal reads to the inferred pair of alleles, along with the alignment of the tumor or diseased reads to the inferred pair of alleles are simultaneously used as inputs to somatic change detection algorithms to identify somatic changes with greater precision and sensitivity.

4 Claims, 18 Drawing Sheets

(51) Int. Cl.
*G16B 30/00* (2019.01)
*C12Q 1/6827* (2018.01)
*C12Q 1/6886* (2018.01)
*G16B 30/10* (2019.01)
*G16B 20/20* (2019.01)
*G16B 20/40* (2019.01)
*C12Q 1/6881* (2018.01)

(52) U.S. Cl.
CPC .......... *C12Q 1/6886* (2013.01); *G16B 20/00* (2019.02); *G16B 20/20* (2019.02); *G16B 20/40* (2019.02); *G16B 30/00* (2019.02); *G16B 30/10* (2019.02); *C12Q 2600/156* (2013.01)

(56) References Cited

U.S. PATENT DOCUMENTS

| | | |
|---|---|---|
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,554,101 A | 11/1985 | Hopp |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |

(56) References Cited

U.S. PATENT DOCUMENTS

| | | |
|---|---|---|
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,572,821 B2 | 8/2009 | Sun et al. |
| 7,608,279 B2 | 10/2009 | Parisot et al. |
| 7,628,980 B2 | 12/2009 | Suter et al. |
| 7,705,120 B2 | 4/2010 | Lillie et al. |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,557,779 B2 | 10/2013 | Sugiyama |
| 8,648,104 B2 | 2/2014 | Du et al. |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,556,237 B2 | 1/2017 | Schmaljohn et al. |
| 9,909,159 B2 | 3/2018 | Marras et al. |
| 9,962,453 B2 | 5/2018 | Georges |
| 10,202,640 B2 | 2/2019 | Davis et al. |
| 10,426,824 B1 | 10/2019 | Hacohen et al. |
| 10,801,070 B2 | 10/2020 | Clement et al. |
| 10,835,585 B2 | 11/2020 | Fritsch et al. |
| 10,975,442 B2 | 4/2021 | Hacohen et al. |
| 10,993,997 B2 | 5/2021 | Hacohen et al. |
| 11,452,768 B2 | 9/2022 | Hacohen et al. |
| 2003/0104008 A1 | 6/2003 | Loosmore et al. |
| 2004/0013648 A1 | 1/2004 | Kingsman et al. |
| 2004/0018971 A1 | 1/2004 | Fikes et al. |
| 2004/0053304 A1 | 3/2004 | Markowitz |
| 2006/0008468 A1 | 1/2006 | Chiang et al. |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1 | 4/2007 | Mintz et al. |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons et al. |
| 2008/0014589 A1 | 1/2008 | Link et al. |
| 2008/0071706 A1 | 3/2008 | Honda et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0028888 A1 | 1/2009 | Bergeron et al. |
| 2009/0055944 A1 | 2/2009 | Korman et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2009/0304711 A1 | 12/2009 | Pardoll et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0203531 A1 | 8/2010 | Sarkaria et al. |
| 2010/0210529 A1 | 8/2010 | Van Der Burg et al. |
| 2010/0282617 A1 | 11/2010 | Rothberg et al. |
| 2010/0286057 A1 | 11/2010 | Walensky et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0223149 A1 | 9/2011 | Nash et al. |
| 2011/0257890 A1 | 10/2011 | Weinschenk et al. |
| 2011/0293571 A1 | 12/2011 | Widdowson et al. |
| 2011/0293637 A1 | 12/2011 | Hacohen et al. |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Palfi et al. |
| 2013/0071414 A1 | 3/2013 | Dotti et al. |
| 2013/0210014 A1 | 8/2013 | Sharman |
| 2013/0295110 A1 | 11/2013 | Binder et al. |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 | 10/2014 | Robins |
| 2015/0079119 A1 | 3/2015 | Johnston |
| 2015/0125463 A1 | 5/2015 | Cogswell et al. |
| 2015/0140041 A1 | 5/2015 | Vitiello |
| 2015/0224182 A1 | 8/2015 | Hunt et al. |
| 2015/0278441 A1 | 10/2015 | Min et al. |
| 2016/0008447 A1 | 1/2016 | Hacohen et al. |
| 2016/0101170 A1 | 4/2016 | Hacohen et al. |
| 2016/0130641 A1 | 5/2016 | Wang et al. |
| 2016/0213771 A1 | 7/2016 | Sampson et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0022251 A1 | 1/2017 | Rammensee et al. |
| 2017/0067090 A1 | 3/2017 | Zhang et al. |
| 2017/0160269 A1 | 6/2017 | Linnemann et al. |
| 2017/0199961 A1 | 7/2017 | Yelensky et al. |
| 2017/0233821 A1 | 8/2017 | Lianidou et al. |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1 | 4/2019 | Benz et al. |
| 2019/0376147 A1 | 12/2019 | Fritsch |
| 2020/0016251 A1 | 1/2020 | Hacohen et al. |
| 2020/0069783 A1 | 3/2020 | Hacohen et al. |
| 2020/0101147 A1 | 4/2020 | Zeng |
| 2020/0330571 A1 | 10/2020 | Fritsch et al. |
| 2020/0368337 A1 | 11/2020 | Fritsch et al. |
| 2020/0407804 A1 | 12/2020 | Clement et al. |
| 2021/0220455 A1 | 7/2021 | Hacohen et al. |
| 2021/0262039 A1 | 8/2021 | Hacohen et al. |
| 2021/0379168 A1 | 12/2021 | Hacohen et al. |

FOREIGN PATENT DOCUMENTS

| | | |
|---|---|---|
| EP | 1680681 B1 | 11/2011 |
| EP | 2390363 A1 | 11/2011 |
| EP | 2569633 A2 | 3/2013 |

(56) References Cited

FOREIGN PATENT DOCUMENTS

| | | |
|---|---|---|
| EP | 2574346 A1 | 4/2013 |
| FR | 2650840 A1 | 2/1991 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532664 A | 9/2009 |
| JP | 2009532350 A | 9/2009 |
| JP | 2010533184 A | 10/2010 |
| JP | 2012/522500 A | 9/2012 |
| JP | 2013/530943 A | 8/2013 |
| WO | WO-9102087 A1 | 2/1991 |
| WO | WO-9106309 A1 | 5/1991 |
| WO | WO-92/15322 A1 | 9/1992 |
| WO | WO-92/15672 A1 | 9/1992 |
| WO | WO-9215712 A1 | 9/1992 |
| WO | WO-9324640 A2 | 12/1993 |
| WO | WO-95/27780 A1 | 10/1995 |
| WO | WO-95/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003/020763 A2 | 3/2003 |
| WO | WO-2003/057171 A2 | 7/2003 |
| WO | WO-03/086459 A1 | 10/2003 |
| WO | WO-03/106692 A2 | 12/2003 |
| WO | WO-2004/002627 A2 | 1/2004 |
| WO | WO-2004/033685 A1 | 4/2004 |
| WO | WO-2004026897 A1 | 4/2004 |
| WO | WO-2004030615 A2 | 4/2004 |
| WO | WO-2004/044004 A2 | 5/2004 |
| WO | WO-2004/058801 A2 | 7/2004 |
| WO | WO-2004/074322 A1 | 9/2004 |
| WO | WO-2004/091763 A2 | 10/2004 |
| WO | WO-2005/021151 A1 | 3/2005 |
| WO | WO-2005087261 A2 | 9/2005 |
| WO | WO-2005/113595 A2 | 12/2005 |
| WO | WO-2005/114215 A2 | 12/2005 |
| WO | WO-2006/000830 A2 | 1/2006 |
| WO | WO-2006/040551 A2 | 4/2006 |
| WO | WO-2006/040554 A1 | 4/2006 |
| WO | WO-2006/096571 A2 | 9/2006 |
| WO | WO-2006/121168 A1 | 11/2006 |
| WO | WO-2006/125962 A2 | 11/2006 |
| WO | WO-2007015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |
| WO | WO-2007/133710 A2 | 11/2007 |
| WO | WO-2008/011344 A2 | 1/2008 |
| WO | WO-2008/038002 A2 | 4/2008 |
| WO | WO-2008/039818 A2 | 4/2008 |
| WO | WO-2008/063227 A2 | 5/2008 |
| WO | WO-2008/096831 A1 | 8/2008 |
| WO | WO-2008/109075 A2 | 9/2008 |
| WO | WO-2009/014708 A2 | 1/2009 |
| WO | WO-2009/025117 A1 | 2/2009 |
| WO | WO-2009032477 A2 | 3/2009 |
| WO | WO-2009043520 A1 | 4/2009 |
| WO | WO-2009/126306 A2 | 10/2009 |
| WO | WO-2010033949 A1 | 3/2010 |
| WO | WO-2010/045345 A2 | 4/2010 |
| WO | WO-2010/093784 A2 | 8/2010 |
| WO | WO-2011/051489 A2 | 5/2011 |
| WO | WO-2011/079176 A2 | 6/2011 |
| WO | WO-2011/143656 A2 | 11/2011 |
| WO | WO-2011/146862 A1 | 11/2011 |
| WO | WO-2011134944 A2 | 11/2011 |
| WO | WO-2012027379 A2 | 3/2012 |
| WO | WO-2012/079000 A1 | 6/2012 |
| WO | WO-2012/095639 A2 | 7/2012 |
| WO | WO-2012/101112 A1 | 8/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013/036201 A1 | 3/2013 |
| WO | WO-2013/039889 A1 | 3/2013 |
| WO | WO-2013/040371 A2 | 3/2013 |
| WO | WO-2013/086464 A1 | 6/2013 |
| WO | WO-2013/123031 A2 | 8/2013 |
| WO | WO-2013133405 A1 | 9/2013 |
| WO | WO-2013/166321 A1 | 11/2013 |
| WO | WO-2013/173223 A1 | 11/2013 |
| WO | WO-2013/176915 A1 | 11/2013 |
| WO | WO-2013164754 A2 | 11/2013 |
| WO | WO-2014/009535 A2 | 1/2014 |
| WO | WO-2014/011987 A1 | 1/2014 |
| WO | WO-2014/012051 A1 | 1/2014 |
| WO | WO-2014/018863 A1 | 1/2014 |
| WO | WO-2014/047561 A1 | 3/2014 |
| WO | WO-2014/056986 A1 | 4/2014 |
| WO | WO-2014/059173 A2 | 4/2014 |
| WO | WO-2014/083173 A1 | 6/2014 |
| WO | WO-2014/085802 A1 | 6/2014 |
| WO | WO-2014/133567 A1 | 9/2014 |
| WO | WO-2014/133568 A1 | 9/2014 |
| WO | WO-2014/134165 A1 | 9/2014 |
| WO | WO-2014/150924 A2 | 9/2014 |
| WO | 2014168874 | 10/2014 |
| WO | WO-2014/172606 A1 | 10/2014 |
| WO | WO-2014/183649 A1 | 11/2014 |
| WO | WO-2014/184744 A1 | 11/2014 |
| WO | WO-2014/191128 A1 | 12/2014 |
| WO | WO-2014/197369 A1 | 12/2014 |
| WO | WO-2015/085233 A1 | 6/2015 |
| WO | WO-2015/094995 A2 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/164833 A1 | 10/2016 |
| WO | WO-2016/187508 A2 | 11/2016 |
| WO | WO-2016/201049 A2 | 12/2016 |
| WO | WO-2017/173321 A1 | 10/2017 |
| WO | WO-2017/184590 A1 | 10/2017 |
| WO | WO-2018/140391 A1 | 8/2018 |

OTHER PUBLICATIONS

Liu, et al. "ATHLATES: accurate typing of human leukocyte antigen through exome sequencing" Nucleic Acids Research, 2013, 41(14):e142, doi:10.1093/nar/gkt481.

Erlich, et al. "Next generation sequencing for HLA typing of Class I loci", BMC Genomics, 2011, 12:42, http://www.biomedcentral.com/1471-2164/12/42.

Shukla, et al. "Topics in cancer genomics" 2014, http://search.proquest.com/docview/1558874754.

Rooney, et al. "Molecular and Genetic Properties of Tumors Associated with Local Immune Cytolytic Activity" Cell, 2015, 160:48-61.

International Preliminary Report and Written Opinion of the International Searching Authority dated Jun. 7, 2016, which issued during prosecution of International Application No. PCT/US2014/068746.

U.S. Appl. No. 16/094,786, filed Oct. 18, 2018, 2019-0346442, Published.

U.S. Appl. No. 13/108,610, filed May 16, 2011, 2011-0293637, U.S. Pat. No. 9,115,402, Granted.

U.S. Appl. No. 14/794,449 filed Jul. 8, 2015, 2016-00008447, Abandoned.

U.S. Appl. No. 15/187,174, filed Jun. 20, 2016, 2016-033182, Abandoned.

U.S. Appl. No. 15/800,732, filed Nov. 1, 2017, 2018-0055922, Published.

U.S. Appl. No. 16/181,098, filed Nov. 5, 2018, 2019-0060432, Published.

(56) References Cited

OTHER PUBLICATIONS

U.S. Appl. No. 16/188,737, filed Nov. 13, 2018, 2016-0101170, U.S. Pat. No. 10,426,824, Granted.
U.S. Appl. No. 16/381,791, filed Apr. 11, 2019, 2020-0069783, Published.
U.S. Appl. No. 16/528,195, filed Jul. 31, 2019, 2020-0016251, Published.
U.S. Appl. No. 14/877,125, filed Oct. 7, 2015, 2016-0101170, Pending.
U.S. Appl. No. 17/089,408, filed Nov. 4, 2020, Pending.
U.S. Appl. No. 15/102,129, filed Jun. 6, 2016, 2016-0310584, Abandoned.
U.S. Appl. No. 16/813,371, filed Ma. 9, 2020, 2020-0330571, Published.
U.S. Appl. No. 15/038,504, filed May 23, 2016, 2016-0326593, U.S. Pat. No. 10,801,070, Granted.
U.S. Appl. No. 17/017,045, filed Sep. 10, 2020, 2020-0407804, Published.
U.S. Appl. No. 15/105,961, filed Jun. 17, 2016, 2016-0339090, Published.
U.S. Appl. No. 15/537,785, filed Jun. 19, 2017 2018-0000913, Allowed.
U.S. Appl. No. 17/217,864, filed Mar. 30, 2021, Pending.
U.S. Appl. No. 15/537,839, filed Jun. 19, 2017, 2019-0127803, U.S. Pat. No. 10,975,442, Granted.
U.S. Appl. No. 17/179,956, filed Feb. 19, 2021, Pending.
U.S. Appl. No. 15/575,328, filed Nov. 17, 2017, 2018-0153975, U.S. Pat. No. 10,835,585, Granted.
U.S. Appl. No. 16/859,252, filed Apr. 27, 2020, 2020-0368337, Published.
U.S. Appl. No. 15/513,127, filed Mar. 21, 2017, 2017-0298441, Published.
U.S. Appl. No. 15/735,566, filed Dec. 11, 2017, 2019-0060428, Published.
U.S. Appl. No. 16/480,535, filed Jul. 24, 2019, 2019-0376147, Published.
EP Application No. 11781409.5 (opposition therein), May 16, 2011, 2569633, 2569633, Granted-opposition pending.
EP Application No. 15198284.0, May 16, 2011, 3023788, 3023788, Granted-opposition pending.
"CT-011 and p53 Genetic Vaccine for Advance Solid Tumor," National Library of Medicine, updated:Jun. 30, 2011, XP002738554, https://clinicaltrials.gov/archive/NCT01386502/2011_06_30, Clinical Trials Identifier NCT01386502.
"Monoclonal Antibody Therapy and Vaccine Therapy in Treating Patients with Stage IV Melanoma That Has Been Removed By Surgery," National Library of Medicine, 2010, XP002738553, https:clinicaltrials.gov/archive/NCT01176474/2010_08_05.
"Neon Therapeutics' Personal Neoantigen Vaccine Study Demonstrates Prolonged Progression-Free Survival in Advanced or Metastatic Melanoma, Non-Small Cell Lung and Bladder Cancers," published by Globe Newswire on Jul. 15, 2019 ("Neon Press Release 2019").
"Single-cell sequencing: A brief overview of howto derive a genome or transcriptome from a single cell," Nature Methods, 18(11) (2014).
Acknowledgment of Receipt dated Jun. 28, 2017 for Response to Notices of Opposition of EP2569633.
Albert et al., "Direct Selection of Human Genomic Loci by Microarray Hybridization," Nat Methods, 4(11): 903-905 (2007).
Allocca et al., "Novel adeno-associated virus serotypes efficiently transduce murine Photoreceptors." Journal of Virology, 81(20): 11372-11380 (2007).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Anderson et al., "Next Generation DNA Sequencing and the Future of Genomic Medicine," Genes, 1: 38-69 (2010).
Andreatta et al., "Gapped sequence alignment using artificial neural networks: application to the MHC class I system," Bioinformatics 32(4):511-517 (2016).
Annunziata et al., "Frequent Engagement of the Classical and Alternative NF-KB Pathways by Diverse Genetic Abnormalities in Multiple Myeloma," Cancer Cell, 12(2):115-130 (2007).
Applicant's Authorization and Release Form of the Massachusetts General Hospital, Aug. 12, 2008; and Supplemental Release to Applicant of the Partners Healthcare System, Aug. 13, 2008.
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachireddy et al., "Reversal of in situ T cell exhaustion during effective human anti-leukemia responses to donor lymphocyte infusion," Blood, 123(9):1412-1421 (2013).
Backed et al., "Immunoinformatics and epitope prediction in the age of genomic medicine," Genome Medicine, 7:119 (2015).
Balakrishnan et al, "Novel Somatic and Germline Mutations in Cancer Candidate Genes in Glioblastoma, Melanoma, and Pancreatic Carcinoma," Cancer Res, 67: 3545-3550 (2007).
Baskar et al., "Autologous Lymphoma Vaccines Induce Human T Cell Responses Against Multiple, Unique Epitopes," J Clin Invest, 113:1498-1510 (2004).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Baurain et al., "High Frequency of Autologous Anti-Melanoma CTL Directed Against an Antigen Generated by a Point Mutation in a New Helicase Gene," J Immunol, 164: 6057-6066 (2000).
Beck et al., "Enterocolitis in Patients With Cancer After Antibody Blockade of Cytotoxicity TLymphocyte-Associated Antigen 4," J Clin Oncol, 24(15): 2283-2289 (2006).
Bediaga et al., "DNA methylation epigenotypes in breast cancer molecular subtypes," Breast Cancer Research, 12:R77 (2010).
Behrends et al., "Network organization of the human autophagy system," Nature, 466(7302):68-76 (2010).
Bellucci et al., "Complete Response to Donor Lymphocyte Infusion in Multiple Myeloma is Associated with Antibody Responses to Highly Expressed Antigens," Blood, 103: 656-663 (2004).
Bentley et al., "Accurate Whole Human Genome Sequencing using Reversible Terminator Chemistry," Nature, 456(7218): 53-59 (2008).
Berg et al., "Detection of artifacts and peptide modifications in liquid chromatography/mass spectrometry data using two-dimensional signal intensity map data visualization," Rapid Common Mass Spectrom, 20(10):1558-1562 (2006).
Berger et al., "Melanoma genome sequencing reveals frequent PREX2 mutations," Nature, 485(7399):502 (2012).
Bettelli et al., "TH-17 cells in the circle of immunity and autoimmunity," Nat Immunol, 8:345-350 (2007).
Boen et al., "Identification of T Cell Ligands in a Library of Peptides Covalently Attached to HLA-DR4," J Immunol, 165:2040-2047 (2000).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Boisguerin et al., "Translation of genomis-guided RNA-based personalised cancer vaccaines: towards the bedside," British J Cancer, 111:1469-1475 (2014).
Boon et al., "Human T Cell Responses Against Melanoma," Annu Rev Immunol, 24: 175-208 (2006).
Boon, "Toward a Genetic Analysis of Tumor Rejection Antigens," Adv Cancer Res, 58:177-210 (1992).

(56) References Cited

OTHER PUBLICATIONS

Bourdetsky et al., The nature and extent of contributions by defective ribosome products to the HLA peptidome, Pnas, III, E1591-E1599 (2014).
Bowerman et al., "Engineering the binding properties of the T cell receptor:peptide:MHC ternary complex that governs T cell activity," Mol Immunol, 46(15):3000-3008 (2009).
Brandie et al., "A Mutated HLA-A2 Molecule Recognized by Autologous Cytotoxic T Lymphocytes on a Human Renal Cell Carcinoma," J Exp Med, 183: 2501-2508 (1996).
Bremel et al., "An integrated approach to epitope analysis I: Dimensional reduction, visualization and prediction of MHC binding using amino acid principal components and regression approaches," Immunome Res, 6:7 (2010).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brown et al., "Neo-antigens predicted by tumor genome meta-analysis correlate with increased patient survival," Genome Res, 24(5):743-750 (2014).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Böhmet et al., DNA vector constructs that prime hepatitis B surface antigen-specific cytotoxic T lymphocyte and antibody responses in mice after intramuscular injection. Journal of immunological methods 193(1): 29-40 (1996).
Cai et al., "Mutated BCR-ABL Generates Immunogenic T-Cell Epitopes in CML Patients," Clinical Cancer Research, 18(20):5761-5772 (2012).
Cai et al., "Peptides Derived From Mutated BCR-ABL Elicit T Cell Immunity In CML Patients," BLOOD, 116(21): 388-388 (2010).
Cancer Genome Atlas Network, "Comprehensive molecular characterization of human colon and rectal cancer," Nature, 487:330-337 (2012).
Cancer Genome Atlas Network, "Comprehensive molecular portraits of human breast tumours," Nature, 490:61-70 (2012).
Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Genomic and epigenomic landscapes of adult de novo acute myeloid leukemia," New England Journal of Medicine, 368(22):2059-2074 (2013).
Cancer Genome Atlas Research Network, "Integrated genomic analyses of ovarian carcinoma," Nature, 474: 609-615 (2011).
Cardarella et al., "Clinical, Pathologic, and Biologic Features Associated with BRAF Mutations in Non-Small Cell Lung Cancer," Clin Cancer Res, 19(16):4532-4540 (2013).
Caron et al., "Analysis of MHC immunopeptidomes using mass spectrometry," Mol Cell Proteomics (2015), doi: 10.1074/mcp.OI 15.052431.
Carpten et al., "A transforming mutation in the pleckstrin homology domain of AKT1 in cancer," Nature, 448(26):439-444 (2004).
Carreno et al., "A dendritic cell vaccine increases the breadth and diversity of melanoma neoantigen-specific T cells," Science, 348(6239):803-808 (2015).
Carter et al., "Identification and validation of cell surface antigens for antibody targeting in oncology," Endocrine—Related Cancer, 11:659-687 (2004).
Certified Priority Document for U.S. Appl. No. 61/334,866, filed May 14, 2010.
Chang et al., "Peptide length-based prediction of peptide-MHC class II binding," Bioinformatics, 22(22): 2761-2767 (2006).

Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
Chatila, "The Regulatory T Cell Transcriptosome: E Pluribus Unum," Immunity, 27(5):693-695 (2007).
Chen et al., Molecular Pharmaceutics, 3:109-111 (2010).
Chianese-Bullock et al., "Multi-peptide vaccines vialed as peptide mixtures can be stable reagents for use in peptide-based immune therapies," Vaccine, 27(11):1764-1770 (2009).
Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Chinese Office Action dated Jun. 12, 2017 in corresponding CN Application No. 2014800322910.
Chowell et al., "TCR contact residue hydrophobicity is a hallmark of immunogenic CD8(+) T cell epitopes," PNAS, 112:E1754-E1762 (2015).
Christianson et al., "Defining human ERAD networks through an integrative mapping strategy," Nat Cell Biol, 14:93-105 (2012).
Ciofani et al., "A Validated Regulatory Network for Th17 Cell Specification," Cell, 151(2):289-303 (2012).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
Coffman et al., "Vaccine Adjuvants: Putting Innate Immunity to Work," Immunity 33:492-503 (2010).
Consolidated Table of Documents filed in Opposition to date in Response to Notices of Opposition of EP2569633 dated Jun. 28, 2017.
Dai et al., "Prediction of soluble heterologous protein expression levels in *Escherichia coli* from sequence-based features and its potential in biopharmaceutical process development," Pharmaceutical Bioprocessing, 2(3): 253-266 (2014).
De Plaen et al., "Immunogenic (tum-) Variants of Mouse Tumor P815: Cloning of the Gene of Tum- Antigen P91A and Identification of the Tum- Mutation," PNAS, 85: 2274-2278 (1988).
Declaration by Professor John Haanen, M.D., Ph.D. on Mar. 8, 2019.
Declaration by Stephen Johnston filed during the prosecution of granted U.S. Pat. No. 8,796,414 Nov. 20, 2013.
Declaration of Dr Nir Hacohen on Feb. 16, 2014.
Declaration of Dr. John C. Castle executed on Nov. 9, 2016.
DeKosky et al., "High-throughput sequencing of the paired human immunoglobulin heavy and light chain repertoire," Nature Biotech 166-170 (2013).
Dengjel et al., "Glycan side chains on naturally presented MHC class II ligands," J. Mass Spectrom, 40:100-104 (2005).
Dermer et al., "Another Anniversary for the War on Cancer," Biotech, 12:320 (1994).
Di Nicolantonio et al., "Wild-Type Is Required for Response to Panitumumab or Cetuximab in Metastatic Colorectal Cancer," Journal of Clinical Oncology, 26(35):5705-5712 (2008).
Ding et al., "Genome remodelling in a basal-like breast cancer metastasis and xenograft," Nature, 464:999-1005 (2010).
Donkena et al., "Oxidative Stress and DNA Methylation in Prostate Cancer," Obstetrics and Gynecology International, 2010(Article ID 302051):14 pages (2010).
Dressman et al., "Gene expression profiles of multiple breast cancer phenotypes and response to neoadjuvant chemotherapy," Clin Cancer Res, 12(3):819-826 (2006).
Du et al., "The Significance and Therapeutic Potential of GATA3 Expression and Mutation in Breast Cancer: A Systematic Review," Med Res Rev, 35(6):1300-1315 (2015).
Dudley et al., "Cancer Regression and Autoimmunity in Patients After Clonal Repopulation with Antitumor Lymphocytes," Science, 298: 850-854 (2002).
Dössinger et al., "MHC multimer-guided and cell culture-independent isolation of functional T cell receptors from single cells facilitates TCR identification for immunotherapy," PloS one, 8(4):e61384 (2013).

(56) References Cited

OTHER PUBLICATIONS

Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Engelhard, "Structure of peptides associated with MHC class I molecules," Curr Opin Immunol, 6(1):13-23 (1994).
Estep et al., "Mutation Analysis of BRAF, MEK1 and MEK2 in 15 Ovarian Cancer Cell Lines: Implications for Therapy," Plos One, 12:e1279 (2007).
Extended European Search Report dated Apr. 11, 2016, which issued during prosecution of EP Application No. 15198284.0.
Extended European Search Report for EP Application No. 19219395.1 dated Jul. 23, 2020.
Extended European Search Report for EP Application No. EP 20179960 dated Nov. 9, 2020.
Extended European Search Report received for EP patent application No. EP11781409, dated Apr. 10, 2014.
Extended Search Report in Corresponding European Application No. 11781409.5, dated Apr. 14, 2014.
Extracts from the USPTO patent register.
Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Ezzell, "Cancer 'Vaccines': An idea whose time has come?," J NIH Res, 7:46 (1995).
Filatreau et al., "Technische Universitat Berlin, Fakultat III—Prozesswissenschaften Direct comparasion of T cell receptor avidity of auto-antigen specific conventional and regulatory T cells," Abstract, 1-6.
Final Office Action for U.S. Appl. No. 15/735,566, "Formulations for Neoplasia Vaccines and Methods of Preparing Thereof," dated Feb. 3, 2021.
Final Office Action for U.S. Appl. No. 15/800,732, "Compositions and Methods of Identifying Tumor Specific Neoantigens," dated Dec. 17, 2020.
Final Office Action for U.S. Appl. No. 16/813,371, "Formulations for Neoplasia Vaccines," dated Oct. 13, 2020.
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504 , "Compositions and Methods for Diagnosing, Evaluating and Treating Cancer By Means of the DNA Methyl," dated Apr. 30, 2018.
Final Rejection for U.S. Appl. No. 15/038,504 , "Compositions and Methods for Diagnosing, Evaluating and Treating Cancer By Means of the DNA Methyl," dated Dec. 21, 2018.
Final Rejection for U.S. Appl. No. 15/102,129, "Formulations for Neoplasia Vaccines," dated Aug. 15, 2019.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Aug. 23, 2019.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 15/537,785, "Methods for Profiling the T Cell Repertoire," dated Jul. 18, 2019.
Final Rejection for U.S. Appl. No. 15/537,839, "Molecular Biomarkers for Cancer Immunotherapy," dated May 1, 2020.
Final Rejection for U.S. Appl. No. 15/575,328," Shared Neoantigens," dated Oct. 23, 2019.
Final Rejection for U.S. Appl. No. 16/181,098, "Compositions and Methods of Identifying Tumor Specific Neoantigens," dated Jun. 17, 2019.
Fritsch et al., "HLA-Binding Properties of Tumor Neoepitopes in Humans," Cancer Immunol Res, 2(6):522-529 (2014).
Fritsch et al., "Personal Neoantigen Cancer Vaccines: A Road Not Fully Paved," Cancer Immunology Research, 8: 1465-9 (2020).
Fritsch et al., "Personal neoantigen cancer vaccines: The momentum builds," Oncoimmunology, 3(6):e29311 (2014).
Fruci et al., "Altered expression of endoplasmic reticulum aminopeptidases ERAPI and ERAP2 in transformed non-lymphoid human tissues," J Cell Physiol, 216(3):742-749 (2008).
Furman et al., "Ibrutinib resistance in chronic lymphocytic leukemia," New Engl J Med, 370(24):2352 (2014).
Fusaro et al., "Prediction of high-responding peptides for targeted protein assays by mass spectrometry" Nat Biotechnol, 27(2):190-198 (2009).
Ganesan et al., "Tumor-Infiltrating Regulatory T Cells Inhibit Endogenous Cytotoxic T Cell Responses to Lung Adenocarcinoma," The Journal of Immunology, 191(4): 2009-2017 (2013).
Garcia-Marco et al., "Frequent Somatic Deletion of the 13q12.3 locus Encompassing BRCA2 in Chronic Lymphocytic Leukemia," Blood, 88: 1568-1575 (1996).
Gascoigne et al., "Allelic exclusion of the T cell receptor a-chain: developmental regulation of post-translational event," Semin Immunol, 11:337-347 (1999).
Gazdar, "Activating and resistance mutations of EGFR in non-small-cell lung cancer: role in clinical response to EGFR tyrosine kinase inhibitors," Oncogene, 28:S24-S31 (2009).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gnirke et al., "Solution Hybrid Selection with Ultra-Long Oligonucleotides for Massively Parallel Targeted Sequencing," Nat Biotechnol, 27(2): 182-189 (2009).
Goh et al., "Mining the Structural Genomics Pipeline: Identification of Protein Properties that Affect High-throughput Experimental Analysis," Journal of Molecular Biology, 336(1): 115-130 (2004).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors," Bioinformatics, Original Paper, 26(6): 730-736 (2010).
Greenman et al., "Patterns of somatic mutation in human cancer genomes," Nature, 446:153-158 (2007).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).

(56) References Cited

OTHER PUBLICATIONS

Guo et al., "Different length peptids bind to HLA-Aw68 similarity at their ends but bulge on in the middle," Nature, 360:364-366 (1992).
Guruprasad et al., "Correlation between stability of a protein and its dipeptide composition: a novel approach for predicting in vivo stability of a protein from its primary sequence," Protein Eng, 4(2):155-161 (1990).
Haanen et al., "Immunotherapy of melanoma," Euro J Canc Supp 11:97-105 (2013).
Hacohen et al., "Getting Personal with Neoantigen-Based Therapeutic Cancer Vaccines," Cancer Immunol. Res, 1(1):11-15 (2013).
Hamid et al., "Safety and Tumor Responses with Lambrolizumab (Anti-PD-1) in Melanoma," The New England Journal of Medicine, 369(2):134-144 (2013).
Han et al., "Linking T-Cell Receptor Sequence to Fucntional Phenotype at the Single-Cell Level," Nat Biotechnol, 32:684-692 (2014).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB* 4402 and the HLA-B*4403 Molecules Which Differ by a Single Amino Acid," Tissue Antigens, 53: 111-121 (1999).
Hersey et al., "Phase I/II study of treatment with dendritic cell vaccines in patient with disseminated melanoma," Cancer Immunol Immunoother, 53:125-134 (2004).
Hickman et al., "Toward a Definition of Self: Proteomic Evaluation of the Class I Peptide Repertoire," J Immunol, 172:2944-2952 (2004).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100:4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hodi et al., "Improved Survival with Ipilimumab in Patients with Metastatic Melanoma," New Engl J Med, 363:711-723 (2010).
Hombrink et al., "Identification of Biological Relevant Minor Histocompatibility Antigens within the B-lymphocyte—Derived HLA-Ligandome Using a Reverse Immunology Approach," Clin Cancer Res, 21(9):2177-2186 (2015).
Hoof et al., "NetMHCpan, a method for MHC class I binding prediction beyond humans," Immunogenetics, 61:1-13 (2009).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hunt et al., "Characterization of peptides bound to the class I MHC molecule HLA-A2.1 by mass spectrometry," Science, 255:1261-1263 (1992).
IEDB Analysis Resource for MHC-I binding predictions (printed Oct. 2019).
IEDB Analysis Resource for MHC-II binding predictions (printed Oct. 2019).

Illumina, "Immunotherapy, the Next Generation of Cancer Treatment, NGS-guided assessment of interactions between tumors and the immune system leads to new discoveries in immuno-oncology," (2016).
Intellectual Property Policy for Partners-Affiliated Hospitals and Institutions, Aug. 15, 2002.
International Preliminary Report on Patentability for International Application No. PCT/US2011/036665 dated Nov. 20, 2020.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068893 dated Jun. 7, 2016. (our reference BIS-710.25).
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Preliminary Report on Patentability for International Application No. PCT/US2017/028122 dated Oct. 23, 2018.
International Search Report and Written Opinion for International Application No. PCT/US/2015/051340 dated Dec. 21, 2015.
International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report and Written Opinion for International Application No. PCT/US2017/028122 dated Apr. 18, 2016.
International Search Report and Written Opinion for International Application No. PCT/US2018/014831 dated Apr. 4, 2018.
International Search Report for International Application No. PCT/US2014/068746 dated Mar. 23, 2015.
International Search Report for International Application No. PCT/US2014/068893 dated Apr. 9, 2015.
International Search Report for International Application No. PCT/US2014/071707 dated Sep. 10, 2015.
Invention Agreement of the Dana-Farber Cancer Institute, Jul. 1, 1997.
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Japanese Office Action dated Jan. 22, 2018, which issured during prosecution of JP 2016-507587.
Japanese Office Action from Application No. 2013-510360 dated Apr. 28, 2015.
Jarmalavicius et al., "High Immunogenicity of the Human Leukocyte Antigen Peptidomes of Melanoma Tumor Cells," J Biol Chem, 287(40):33401-33411 (2012).
Jeffery et al., "The Influence of HLA Class I Alleles and Heterozygosity on the Outcome of Human T Cell Lymphotropic Virus Type I Infection," J Immunol, 165:7278-7284 (2000).
Ji et al., "An immune-active tumor microenvironment favors clinical response to ipilimumab," Cancer Immunol Immunother, 61(7):1019-1031 (2011).
Jiang et al., "GATA3 Mutations Define a Unique Subtype of Luminal-Like Breast Cancer With Improved Survival," Canc 120:1329-1337 (2014).
Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).

(56) References Cited

OTHER PUBLICATIONS

Johnson et al., "Discovery of Naturally Processed and HLA-Presented Class I Peptides from Vaccinia Virus Infection using Mass Spectrometry for Vaccine Development," Vaccine, 28(1):38-47 (2009).
Jorgensen et al., "NetMHC stab—predicting stability of peptide-MHC-I complexes; impacts for cytotoxic T lymphocyte epitope discovery," Immunology 141:18-26 (2014).
Jun et al., "Progress in T cell adoptive Immunotherapy for Malignant Solid Tumors," Chin Med Biotechnol, 3(1):1-7 (2008).
Kalaora et al., "Use of HLA peptidomics and whole exome sequencing to identify human immunogenic neo-antigens," Oncotarget, 7(5):5110-5117 (2016).
Kanduri et al., "Differential genome-wide array-based methylation profiles in prognostic subsets of chronic lymphocytic leukemia," Blood, 115(2):296-305 (2010).
Kanzler et al., "Therapeutic Targeting of Innate Immunity with Toll-like Receptor Agonists and Antagonists," Nat Med, 13: 552-559 (2007).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High-Risk Human Papillomavirus 16 in End-Stage Cervical Cancer Patients Show Low Toxicity and Robust Immunogenicity," Clin. Cancer Research, 14(1):169-177 (2008).
Keogh et al., "Identification of New Epitopes from Four Different Tumor-Associated Antigens: Recognition of Naturally Processed Epitopes Correlates with HLA-A☐0201-Binding Affinity," J Immunol, 167:787-796 (2001).
Keskin et al., "Direct identification of an HPV-16 tumor antigen from cervical cancer biopsy specimens," Front Immunol, 2:75 (2011).
Keskin et al., "Neoantigen vaccine generates intratumoral T cell responses in phase Ib glioblastoma trial," Nature, 565(7738):234-239 (2019).
Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kessler et al., "Identification of T-cell epitopes for cancer immunotherapy," Leukemia, 21:1859-1874(2007).
Khalili et al., "In silico prediction of tumor antigens derived from functional missense mutations of the cancer gene census," Oncoimmunology, 1(8):1281-1289 (2012).
Khammari et al., "Treatment of metastatic melanoma with autologous melan-A/mart-1-specific cytotoxic t lymphocyte clones," Journal of Investigative Dermatology, 129(12): 2835-2842 (2009).
Kim et al., "Derivation of an amino acid similarity matrix for peptide:MHC binding and its application as a Bayesian prior," BMC Bioinformatics, 10:1-11 (2009).
Kim et al., "Inactivating mutations of caspase-8 in colorectal carcinomas," Gastroenterology, 125:708-715(2003).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).
Kim et al., "Positional Bias of MHC Class I Restricted T-Cell Epitopes in Viral Antigens is Likely due to a Bias in Conservation," PLoS Comput Biol, 9:e1002884 (2013).
Klug et al., "Characterization of MHC Ligands for Peptide Based Tumor Vaccination," Current Pharmaceutical Design, 15(28): 3221-3236 (2009).
Kobayashi et al., "DNA methylation profiling reveals novel biomarkers and important roles for DNA methyltransferases in prostate cancer," Genome Research, 21:1017-1027 (2011).
Koh et al., "Immunological consequences of using three different clinical/laboratory techniques of emulsifying peptide-based vaccines in incomplete Freund's adjuvant," J Translational Med, 4:42 (2006).
Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kreiter et al., "Targeting the tumor mutanome for personalized vaccination therapy," OncoImmunology, 1 (5):768-769 (2012).
Krieg, "Therapeutic potential of Toll-like receptor 9 activation," Nature reviews Drug discovery, 5(6):471-484 (2006).
Kronenberger et al., "A Polyvalent Cellular Vaccine Induces T-cell Responses Against Specific Self-antigens Overexpressed in Chronic Lymphocytic B-cell Leukemia," J Immunother, 31(8): 723-730 (2008).
Kronke et al. "Lenalidomide causes selective degradation of IKZFI and IKZF3 in multiple myeloma cells," Science, 343(6168): 301-305 (2014).
Kronke et al. "Lenalidomide induces ubiquitination and degradation of CKla in del(5q) MDS," Nature, 523(7559):183-188 (2015).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147(1991).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Landau et al., "Chronic lymphocytic leukemia: molecular heterogeneity revealed by high-throughput genomics," Genome Med, 5:47 (2013).
Landau et al., "Increased Local Disorder of DNA Methylation Forms the Basis of High Intra-Leukemic Epigenetic Heterogeneity and Enhances CLL Evolution," Blood, 122:596 (2013).
Landau et al., "The evolutionary landscape of chronic lymphocytic leukemia treated with ibrutinib targeted therapy," Nat Commun, 8(1):2185 (2017).
Larsen et al., "Large-scale validation of methods for cytotoxic T-lymphocyte epitope prediction," BMC Bioinformatics, 8:424-424 (2007).
Lata et al., "MHCBN 4.0: A database of MHC/TAP binding peptides and T-cell epitopes," BMC Research Notes, 2(1): 61 (2009).
Le et al., "Next-Generation Cancer Vaccine Approaches: Integrating Lessons Learned From Current Successes With Promising Biotechnologic Advances," J Natl Compr Cancer Network, 11:766-772 (2013).
Lee, "Identification of Neo-antigens for a Cancer Vaccine by Transcriptome Analysis", PhD Thesis, Arizona State University (2012).
Lemmel et al., "Differential quantitative analysis of MHC ligands by mass spectrometry using stable isotope labeling," Nature Biotechnology, 22(4):450-454 (2004).
Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA." Genes IV, 4:68-69(1990).
Lewintre et al., "Analysis of chronic lymphotic leukemia transcriptomic profile: differences between molecular subgroups," Leuk Lymphoma, 50:68-79 (2009).
Ley et al., "DNA sequencing of a cytogenetically normal acute myeloid leukaemia genome," Nature, 456: 66-72 (2008).
Ley et al., "DNMT3A Mutations in Acute Myeloid Leukemia", The New England Journal of Medicine, 363: 2423-2433 (2010).
Li et al., "Cancer Genome Sequencing and Its Implications for Personalized Cancer Vaccines," Cancers 3(4):4191-4211 (2011).
Lin et al., "Evaluation of MHC-II Peptide Binding Prediction Servers: Applications for Vaccine Research," BMC Bioinformatics, 9: S22 (2008).
Linard et al., "A ras-Mutated Peptide Targeted by CTL Infiltrating a Human Melanoma Lesion." J Immunol, 168:4802-4808 (2002).

(56) References Cited

OTHER PUBLICATIONS

Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al. "Somatic EGFR mutations and efficacy of tyrosine kinase inhibitors in NSCLC," Nat Rev Clin Oncol, 6(6):352-366 (2009).
Lindhout et al., "Site-specific enzymatic polysialylation of therapeutic proteins using bacterial enzymes," PNAS, 108(18):7397-7402 (2011).
Linnemann et al., "High-throughput epitope discovery reveals frequent recognition of neo-antigens by CD4+ T cells in human melanoma," Nat Med, 21:81-85 (2015).
Linnemann et al., "High-throughput identification of antigen-specific TCRs by TCR gene capture," Nat Med, 19(11):1534-1541 (2013).
Llano et al., "Best-Characterized HIV-1 CTL Epitopes: The 2013 Update," HIV Mol Immunol , 3-25 (2013).
Lorente et al., "Diversity of Natural Self-Derived Ligands Presented by Different HLA Class I Molecules in Transporter Antigen Processing-Deficient Cells," PLoS ONE 8:e59118 (2013).
Loveridge et al., "The genetic contribution to human T-cell receptor repertoire," Immunology, 74:246-250(1991).
Lucas et al., "About human tumor antigens to be used in immunotherapy," Semin Immunol, 20(5):301-307 (2008).
Lundegaard et al., "NetMHC-3.0: accurate web accessible predictions of human, mouse and monkey MHC class I affinities for peptides of length 8-11," Nucleic Acids Research, 36: W509.W512 (2008).
Lundegaard et al., "State of the art and challenges in sequence based T-cell epitope prediction," Immunome Research, 6(Suppl 2): S3 (2010).
Luo et al. "Machine learning methods for Predicting hla-Peptide Binding activity," Bioinformatics and Biology Insights, 9(s3):21-29 (2015).
Ma, "Novor: Real-Time Peptide de Novo Sequencing Software," J Am Soc Mass Spectrom, 26:1885-1894 (2015).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Mackall et al., "Targeting tumor specific translocations in sarcomas in pediatric patients for immunotherapy," Clinical Orthopaedics and Related Research, 373:25-31 (2000).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavota et al., "Interpretation of the dissolution of insoluble peptide sequences based on the acid-base properties of the solvent," Protein Sci, 15(6):1476-1488 (2006).
Malcikova et al., "Identification of somatic hypermutations in the TP53 gene in B-cell chronic lymphocytic leukemia," Molecular Immunol, 45(5):1525-1529 (2008).
Mandelboim et al., "Regression of Established Murine Carcinoma Metastases Following Vaccination with Tumor-Associated Antigen Peptides," Nature Medicine, 1(11):1179-1183 (1995).
Mandruzzato et al., "A CASP-8 Mutation Recognized by Cytolytic T Lymphocytes on a Human Head and Neck Carcinoma," J Exp Med, 186: 785-793 (1997).
Mardis et al., "Cancer genome sequencing: a review," Human Molecular Genetics, 18(2): R163-R168 (2009).
Mardis et al., "Recurring Mutations Found by Sequencing an Acute Myeloid Leukemia Genome," New Engl J Med, 361:1058-1066 (2009).

Mardis, "The impact of next-generation sequencing technology on genetics," Trends in Genetics, 24(3):133-141 (2007).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1- or HA-2-specific T Cells can Induce Complete Remissions of Relapsed Leukemia," PNAS, 100: 2742-2747 (2003).
Marina et al., "Serologic Markers of Effective Tumor Immunity Against Chronic Lymphocytic Leukemia Include Nonmutated B-Cell Antigens," Cancer Res, 70(4): 1344-1355 (2010).
Mark et al., "Site-specific mutagenesis of the human fibroblast interferon gene," PNAS, 81(18):5662-5666 (1984).
McCleskey et al., "GATA-3 Expression in Advanced Breast Cancer: Prognostic Value and Organ-Specific Relapse," Amer J Clin Pathol 144:756-763 (2015).
McMurtrey et al., "Toxoplasma gondii peptide ligands open the gate of the HLA class I binding groove," eLife 5:e12556 (2016).
Men et al., "Assessment of Immunogenicity of Human Melan-A Peptide Analogues in HLA-A*0201/Kb Transgenic Mice," J Immunol, 162:3566-3573 (1999).
Meyerson et al., "Advances in understanding cancer genomes through second-generation sequencing," Nat Rev Genetics, 11:685-696 (2010).
Mikeska et al., "The implications of heterogeneous DNA methylation for the accurate quantification of methylation," Epigenomics, 2(4):561-573 (2010).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Miyamoto et al., "GATA binding protein 3 is down-regulated in bladder cancer yet strong expression is an independent predictor of poor prognosis in invasive tumor," Human Pathology, 43:2033-2040 (2012).
Mkrtichyan et al., "B117 Defining a novel mechanism of a-PD1 synergy with vaccine to induce potent anti-tumor effects," Clinical Exp. Metastasis, 28, Abstract #B117(247-248): 157-259 (2011).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).
Mosmann et al., "TH1 and TH2 Cells: Different Patterns of Lymphokine Secretion Lead to Different Functional Properties," Ann Rev Immunol, 7:145-173 (1989).
Mullally et al., "Beyond HLA: The Significance of Genomic Variation for Allogeneic Hematopoietic Stem Cell Transplantation," Blood, 109: 1355-1362 (2007).
Muntel et al., "Abundance-based Classifier for the Prediction of Mass Spectrometric Peptide Detectability Upon Enrichment (PPA)," Mol Cell Proteomics, 14:430-440 (2015).
Murphy et al., "Antigen Presentation to T Lymphocytes," Janeway's Immunobiology, 7th Edition, 5:182-83 & 197 (2008).
Ng et al., "Dereplication and de novo sequencing of nonribosomal peptides," Nat Meth, 6:596-599 (2009).
Nielsen et al., "NetMHCpan-3.0; improved prediction of binding to MHC class I molecules integrating information from multiple receptor and peptide length datasets," Genome Medicine. 8:33 (2016).
Nielsen et al., "The role of the proteasome in generating cytotoxic T-cell epitopes: insights obtained from improved predictions of proteasomal cleavage," Immunogenetics, 57:33-41 (2005).
Niwa et al., "Bimodal protein solubility distribution revealed by an aggregation analysis of the entire ensemble of *Escherichia coli* proteins," PNAS, 106(11): 4201-4206 (2009).
Non-Final Office Action for U.S. Appl. No. 13/108,610, "Compositions and Methods of Identifying Tumor Specific Neoantigens," dated Aug. 15, 2013.

(56) References Cited

OTHER PUBLICATIONS

Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, "Compositions and Methods for Diagnosing, Evaluating and Treating Cancer By Means of the DNA Methyl," dated Sep. 6, 2017.
Non-Final Office Action for U.S. Appl. No. 15/102,129, "Formulations for Neoplasia Vaccines," dated Apr. 26, 2019.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 21, 2021.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Dec. 4, 2020.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 15/575,328, "Shared Neoantigens," dated Jun. 27, 2019.
Non-Final Office Action for U.S. Appl. No. 16/181,098, "Compositions and Methods of Identifying Tumor Specific Neoantigens," dated Jan. 31, 2019.
Non-Final Office Action for U.S. Appl. No. 16/181,098, "Compositions and Methods of Identifying Tumor Specific Neoantigens," dated Oct. 29, 2020.
Non-Final Rejection for U.S. Appl. No. 14/877,125, "Compositions and Methods for Personalized Neoplasia Vaccines," dated Feb. 3, 2020.
Non-Final Rejection for U.S. Appl. No. 15/038,504, "Compositions and Methods for Diagnosing, Evaluating and Treating Cancer By Means of the DNA Methylation Status." dated Feb. 4, 2020.
Non-Final Rejection for U.S. Appl. No. 15/105,961, "Combination Therapy With Neoantigen Vaccine," dated Jun. 2, 2020.
Non-Final Rejection for U.S. Appl. No. 15/513,127, "Use of Clonal Evolution Analysis for Ibrutinib Resistance in Chronic Lymphocytic Leukemia Patients," dated Oct. 29, 2019.
Non-Final Rejection for U.S. Appl. No. 15/537,785, "Methods for Profiling the T Cell Repertoire," dated May 11, 2020,
Non-Final Rejection for U.S. Appl. No. 15/537,839, "Molecular Biomarkers for Cancer Immunotherapy," dated Oct. 8, 2019.

Non-Final Rejection for U.S. Appl. No. 15/735,566, "Formulations for Neoplasia Vaccines and Methods of Preparing Thereof," dated May 28, 2020.
Non-Final Rejection for U.S. Appl. No. 15/800,732, "Compositions and Methods of Identifying Tumor Specific Neoantigens," dated Apr. 10, 2020.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Notice of Allowance for U.S. Appl. No. 15/575,328, "Shared Neoantigens," dated Jan. 23, 2020.
Notice of Allowance for U.S. Appl. No. 16/188,737, "Compositions and Methods of Identifying Tumor Specific Neoantigens," dated Jul. 25, 2019.
Notice of Opposition to European Patent No. EP2569633—Agenus Inc. (Opponent) dated Nov. 9, 2016.
Notice of Opposition to European Patent No. EP2569633—Dr. Christian Muller (Opponent) dated Nov. 9, 2016.
Notice of Opposition to European Patent No. EP2569633—Gritstone Oncology, Inc. (Opponent) dated Nov. 7, 2016.
Notice of Opposition to European Patent No. EP2569633—James Poole Limited (Opponent) dated Nov. 9, 2016.
Notice of Opposition to European Patent No. EP2569633—Strawman Limited (Opponent) dated Nov. 10, 2016.
Novellino et al., "A listing of human tumor antigens recognized by T cells: Mar. 2004 update," Cancer Immunol Immunother, 54(3):187-207 (2005).
Nyren et al., "Solid Phase DNA Minisequencing by an Enzymatic Luminometric Inorganic Pyrophosphate Detection Assay," Anal Biochem, 208(1): 171-175 (1993).
O'Mahony et al., "A Pilot Study of CTLA-4 Blockade after Cancer Vaccine Failure in Patients with Advanced Malignancy" Clin Cane Res 13(3):958-964 (2007).
O'Shea et al., "Signal transduction and Th17 cell differentiation," Microbes Infect, 11 (5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocytic Leukemia," Blood, 122(21):1626 (2013).
Oates et al., "D(2)P(2): database of disordered protein predictions," Nucleic Acids Res, 41:D508-D516(2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Ohashi et al., "Lung cancers with aquired resistance to EGFR inhibitors occasionally harbor BRAF gene mutations but lack mutations in KRAS, NRAS, or MEK1," PNAS, E2127-E2133 (2012).
Opavsky et al., CpG Island Methylation in a Mouse Model of Lymphoma Is Driven by the Genetic Configuration of Tumor Cells, PLOS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.
Opposition Letter—Strawman Limited (Opponent) in European Patent No. 2569633 dated Nov. 10, 2016.
Osorio et al., "Stability Analysis of Antimicrobial Peptides in Solvation Conditions by Molecular Dynamics," Adv Comp Bio, 232:127-131 (2014).

(56) References Cited

OTHER PUBLICATIONS

Ott et al., "A Phase lb Trial of Personalized Neoantigen Therapy Plus Anti-PD-1 in Patients with Advanced Melanoma, Non-small Cell Lung Cancer, or Bladder Cancer," Cell, 183(2):347-362 (2020).
Ott et al., "An Immunogenic personal neoantigen vaccine for patients with melanoma," Nature, 547:217-221 (2017).
Ott et al., "Vaccines and Melanoma," Hematol Oncol Clin N Am, 28(3):559-569 (2014).
PAIR Screenshot Patent Assignment Abstract of Title of U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A*0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Peters et al., "Accurate whole-genome sequencing and haplotyping from 10 to 20 human cells," Nature 487:190-195 (2012).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Phan et al., "Cancer regression and autoimmunity induced by cytotoxic T lymphocyte-associated antigen 4 blockade in patients with metastatic melanoma," PNAS, 100(14):8372-8377 (2003).
Pietras, "Biologic Basis of Sequential and Combination Therapies for Hormone-Responsive Breast Cancer," Oncologist, 11:704-717 (2006).
Pilla et al., "Multipeptide vaccination in cancer patient," Expert Opin Biol Ther, 9(8):1043-1055 (2009).
Piros et al., "Market Opportunity for Molecular Diagnostics in Personalized Cancer Therapy," Handbook of Clinical Nanomedicine: Law, Business, Regulation, Safety and Risk, Chapter 14:1-29 (2016).
Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463:184-190 (2010).
Policy Reallocating Ownership of Intellectual Property Covered by the Intellectual Property Policy, Sep. 18, 2002.
Poster entitled "Disease-related biomarkers are associated with extended progression-free survival after treatment with Neo-PV-01 in combination with anti-PD1 in patients with metastatic cancers" presented at The Society for Immunotherapy of Cancer Annual Meeting Nov. 6-10, 2019 ("SITC 2019 poster").
Prezant et al., "Trapped-Oligonucleotide Nucleotide Incorporation (TONI) Assay, a Simple Method for Screening Point Mutations," Hum Mutat, 1(2): 159-164 (1992).
Pritchard et al., "Exome Sequencing to Predict Neoantigens in Melanoma." Cancer Immunol Res, 3:992-998 (2015).
Provan et al., "Eradication of Polymerase Chain Reaction-Detectable Chronic Lymphocytic Leukemia Cells is Associated with Improved Outcome After Bone Marrow Transplantation." Blood, 88:2228-2235 (1996).
Public Pair Assignment Data Screenshot of U.S. Appl. No. 61/334,866, filed May 14, 2010.
Rajasagi et al.. "Systematic Identification of Personal Mutated Tumor-Specific Neoantigens in CLL," Blood, 120(21):954 (2012).
Rajasagi et al., "Systematic identification of personal tumor-specific neoantigens in chronic lymphocytic leukemia," Blood, 124(3):453-462 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Restifo et al., "Adoptive immunotherapy for cancer: harnessing the T cell response," Nat Rev Immunol, 12(4):269-281 (2015).
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504 , "Compositions and Methods for Diagnosing, Evaluating and Treating Cancer By Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961 , "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/537,839, "Molecular Biomarkers for Cancer Immunotherapy," dated Jun. 20, 2019.
Restriction Requirement for U.S. Appl. No. 15/575,328, "Shared Neoantigens," dated Feb. 7, 2019.
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol, 23(35): 8968-8977 (2005).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Robinson et al., "The IPD and FMGT/HLA database: allele variant databases," Nucleic Acids Res, 43:D423-D431 (2015).
Rock et al., "Re-examining class-I presentation and the DRiP hypothesis," Trends Immunol, 35(4):144-152 (2014).
Rondon et al., "Graft-versus-Leukemia Effect After Allogeneic Bone Marrow Transplantation for Chronic Lymphocytic Leukemia," Bone Marrow Transplant, 18: 669-672 (1996).
Rosenberg et al., "Cancer Immunotherapy: Moving Beyond Current Vaccines," Nat Med, 10: 909-915(2004).

(56) References Cited

OTHER PUBLICATIONS

Rubin et al., "Mutation patterns in cancer genomes," PNAS, 106(51):21766-21770 (2009).
Rubinfeld et al., "Stabilization of Beta-Catenin by Genetic Defects in Melanoma Cell Lines," Science, 275(5307):1790-1792 (1997).
Ruggles et al., "An analysis of the sensitivity of proteogenomic mapping of somatic mutations and novel splicing events in cancer," Cell Proteomics, 15(3):1060-1071 (2015).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Sahin et al., "Personalized RNA mutanome vaccines mobilize poly-specific therapeutic immunity against cancer," Nature, 547(7662):222-226 (2017).
Sanderson et al., Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma, J Clin Oncol, 23(4)741-750 (2005).
Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response To Tumor and Viral Peptide Antigens By An IFNy-ELISPOT Assay," Int. J. Cancer, 71:932-936 (1997).
Schietinger et al., "Specificity in cancer immunotherapy," Semin. Immunol, 20(5)276-285 (2008).
Schuh et al., "Monitoring chronic lymphocytic leukemia progression by whole genome sequencing reveals heterogeneous clonal evolution patterns," Blood, 120(20):4191-4196 (2012).
Schumacher et al., "Neoantigens in cancer immunotherapy," Science, 348:69-74 (2015).
Schwitalle et al., "Immunogenic peptides generated by frameshift mutations in DNA mismatch repair-deficient cancer cells," Cancer Immunity, 4(1):14 (2004).
Searle et al., "Using Data Independent Acquisition (DIA) to Model High-responding Peptides for Targeted Proteomics Experiments," Mol Cell Proteomics, 14:2331-2340 (2015).
Segal et al. "Epitope Landscape in Breast and Colorectal Cancer," Cancer Res, 68: 889-892 (2008).
Sensi et al., "Unique Tumor Antigenesis: Evidence for Immune Control of Genome Integrity and Immunogenic for T Cell-Mediated Patient-Specific Immunotherapy," Clin Cancer Res, 12(7): :5023-5032 (2006).
Sette et al., "Peptide binding to the most frequent HLA-A class I alleles measured by quantitative molecular binding assays," Molecular Immunology, 31(11): 813-822 (1994).
Sette et al., "The relationship between class I binding affinity and immunogenicity of potential cytotoxic T cell epitopes," J Immunol, 153:5586-5592 (1994).
Shames et al., "A Genome-Wide Screen for Promoter Methylation in Lung Cancer Identifies Novel Methylation Markers for Multiple Malignancies," PLOS Med, 3(12):e486 (2006).
Sharma et al., "A Chromatin-Mediated Reversible Drug-Tolerant State in Cancer Cell Subpopulations," Cell, 141:69-80 (2010).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shen et al., "Integrated genetic and epigenetic analysis identifies three different subclasses of colon cancer," PNAS, 104(47):18654-18659 (2007).
Shendure et al., "Next-generation DNA sequencing," Nat Biotechnol, 26(10):1135-1145 (2008).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Sidney et al., "Measurement of MHC/Peptide Interactions by Gel Filtration or Monoclonal Antibody Capture," Curr Protoc Immunol: 18.3.1-18.3.36 (2013).
Sidney et al., "Measurement of MHC/Peptide Interactions by Gel Filtration" Curr Prot Immunol, 31(1):18.3.1-18.3.19 (1999).
Siegmund et al., "Inferring clonal expansion and cancer stem cell dynamics from DNA methylation patterns in colorectal cancers," PNAS, 106(12):4828-4833 (2009).
Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sjoblom et al., "The Consensus Coding Sequences of Human Breast and Colorectal Cancers," Science, 314(5797):268-274 (2006).
Smialowsky et al., "Protein solubility: sequence based prediction and experimental verification," Bioinformatics, 23(19):2356-3542 (2007).
Snyder et al., "Genetic Basis for Clinical Response to CTLA-4 Blockade in Melanoma," New Engl J Med, 371 (23):2189-2199 (2014).
Snyder et al., "Immunogenic peptide discovery in cancer genomes," Cuff Opin Genet Dev, 30: 7-16(2015).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).
Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Sokolov., "Primer Extension Technique for the Detection of Single Nucleotide in Genomic DNA," Nucleic Acids Res. 18(12): 3671 (1990).
Song et al., "Full screening and accurate subtyping of HLA-A*02 alleles through group-specific amplification and mono-allelic sequencing," Cell Mol Immunol, 10:490-496 (2013).
Soung et al., "Capase-8 gene is frequently inactivated by the frameshift somatic mutation 1225 1226delTG in hepatocellular carcinomas," Oncogene, 24:141-147 (2005).
Sowa et al., "Defining the Human Deubiquitinating Enzyme Interaction Landscape," Cell, 138(2):389-403 (2009).
Spitler, "Cancer Vaccines: The Interferon Analogy," Cancer Biother, 10:1-3 (1995).
Srivastava et al., "Modeling the Repertoire of True Tumor-Specific MHC I Epitopes in a Human Tumor," PLOS ONE, 4(7):e6094 (2009).
Srivastava, "Therapeutic Cancer Vaccines," Curr Opin Immunol, 18: 201-205 (2006).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103:291-300 (2004).
Stranzl et al., "NetCTLpan: pan-specific MHC class I pathway epitope predictions," Immunogenetics, 62(6):357-368 (2010).

(56) References Cited

OTHER PUBLICATIONS

Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Su et al., "Next-generation sequencing and its applications in molecular diagnostics" Exp Rev Mol Diagn, 11(3):333-343 (2011).
Submission in opposition proceedings of EP 2569633, dated Jun. 28, 2017.
Sun et al., Material bionics and Thinking Innovation, 176-177 (2012).
Supplementary Materials from Third Party Observation in EP Application No. 15198284.0.
Syvanen et al., "A Primer-Guided Nucleotide Incorporatiopn Assay in the Genotyping of Apoliprotein E," Genomics, 8(4): 684-692 (1990).
Syvanen et al., "Identification of Individuals by Analysis of Biallelic DNA Markers, Using PCR and Solid-Phase Minisequencing," Am J Hum Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc., to EP Patent No. 2569633.
Tang et al., "NeoantigenR: An annotation based pipeline for tumor neoantigen identification from sequencing data," bioRxiv preprint first posted online Aug. 8, 2017.
Thomas et al., "High-Throughput Oncogene Mutation Profiling in Human Cancer," Nat Genet, 39: 347-351 (2007).
Thompson et al., "Aberrations of the B-Cell Receptor B29 (CD79b) Gene in Chronic Lymphocytic Leukemia," Blood, 90(4):1387-1394 (1997).
Thon et al., "Personalized treatment strategies in glioblastoma: MGMT promoter methylation status," Onco Targets and Therapy, 6:1363-1372 (2013).
Thornton et al., "Characterisation of TP53 Abnormalities in Chronic Lymphocytic Leukaemia." Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).
Tong et al., "Methods and protocols for prediction of immunogenic epitopes", Briefings In Bioinformatics, 8(2): 96-108 (2008).
Topalian et al., "Targeting the PD-1/B7-H1(PD-L1) pathway to activate anti-tumor immunity," Current Opinion in Immunology, 24:207-212 (2012).
Tourdot et al., "A general strategy to enhance immunogenicity of low-affinity HLA-A2.1-associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).
Trolle et al., "Automated benchmarking of peptide-MHC class I binding predictions," Bioinformatics, 31(13):2174-2181 (2015).
Trolle et al., "The Length Distribution of Class I-Restricted T Cell Epitopes Is Determined by Both Peptide Supply and MHC Allele-Specific Binding Preference," J Immunol (2016), doi: 10.4049/jimmunol.1501721.
Tumeh et al., "PD-1 blockade induces responses by inhibiting adaptive immune resistance," Nature, 515(7528):568-571 (2014).
Turchaninova et al., "Pairing of T-cell receptor chains via emulsion PCR," Eur J Immunol, 43:2507-2515(2013).
Tynan et al., "T cell receptor recognition of a "super-bulged" major histocompatibility complex class I-bound peptide," Nat Immunol, 6:1114-1122 (2005).

U.S. Final Office Action dated May 25, 2017 and issued in U.S. Appl. No. 15/187,174.
U.S. Final Rejection dated Sep. 13, 2017 and issued in U. S. U.S. Appl. No. 14/794,449.
U.S. Non-Final Office Action dated Jan. 22, 2018 and issued in U.S. Appl. No. 15/187,174.
U.S. Non-Final Office Action dated Mar. 7, 2019 and issued in U.S. Appl. No. 15/037,394.
U.S. Non-Final Office Action dated Oct. 2, 2020 and issued in U.S. Appl. No. 15/037,394.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Udeshi et al., "Methods for quantification of in vivo changes in protein ubiquitination following proteasome and deubiquitinase inhibition," Mol Cell Proteomics, 11:148-159 (2012).
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts—Q5SW79 filed on Nov. 2016 in Muller Opposition to EP 2569633.
Van Buuren et al., "High sensitivity of cancer exome-based CD8 T cell neo-antigen identification," OncoImmunology, 3(5):e28836 (2014).
Van de Roemer et al., "P1737:IVAC: Individualized vaccines for cancer," Immunology 137(Suppl. 1):715, Sep. 2012.
Van Den Broeke et al., "Identification and Eiptope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors," American Association for Cancer Research, 66(3):1818-1823 (2006).
Van der Bruggen et al., "A Gene Encoding an Antigen Recognized by Cytolytic T Lymphocytes on a Human Melanoma," Science, 254: 1643-1647 (1991).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Trappen et al., "Somatic Mitochondrial DNA Mutations in Primary and Metastatic Ovarian Cancer," Gynecol Oncol, 104: 129-133 (2007).
Vandenberghe et al., "Heparin binding directs activation of T cells against adeno-associated virus serotype 2 capsid," Nature Medicine, 12(8): 967-971 (2006).
Vandrovcova et al., :Somatic BRAF-V600E Mutations in Familial Colorectal Cancer, Cancer Epidemio Biomarkers Prev, 15(11):2270-2273 (2006).
Varley et al., "Intra-tumor heterogeneity of MLH1 promoter methylation revealed by deep single molecule bisulfite sequencing," Nucleic Acids Research, 37(14):4603-4612 (2009).
Verhoef et al., "Des-enkephalin-γ-endorphin (DEγE): Biotransformation in rat, dog and human plasma," Eur J Drug Metab Ph, 11(4):291-302 (1986).
Vita et al., "The immune epitope database (IEDB) 3.0," Nucleic Acids Res, 43:D405-D412 (2015).
Vita et al., "The Immune Epitope Database 2.0," Nucleic Acids Res, 38:D854-D862 (2010).
Vogel et al., "Mass Spectrometry Reveals Changes in MHC I Antigen Presentation After Lentivector Expression of a Gene Regulation System," Molecular Therapy-Nucleic Acids, 2:e75 (2013).
Vogelstein et al., "Cancer Genome Landscapes," Science, 339(6127): 1546-1558 (2013).
Volpe et al., "Alternative BCR/ABL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Walter et al., "DNA Methylation Profiling Defines Clinically Relevant Biological Subsets of Non-small Cell Lung Cancer," Clin Cancer Res, 18(8):2360-2373 (2012).
Walz et al., "The antigenic landscape of multiple myeloma: mass spectrometry (re)defines targets for T-cell-based immunotherapy," Blood 126:1203-1213 (2015).

(56) References Cited

OTHER PUBLICATIONS

Wang et al., Functional Polymeric Material, 1-44 (2010).
Wang, "Tumor Antigens Discovery: Perspectives for Cancer Therapy", Molecular Medicine, 3(11): 716-731 (1997).
Weber et al., "Safety, Efficacy, and Biomarkers of Nivolumab With Vaccine in Ipilimumab-Refractory or -Naive Melanoma," J Clin Oncol, 31:4311-4318 (2013).
Weinschenk et al., "Integrated Functional Genomics Approach for the Design of Patientindividual Antitumor Vaccines," Cancer Res, 62: 5818-5827 (2002).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Wolfel et al., "A p16INK4a-insensitive CDK4 mutant targeted by cytolytic T lymphocytes in a human melanoma," Science, 269(5228):1281-1284 (1995).
Wood et al., "The Genomic Landscapes of Human Breast and Colorectal Cancers," Science, 318: 1108-1113(2007).
Woodbury et al., "Introduction to Macromolecular Binding Equilibria," CRC Press, 13:978 (2007).
Wraith, "The Future of Immunotherapy: A 20-Year Perspective," Front Immunol, 8(1668): 1-6 (2017).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Induction of Tumor Immunity Following Allogeneic Stem Cell Transplantation," Adv Immunol, 90: 133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yao et al., "Advances in targeting cell surface signalling molecules for immune modulation," Nature Rev Drug Discov, 12:130-146 (2013).
Yee et al., "Adoptive T cell therapy using antigen-specific CD8 T cell clones for the treatment of patients with metastatic melanoma: In vivo persistence, migration, and antitumor effect of transferred T cells," PNAS, 99(25): 16168-16173 (2002).
Yewdell, "DRiPs solidify: progress in understanding endogenous MHC class I antigen processing," Trends Immunol, 32(11):548-558 (2011).
Yokoyama et al., "Matrilysin (MMP-7) Is a Novel Broadly Expressed Tumor Antigen Recognized by Antigen-Specific T Cells," Clin Cancer Res, 14(17): 5503-5511 (2008).
Yosef et al., "Dynamic regulatory network controlling TH17 cell differentiation," Nature, 496(7446):461-468 (2013).
You et al., "Understanding Prediction Systems for HLA-Binding Peptides and T-Cell Epitope Identification," Pattern Recognition in Bioinformatics, Lecture Notes in Computer Science, 4474: 337-348 (2007).
Zhang et al., "Dana-Farber repository for machine learning in immunology," J Immunol Methods, 374(1-2):18-25 (2011).
Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhang et al., "The impact of next-generation sequencing on genomics," J Genet Genomics, 38(3):95-109 (2011).
Zhang et al., Oncology, 1-44 (2005).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65: 1079-1088 (2005).
Zhou et al., "Transcriptional regulatory networks in Th17 cell differentiation," Curr Opin Immunol, 21 (2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).
Acevedo et al., "Analysis of the mechanisms mediating tumor-specific changes in gene expression in human liver tumors," Cancer Res, 68(8):2641-2651 (2008).
Adams, "Toll-like receptor agonists in cancer therapy," Immunotherapy, 1(6):949-964 (2009).
Akiyama et al., "GATA-4 and GATA-5 transcription factor genes and potential downstream antitumor target genes are epigenetically silenced in colorectal and gastric cancer," Mol Cell Biol, 23:8429-8439 (2003).
Alarcon et al., "DNA vaccines: technology and application as anti-parasite and anti-microbial agents," Advances in Parasitology, 42:343-410 (1999).
Ali et al., "In situ regulation of DC subsets and T cells mediates tumor regression in mice," Cancer Immunotherapy, 1(8):1-10 (2009).
Ali et al., "Infection-mimicking materials to program dendritic cells in situ," Nat Mater, 8:151-8 (2009).
Allison, "The Mode of Action of Immunological Adjuvants," Dev Biol Stand, 92: 3-11 (1998).
Almeida et al., "CTdatabase: a knowledge-base of high-throughput and curated data on cancer-testis antigens," Nucleic acids research, 37:0816-819 (2008).
Altman et al., "Phenotypic analysis of antigen-specific T lymphocytes," Science, 274(5284):94-6 (1996).
Alvarez, "Present and future evolution of advanced breast cancer therapy," Breast Cancer Research, 12(Suppl 2):S1 (2010).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., "HTSeq-A Python framework to work with high-throughput sequencing data," Bioinformatics, 31(2):166-169 (2015).
Andersen et al., "Parallel detection of antigen-specific T cell responses by combinatorial encoding of MHC multimers," Nature protocols, 7(5):891-902 (2012).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Aucouturier et al., "Adjuvants designed for veterinary and human vaccines," Vaccine, 19(17-19):2666-2672 (2001).
Ausubel, "A botanical macroscope," Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Baden et al., "First-in-human evaluation of the safety and immunogenicity of a recombinant adenovirus serotype 26 HIV-1 Env vaccine (IPCAVD 001)," J Infect Dis, 207(2):240-247 (2012).

(56) References Cited

OTHER PUBLICATIONS

Balagaan et al., "Stable and efficient intraocular gene transfer using pseudotyped EIAV lentiviral vectors," J Gene Med, 8:275-285 (2005).
Balazsi et al., "Cellular decision making and biological noise: from microbes to mammals," Cell, 144(6):910-925 (2011).
Balch et al., "Final version of 2009 AJCC melanoma staging and classification," Journal of clinical oncology, 27(36):6199-6206 (2009).
Barbie et al., "Systematic RNA interference reveals that oncogenic KRAS-driven cancers require TBK1" Nature, 462:108-112 (2009).
Barretina et al., "The Cancer Cell Line Encyclopedia enables predictive modelling of anticancer drug sensitivity," Nature, 483:603-607 (2012).
Baylin, "A decade of exploring the cancer epigenome-biological and translational implications," Nat Rev Cancer, 11:726-734 (2005).
Baylin, "DNA methylation and gene silencing in cancer," Nat Clin Pract Oncol 2, Suppl 1, S4-11 (2005).
Benson, "Tandem repeats finder: a program to analyze DNA sequences," Nucleic acids research, 27(2):573-580 (1999).
Benton et al., "Screening lambdagt recombinant clones by hybridization to single plaques in situ," Science, 196(4286):180-182 (1977).
Berger et al., "The genomic complexity of primary human prostate cancer," Nature, 470:214-220 (2011).
Berman et al., "Regions of focal DNA hypermethylation and long-range hypomethylation in colorectal cancer coincide with nuclear lamina-associated domains," Nat Genet, 44:40-46 (2012).
Bhardwaj et al., "TLR Agonists: Are They Good Adjuvants?," Cancer J, 16:382-391 (2010).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).
Birrell et al., "A genome-wide screen in *Saccharomyces cerevisiae* for genes affecting UV radiation sensitivity," Proceedings of the National Academy of Sciences 98(22):12608-12613 (2001).
Bishop et al., "APOBEC-mediated editing of viral RNA," Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Bock et al., "BIQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boller et al. "Characterization of the antibody response specific for the human endogenous retrovirus HTDV/HERV-K," Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).
Bequest et al., "Isolation and transcription profiling of purified uncultured human stromal stem cells: alteration of gene expression after in vitro cell culture," Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway." Proceedings of the National Academy of Sciences, 110: 3465-3470 (2013).
Bozic et al., "Dynamics of targeted cancer therapy," Trends Mol Med, 18:311-316(2012).
Bozic et al., "Evolutionary dynamics of cancer in response to targeted combination therapy," Elife, 2:e00747 (2013).
Brahmer et al., "Safety and activity of anti-PD-L1 antibody in patients with advanced cancer," N Engl J Med, 366(26):2455-2465 (2012).
Brochier et al., "Large-scale eradication of rabies using recombinant vaccinia-rabies vaccine," Nature, 354:520-552 (1991).
Brown et al., "Integrative genomic analysis implicates gain of PIK3CA at 3g26 and MYC at 8q24 in chronic lymphocytic leukemia," Clin Cancer Res, 8:3791-802 (2012).
Brunsvig et al., "Telomerase Peptide Vaccination: A Phase I/II Study in Patients with Non-Small Cell Lung Cancer," Cancer Immunol Immunother, 55(12): 1553-1564 (2006).
Buchschacher et al., "Human immunodeficiency virus vectors for inducible expression of foreign genes." Journal of virology, 66(5):2731-2739 (1992).
Buckwaiter et al., "'It is the antigen(s), stupid' and other lessons from over a decade of vaccitherapy of human cancer," Seminar in Immunology, 20(5):296-300 (2008).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "B cell receptor signaling in chronic lymphocytic leukemia," Trends Immunol, 34:592-601 (2013).
Burkhardt et al., "Autologous CLL cell vaccination early after transplant induces leukemia-specific T cells," The Journal of clinical investigation, 123(9):3756-3765 (2013).
Buser et al., "Unique composite hematolymphoid tumor consisting of a pro-T lymphoblastic lymphoma and an indeterminate dendritic cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Cahill et al., "450K-array analysis of chronic lymphocytic leukemia cells reveals global DNA methylation to be relatively stable over time and similar in resting and proliferative compartments," Leukemia, 27:150-158 (2013).
Cancer Genome Atlas Research Network, "Comprehensive molecular characterization of gastric adenocarcinoma," Nature, 513:202-209 (2014).
Carreno et al., "IL-12p70-producing patient DC vaccine elicits Tc1-polarized immunity," Journal of Clinical Investigation, 123(8):3383-94 (2013).
Carter et al., "Absolute quantification of somatic DNA alterations in human cancer," Nat Biotechnol, 30:413-21 (2012).
Carter et al., "Accurate estimation of homologue-specific DNA concentration-ratios in cancer samples allows long-range haplotyping," Nature Precedings, 59-87 (2011).
Caskey et al., "Synthetic double-stranded RNA induces innate immune responses similar to a live viral vaccine in humans," The Journal of experimental medicine, 208(12):2357-2366 (2011).
Castle et al., "Exploiting the mutanome for tumor vaccination," Cancer research, 72(5):1081-1091 (2012).
CBOL Plant Working Group, "A DNA barcode for land plants," PNAS, 106(31):12794-12797 (2009).
Chang et al., "Immune selection of hot-spot beta 2-microglobulin gene mutations, HLA-A2 allospecificity loss, and antigen-processing machinery component down-regulation in melanoma cells derived from recurrent metastases following immunotherapy." Journal of immunology, 174:1462-1471 (2005).

(56) References Cited

OTHER PUBLICATIONS

Chapman et al., "Initial genome sequencing and analysis of multiple myeloma," Nature, 471:467-472 (2011).
Cheever, "Twelve immunotherapy drugs that could cure cancers," Immunological reviews, 222:357-368 (2008).
Chen et al., "Impact of replication timing on non-CpG and CpG substitution rates in mammalian genomes," Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., "Molecular mechanisms of T cell co-stimulation and co-inhibition," Nature reviews Immunology, 13:227-242 (2013).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chen et al., "Induction of CD8+ T cell responses to dominant and subdominant epitopes and protective immunity to Sendai virus infection by DNA vaccination," The Journal of Immunology, 160(5):2425-2432 (1998).
Child et al., "Insertional inactivation of the large subunit of ribonucleotide reductase encoded by vaccinia virus is associated with reduced virulence in vivo," Virology, 174(2):625-629 (1990).
Chim et al., "Epigenetic dysregulation of the Wnt signalling pathway in chronic lymphocytic leukaemia," J Clin Pathol, 61:1214-1219 (2008).
Chiron et al., "Cell-cycle reprogramming for PI3K inhibition overrides a relapse-specific C4815 BTK mutation revealed by longitudinal functional genomics in mantle cell lymphoma," Cancer Discov, 4:1022-35 (2014).
Christian et al., "Targeting DNA double-strand breaks with TAL effector nucleases," Genetics, 186(2):757-761 (2010).
Chroboczek et al., "The Sequence of the Genome of Adenovirus Type 5 and Its Comparison with the Genome of Adenovirus Type 2," Virology, 186:280-285 (1992).
Church, "Genomes for all," Sci Am, 294(1):46-54 (2006).
Cibulskis et al., "ContEst: estimating cross-contamination of human samples in next-generation sequencing data," Bioinformatics, 27:2601-2602 (2011).
Cibulskis et al., "Sensitive detection of somatic point mutations in impure and heterogeneous cancer samples," Nat Biotechnol, 31:213-9 (2013).
Cleveland, "LOWESS: A program for smoothing scatterplots by robust locally weighted regression," The American Statistician, 35:54 (1981).
Conlon et al., "Mouse, but not Human STING, Binds and Signals in Response to the Vascular Disrupting Agent 5,6-Dimethylxanthenone-4- Acetic Acid," Journal of Immunology, 190:5216-25 (2013).
Corbett et al., "Aerosol immunization with NYVAC and MVA vectored vaccines is safe, simple, and immunogenic," Proc Natl Acad Sci, 105(6):2046-51 (2008).
Coulie et al., "A mutated intron sequence codes for an antigenic peptide recognized by cytolytic T lymphocytes on a human melanoma," Proc Natl Acad Sci USA, 92(17):7976-7980 (1995).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8α+ dendritic cells," Journal of Experimental Medicine, 207(6):1283-1292 (2010).
Daheshia et al., "Suppression of ongoing ocular inflammatory disease by topical administration of plasmid DNA encoding IL-10," The Journal of Immunology 159(4):1945-1952 (1997).
De et al., "Aberration in DNA methylation in B-cell lymphomas has a complex origin and increases with disease severity," PLoS Genet. 9:e1003137 (2013).
De Magalhaes et al., "Next-generation sequencing in aging research: emerging applications, problems, pitfalls and possible solutions," Ageing Research Reviews, 9(3):315-323 (2010).
DeLuca et al., "RNA-SeQC: RNA-seq metrics for quality control and process optimization," Bioinformatics, 28:1530-2 (2012).
DePristo et al., "A framework for variation discovery and genotyping using next-generation DNA sequencing data," Nature Genetics, 43:491-498 (2011).
Di Stasi et al.. "Inducible apoptosis as a safety switch for adoptive cell therapy," New England Journal of Medicine, 365(18):1673-1683 (2011).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Doody et al., "PRDMI/BLIMP-1 Modulates IFN—Dependent Control of the MHC Class I Antigen-Processing and Peptide-Loading Pathway," The Journal of Immunology, 179:7614-7623 (2007).
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dubey et al., "The immunodominant antigen of an ultraviolet-induced regressor tumor is generated by a somatic point mutation in the Dead (SEQ ID No. 62) box helicase p68," The Journal of experimental medicine, 185(4):695-705 (1997).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).
Earl et al., "Immunogenicity of a highly attenuated MVA smallpox vaccine and protection against monkeypox," Nature, 428:182 (2004).
Eckhardt et al., "DNA methylation profiling of human chromosomes 6, 20 and 22," Nat Genet, 38:1378-1385 (2006).
Eden et al., "Discovering motifs in ranked lists of DNA sequences," PLoS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).
Escobar et al., "Bayesian density estimation and inference using mixtures," Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Fais et al., "Chronic lymphocytic leukemia B cells express restricted sets of mutated and unmutated antigen receptors," The Journal of clinical investigation, 102:1515-25 (1998).
Fan et al., "The multi substrate adapter Gab1 regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Farsaci et al., "Consequence of dose scheduling of sunitinib on host immune response elements and vaccine combination therapy," Int J Cancer, 130:1948-1959 (2012).

(56) References Cited

OTHER PUBLICATIONS

Feigner et al., "Lipofection: A Highly Efficient, Lipid-Mediated DNA-Transfection Procedure," PNAS, 84(21): 7413-7417 (1987).
Ferrier-Rembert et al., "Short-and long-term immunogenicity and protection induced by non-replicating smallpox vaccine candidates in mice and comparison with the traditional 1st generation vaccine," Vaccine, 26(14):1794-1804 (2008).
Finke et al., "Sunitinib Reverses Type-1 Immune Suppression and Decreases T-Regulatory Cells in Renal Cell Carcinoma Patients," Clin Cancer Res, 14(20):6674-6682 (2008).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology, 143:532-6 (2008).
Fransen et al., "Controlled local delivery of CTLA-4 blocking antibody induces CD8+ T-cell-dependent tumor eradication and decreases risk of toxic side effects." Clin Cancer Res, 19(19):5381-5389 (2013).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., "Inhibition of Syk with fostamatinib disodium has significant clinical activity in non-Hodgkin lymphoma and chronic lymphocytic leukemia," Blood, 115:2578-2585 (2011).
Fritsch et al., "Translational repression of MCL-1 couples stress-induced eIF2 alpha phosphorylation to mitochondrial apoptosis initiation," The Journal of biological chemistry, 282:22551-62 (2007).
Furman et al., "Idelalisib and rituximab in relapsed chronic lymphocytic leukemia," The New England journal of medicine, 370:997-1007 (2014).
Fynan et al., "DNA vaccines: protective immunizations by parenteral, mucosal, and gene-gun inoculations," PNAS, 90 (24): 11478-82 (1993).
Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the'cancer vaccine' haystack," Nature medicine, 16(8):854-856 (2010).
Gao et al., "Integrative analysis of complex cancer genomics and clinical profiles using the cBioPortal," Science signaling, 6(269):pi1 (2013).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).
Garraway et al., "Lessons from the cancer genome," Cell, 153:17-37 (2013).
Gaucher et al., "Yellow fever vaccine induces integrated multilineage and polyfunctional immune responses," The Journal of experimental medicine, 205(13):3119-3131 (2008).
Gevaert et al., "Protein identification methods in proteomics," Electrophoresis: An International Journal, 21 (6):1145-1154 (2000).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., "Functional profiling of the *Saccharomyces cerevisiae* genome," Nature, 418(6896):387-391 (2002).
Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gibbs et al., "Abundant quantitative trait loci exist for DNA methylation and gene expression in human brain," PLoS genetics, 6:e1000952 (2010).
Gluzman, "SV40-transformed simian cells support the replication of early SV40 mutants," Cell, 23:175-182(1981).
Goebel et al., "The complete DNA sequence of vaccinia virus." Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1 BX08 gp120 and HIV-1IIIB Gag-Pol-Nef proteins of clade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice." Journal of General Virology, 88(9):2473-2478 (2007).
Greco et al., "Improving the safety of cell therapy with the TK-suicide gene," Front Pharmacol, 6:95 (2015).
Gregoriadis et al., "Improving the therapeutic efficacy of peptides and proteins: A role for polysialic acids," Int J Pharmaceutics, 300(1-2):125-30 (2005).
Gros et al., "PD-1 identifies the patient-specific CD8+ tumor-reactive repertoire infiltrating human tumors," The Journal of clinical investigation, 124(5):2246-2259 (2014).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guo et al., "Droplet microfluidics for high-throughput biological assays," Lab Chip, 12:2146-55 (2012).
Guthals et al., "Shotgun Protein Sequencing with Meta-contig Assembly," Molecular and Cellular Proteomics, 1(10):1084-96 (2012).
Hadrup et al., "Parallel detection of antigen-specific T-eeil responses by multidimensional encoding of MHC multimers," Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).
Hall, "Advanced sequencing technologies and their wider impact in microbiology," Journal of experimental biology, 210(9):1518-1525 (2007).
Hanahan et al., "Hallmarks of cancer: the next generation," Cell, 144:646-674 (2011).
Hansen et al., "Increased methylation variation in epigenetic domains across cancer types," Nat Genet, 43:768-775 (2011).

(56) References Cited

OTHER PUBLICATIONS

Hanzelmann et al., "GSVA: gene set variation analysis for microarray and RNA-Seq data," BMC bioinformatics, 14:7 (2013).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBECI and some of its homologs can act as DNA mutators," Molecular cell, 1095):1247-1253 (2002).
Heemskerk et al., "The cancer antigenome," EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., "HAART reduces death ligand but not death receptors in lymphoid tissue of HIV-infected patients and simian immunodeficiency virus-infected macaques." AIDS, 23:35-40 (2009).
Herman et al., "ibrutinib-induced lymphocytosis in patients with chronic lymphocytic leukemia: correlative analyses from a phase II study," Leukemia, 28:2188 (2014).
Hinrichs et al., "Exploiting the curative potential of adoptive T-cell therapy for cancer," Immunological reviews, 257:56-71 (2014).
Hombrink et al., "High-Throughput Identification of Potential Minor Histocompatibility Antigens by MHC Tetramer-Based Screening: Feasibility and Limitations," Pios One, 6(8):1-11 (2011).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Horig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Hutchings et al., "Combination of protein and viral vaccines induces potent cellular and humoral immune responses and enhanced protection from murine malaria challenge," Infect Immun, 75(12):5819-26 (2007).
Illingworth et al., "Orphan CpG islands identify numerous conserved promoters in the mammalian genome," PLoS Genet, 6(9):e1001134 (2010).
Inokuchi et al., "DCC protein expression in hematopoietic cell populations and its relation to leukemogenesis," J Clin Invest, 97:852-857 (1996).
Itoh et al.. "Personalized peptide vaccines: A new therapeutic modality for cancer," Cancer Sci, 97:970-976 (2006).
Izeradjene et al., "Casein kinase II (CK2) enhances death-inducing signaling complex (DISC) activity in TRAIL-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).
Jensen et al., "Design and implementation of adoptive therapy with chimeric antigen receptor-modified T cells," Immunol Rev, 257(1):127-144 (2014).
Johann et al., "GLVR1, a receptor for gibbon ape leukemia virus, is homologous to a phosphate permease of Neurospora crassa and is expressed at high levels in the brain and thymus," Journal of Virology, 66(3):1635-1640 (1992).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Kandoth et al., "Mutational landscape and significance across 12 major cancer types," Nature, 502:333-339 (2013).
Kannan et al.. "Vaccination strategies in follicular lymphoma," Current hematologic malignancy reports, 4(4):189-195 (2009).
Kantoff et al. "Overall survival analysis of a phase II randomized controlled trial of a Poxviralbased PSA-targeted immunotherapy in metastatic castration-resistant prostate cancer," Journal of Clinical Oncology, 28(7):1099-1105 (2010).
Karanikas et al., "High frequency of cytolytic T lymphocytes directed against a tumor-specific mutated antigen detectable with HLA tetramers in the blood of a lung carcinoma patient with long survival," Cancer Res. 61:3718-3724 (2001).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kaufman et al., "Phase II randomized study of vaccine treatment of advanced prostate cancer (E7897): a trial of the Eastern Cooperative Oncology Group," Journal of Clinical Oncology, 22(11):2122-2132 (2004).
Kawai et al., "TLR signaling," Seminars in immunology, 19(1):24-32 (2007).
Kenter et al., "Vaccination against HPV-16 oncoproteins for vulvar intraepithelial neoplasia," New England Journal of Medicine, 361 (19):1838-1847 (2009).
Khong et al., "Natural selection of tumor variants in the generation of "tumor escape" phenotypes," Nature immunology, 3:999-1005 (2002).
Kim et al., "A Myc network accounts for similarities between embryonic stem and cancer cell transcription programs," Cell, 143:313-324 (2010).
Kim et al., "Anticancer flavonoids are mouse-selective STING agonists," ACS chemical biology, 8(7):1396-1401 (2013).
Kim et al., "TopHat2: accurate alignment of transcriptomes in the presence of insertions, deletions and gene fusions," Genome biology, 14:R36 (2013).
Kim et al., "TroVax, a recombinant modified vaccinia Ankara virus encoding 5T4: lessons learned and future development," Human vaccines, 6(10):784-791 (2010).
Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in Highisk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klebanoff et al., "Therapeutic cancer vaccines:are we there yet?," Immunol Rev, 239(1):27-44 (2011).
Klein et al., "Droplet Barcoding for Single-Cell Transcriptomics Applied to Embryonic Stem Cells," Cell, 161:1187-1201 (2015).
Kloor et al., "Immune evasion of microsatellite unstable colorectal cancers," International journal of cancer, 127:1001-1010 (2010).
Kobayashi et al., "Peptide epitope identification for tumor-reactive CD4 T cells," Current opinion in immunology, 20(2):221-227 (2008).
Koch, "Combining morphology and DNA barcoding resolves the taxonomy of Western Malagasy Liotrigona Moure, 1961," African Invertebrates, 51(2):413-421 (2010).
Kotwal et al., "Vaccinia virus encodes two proteins that are structurally related to members of the plasma serine protease inhibitor superfamily," Journal of virology, 63(2):600-606 (1989).

(56) References Cited

OTHER PUBLICATIONS

Kreiter et al., "Mutant MHC Class II epitopes drive therapeutic immune responses to cancer," Nature, 520:692 (2015).
Kreso et al., "Variable clonal repopulation dynamics influence chemotherapy response in colorectal cancer," Science, 339:543-548 (2013).
Kress et al., "DNA barcodes: Genes, genomics, and bioinformatics," PNAS, 105(8):2761-2762 (2008).
Kress et al.. "Use of DNA barcodes to identify flowering plants," PNAS, 102(23):8369-8374 (2005).
Kulis et al., "Epigenomic analysis detects widespread gene-body DNA hypomethylation in chronic lymphocytic leukemia," Nat Genet, 44:1236-1242 (2012).
Kyte et al., "Telomerase Peptide Vaccination Combined with Temozolomide: A Clinical Trial in Stage IV Melanoma Patients," Clin Cancer Res, 17(13):4568-4580 (2011).
Lahaye et al., "DNA barcoding the floras of biodiversity hotspots," PNAS, 105(8):2923-2928 (2008).
Landan et al., "Epigenetic polymorphism and the stochastic formation of differentially methylated regions in normal and cancerous tissues," Nat Genet, 44:1207-1214 (2012).
Landau et al., "Clonal evolution in hematological malignancies and therapeutic implications," Leukemia, 28:34-43 (2014).
Landau et al., "Evolution and Impact of Subclonal Mutations in Chronic Lymphocytic Leukemia," Cell, 152:714-726 (2013).
Langmead et al., "Fast gapped-read alignment with Bowtie 2," Nat Meth, 9:357-359 (2012).
Langmead et al., "Ultrafast and memory-efficient alignment of short DNA sequences to the human genome," Genome Biology, 10:R25 (2009).
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Le Mercier et al., "Beyond CTLA-4 and PD-1, the generation Z of negative checkpoint regulators," Front Immunol, 6:418 (2015).
Lee et al., "Sequential amplification of cloned DNA as tandem multimers using class-IIS restriction enzymes," Genetic Analysis: Biomolecular Engineering, 13(6):139-145 (1996).
Leffers et al., "Immunization with a P53 synthetic long peptide vaccine induces P53☐specific immune responses in ovarian cancer patients, a phase II trial," Int J Cancer, 125(9):2104-2113 (2009).
Leffers et al., "Long-term clinical and immunological effects of p53?SLP® vaccine in patients with ovarian cancer," Int J Cancer, 130(1):105-112 (2012).
Leitner et al., "Immune responses induced by intramuscular or gene gun injection of protective deoxyribonucleic acid vaccines that express the circumsporozoite protein from *Plasmodium berghei* malaria parasites," J Immunol, 159(12):6112-6119 (1997).
Lemay et al., "Dok-3, a Novel Adapter Molecule Involved in the Negative Regulation of Immunoreceptor Signaling," Mol Cell Biol, 20:2743-2754 (2000).
Lennerz et al., "The Response of Autologous T Cells to a Human Melanoma is Dominated by Mutated Neoantigens," PNAS, 102(44):16013-16018 (2005).
Lewis et al., "DNA Vaccines: A Review," Advances in Virus Research, 54:129-88 (1999).
Li et al., "Fast and accurate short read alignment with Burrows-Wheeler Transform," Bioinformatics, 25(14):1754-1760 (2009).
Li et al., "Inactivating mutations of the chromatin remodeling gene ARID2 in hepatocellular carcinoma," Nature Genetics, 43:828-829 (2011).
Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics, 12:323 (2011).
Li et al., "The Sequence Alignment/Map format and SAMtools," Bioinformatics, 25(16):2078-2079 (2009).
Li et al.,"Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Link et al., "Electric control of droplets in microfluidic devices," Angew Chern Int Ed Engl, 45(16):2556-2560 (2006).
Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1)71-79 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lu et al., "Mutated regions of nucleophosmin 1PPP1R3B Is Recognized by T Cells Used To Treat a Melanoma Patient Who Experienced a Durable Complete Tumor Regression," J Immunol, 190(12):6034-6042 (2013).
Luckow et al., "Trends in the Development of Baculovirus Expression Vectors," Nat Biotechnol, 6:47-55(1988).
Lund et al., "Coordination of early protective immunity to viral infection by regulatory T cells," Science, 320(5880):1220-1224 (2008).
Lundegaard et al., "Prediction of epitopes using neural network based methods," J Immunol Methods, 374( 1-2):26-34 (2011).
Mackett et al., "Vaccinia virus: a selectable eukaryotic cloning and expression vector," PNAS, 79:7415-7419 (1982).
Macosko et al., "Highly Parallel Genome-wide Expression Profiling of Individual Cells Using Nanoliter Droplets," Cell, 161(5):1202-1214 (2015).
Maegawa et al., "Age-related epigenetic drift in the pathogenesis of MDS and AML." Genome Res, 24:580-591 (2014).
Mandl et al., "Immunotherapy with MVA-BN®-HER2 induces HER-2-specific Th1 immunity and alters the intratumoral balance of effector and regulatory T cells," Cancer Immunol Immunother, 61(1):19-29 (2012).
Manghera et al., "Endogenous retrovirus-K promoter: a landing strip for inflammatory transcription factors?," Retrovirol, 10:16 (2013).
Mannino et al., "Liposome Mediated Gene Transfer," Biotechniques, 6(7): 682-690 (1988).
Marabelle et al., "Depleting tumor-specific Tregs at a single site eradicates disseminated tumors," J Clin Invest, 1123(6):2447-2463(2013).
Maratea et al. "Deletion and fusion analysis of the phage φX174 lysis gene E," Gene 40(1):39-46(1985).
Marcais et al., "A fast, lock-free approach for efficient parallel counting of occurrences of k-mers," Bioinformatics, 27(6):764-770 (2011).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Matsushita et al., "Cancer Exome Analysis Reveals a T Cell Dependent Mechanism of Cancer Immunoediting," Nature, 482(7385):400-404 (2012).
Maus et al., "Adoptive Immunotherapy for Cancer or Viruses," Annual Review of Immunology, 32:189-225 (2014).

(56) References Cited

OTHER PUBLICATIONS

Mayer et al., "A revised nomenclature for transcribed human endogenous retroviral loci," Mobile DNA, 2:7 (2011).
Mayr et al., "Abstammung, Eigenschaften und Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
Mazutis et al., "Single-cell analysis and sorting using droplet-based microfluidics," Nat Protoc, 8:870-891 (2013).
McCormack et al., "HLA-A*3101 and Carbamazepine-Induced Hypersensitivity Reactions in Europeans," New Engl J Med, 364:1134-1143 (2011).
McCurdy et al., "Modified Vaccinia Ankara: Potential as an Alternative Smallpox Vaccine," Clin Infect Dis, 38:1749-1753 (2004).
McDermott et al., "Immune Therapy for Kidney Cancer: A Second Dawn?," Semin Oncol, 40(4):492-498 (2013).
McFadden et al., "Genetic and clonal dissection of murine small cell lung carcinoma progression by genome sequencing," Cell, 156(6):1298-1311 (2014).
McKenna et al., "The Genome Analysis Toolkit: a MapReduce framework for analyzing next-generation DNA sequencing data," Genome Res, 20(9):1297-1303 (2010).
Medema et al.. "Immune Escape of Tumors in Vivo by Expression of Cellular Flice-Inhibitory Protein," J Exp Med, 190:1033-1038 (1999).
Meissner et al., "Genome-scale DNA methylation maps of pluripotent and differentiated cells," Nature, 454:766-770 (2008).
Melief et al., "Immunotherapy of established (pre)malignant disease by synthetic long peptide vaccines," Nature Rev Cancer, 8:351-360 (2008).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic copy-number alteration in human cancers," Genome Biol, 12:R41 (2011).
Merrifield, "Solid Phase Peptide Synthesis. I. The Synthesis of a Tetrapeptide," J Am Chem Soc, 85(14):2149-2154 (1963).
Messmer et al., "In vivo measurements document the dynamic cellular kinetics of chronic lymphocytic leukemia B cells," J Clin Invest, 115(3):755-764 (2005).
Meyer et al., "Mapping of deletions in the genome of the highly attenuated vaccinia virus MVA and their influence on virulence," J Gen Virol, 72:1031-1038 (1991).
Midgley, "Vaccinia virus strain NYVAC induces substantially lower and qualitatively different human antibody responses compared with strains Lister and Dryvax," J Gen Virol, 89:2992-2997 (2008).
Miller et al., "Construction and properties of retrovirus packaging cells based on gibbon ape leukemia virus," Virol, 65:2220-2224 (1991).
Missale et al., "HLA-A31- and HLA-Aw68-restricted cytotoxic T cell responses to a single hepatitis B virus nucleocapsid epitope during acute viral hepatitis," J Exp Med. 177(3):751-762 (1993).
Mocellin et al., "Interferon Alpha Adjuvant Therapy in Patients With High-Risk Melanoma: A Systematic Review and Meta-analysis," JNCI, 102(7):493-501 (2010).
Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).
Mor et al., "Complexity of the cytokine and antibody response elicited by immunizing mice with Plasmodium yoelii circumsporozoite protein plasmid DNA," J Immunol, 155(4):2039-2046 (1995).
Morison et al., "A census of mammalian imprinting," Trends Genet, 21(8):457-465 (2005).
Morozov et al., "The Transmembrane Protein of the Human Endogenous Retrovirus—K (HERV-K) Modulates Cytokine Release and Gene Expression," PloS one 8(8):e70399 (2013).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Moss, "Reflections on the early development of poxvirus vectors," Vaccine, 31 (39): 4220-4222 (2013).
Murphy et al., "Genetic construction, expression, and melanoma-selective cytotoxicity of a diphtheria toxin-related alpha-melanocyte-stimulating hormone fusion protein," PNAS, 83:8258-8262 (1986).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Nielsen et al., "NetMHCpan, a Method for Quantitative Predictions of Peptide Binding to Any HLA-A and -B Locus Protein of Known Sequence," PloS one, 2:0796 (2007).
Nishimura et al., "Distinct Role of Antigen-Specific T Helper Type 1 (Th 1) and Th2 Cells in Tumor Eradication in Vivo," J Ex Med, 190(5):617-27 (1999).
Nocentini et al., "A new member of the tumor necrosis factor/nerve growth factor receptor family inhibits T cell receptor-induced apoptosis," PNAS, 94(12):6216-6221 (1997).
Novershtern et al., "Densely Interconnected Transcriptional Circuits Control Cell States in Human Hematopoiesis," Cell, 144(2):296-309 (2011).
Oh et al., "Neutrophil isolation protocol," J Vis Exp (2008).
Ohnishi et al., "Premature Termination of Reprogramming In Vivo Leads to Cancer Development through Altered Epigenetic Regulation," Cell, 156(4):663-677 (2014).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Oshiumi et al., "DEAD/H BOX 3 (DDX3) helicase binds the RIG-I adaptor IPS-1 to up-regulate IFN-beta-inducing potential," Eur J Immunol, 40:940-948 (2010).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Oudard et al., "A phase II study of the cancer vaccine TG4010 alone and in combination with cytokines in patients with metastatic renal clear-cell carcinoma: clinical and immunological findings," Cancer Immunol Immunother, 60(2): 261-271 (2011).
Padgett et al., "Creating seamless junctions independent of restriction sites in PCR cloning," Gene, 168:31-35 (1996).
Page et al., "Immune Modulation in Cancer with Antibodies," Annu Rev Med, 65:185-202 (2014).
Pages, et al., "Effector Memory T Cells, Early Metastasis, and Survival in Colorectal Cancer," New Engl J Med, 353:2654-2666 (2005).
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," PNAS, 79(16):4927-4931 (1982).
Pantaleo et al., "Poxvirus vector-based HIV vaccines," Curr Opin HIV-AIDS, 5:391-396 (2010).

(56) References Cited

OTHER PUBLICATIONS

Paoletti, "Applications of pox virus vectors to vaccination: an update," PNAS, 93(21):11349-53 (1996).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance," PloS one 7:e39967 (2012).
Perez et al., "A new era in anticancer peptide vaccines," Cancer, 116(9):2071-2080 (2010).
Perez et al., "p63 consensus DNA-binding site: identification, analysis and application into a p63MH algorithm," Oncogene, 26:7363-7370 (2007).
Perkvs et al., "Poxvirus based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Petsch et al., "Protective efficacy of in vitro synthesized, specific mRNA vaccines against influenza A virus infection," Nat Biotechnol, 30(12):1210-1216 (2012).
Pieters et al., "On guard: coronin proteins in innate and adaptive immunity," Nat Rev Immunol, 13:510-518 (2013).
Pirard et al., "Interferon Alpha as Adjuvant Postsurgical Treatment of Melanoma: A Meta-Analysis," Dermatology, 208(1):43-48 (2004).
Poirot et al., "Multiplex genome edited T-cell manufacturing platform for "off-the-shelf" adoptive T-cell immunotherapies," Cancer Res, 75(18):3853 (2015).
Poulet, "Development and registration of recombinant veterinary vaccines: The example of the canarypox vector platform," Vaccine, 25(30):5606-5612 (2007).
Powell et al., "NCoR1 Mediates Papillomavirus E8E2C Transcriptional Repression," J Virol, 84:4451-4460 (2010).
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al.,"CTLA4 blockade and GM-CSF combination immunotherapy alters the intratumor balance of effector and regulatory T cells," J Clin Invest, 116(7):1935-1945 (2006).
Ramos et al., "An Inducible Caspase 9 Suicide Gene to Improve the Safety of Mesenchymal Stromal Cell Therapies," Stem Cells, 28(6):1107-1115 (2010).
Ramskold et al., "Full-length mRNA-Seq from single-cell levels of RNA and individual circulating tumor cells," Nat Biotechnol, 30:777-782 (2012).
Rassenti et al., "Relative value of ZAP-70, CD38, and immunoglobulin mutation status in predicting aggressive disease in chronic lymphocytic leukemia," Blood, 112:1923-1930 (2008).
Raval et al., "Downregulation of Death-Associated Protein Kinase 1 (DAPK1) in Chronic Lymphocytic Leukemia," Cell, 129(5):879-890 (2007).
Ravi et al., "Sensitization of Tumor Cells to Apo2 Ligand/TRAIL-induced Apoptosis by Inhibition of Casein Kinase II," Cancer Res, 62(15):4180-4185 (2002).
Richter et al., "Mechanistic Determinants of Biotherapeutics Absorption Following SC Administration," The AAPS Journal, 14(3):559-568 (2012).
Rini et al., "Biology and Treatment of Advanced Renal Cell Carcinoma: A Global Perspective," Semin Oncol, 40(4):419-420 (2013).
Robbins et al., "Mining exomic sequencing data to identify mutated antigens recognized by adoptively transferred tumor-reactive T cells," Nat Med, 19(6)747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Robinson et al., "DNA vaccines for viral infections: Basic studies and applications," Adv Virus Res, 55:1-74(2000).
Robinson et al., "edgeR: a Bioconductor package for differential expression analysis of digital gene expression data," Bioinformatics, 26(1):139-140 (2010).
Robinson et al., "Integrative genomics viewer," Nat Biotechnol, 29:24-26 (2011).
Rolph et al., "Recombinant viruses as vaccines and immunological tools," Curr Opin Immunol, 9(4):517-524 (1997).
Ronchetti et al., "Frontline:GITR, a member of the TNF receptor superfamily,is costimulatory to mouse T lymphocytesubpopulations," Eur J Immunol, 34(3):613-622 (2004).
Rosenberg et al., "Adoptive cell transfer as personalized immunotherapy for human cancer," Science, 348(6230):62-68 (2015).
Rosenberg, "Raising the Bar: The Curative Potential of Human Cancer Immunotherapy," Sci Transl Med, 4(127):127ps128 (2012).
Rossi et al., "Integrated mutational and cytogenetic analysis identifies new prognostic subgroups in chronic lymphocytic leukemia," Blood, 121:1403-1412 (2013).
Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).
Rupprecht et al., "Oral immunization and protection of raccoons (Procyon lotor) with a vaccinia-rabies glycoprotein recombinant virus vaccine," PNAS, 83:7947-7950 (1986).
Rutledge et al., "Tumor-Infiltrating Lymphocytes in Glioblastoma Are Associated with Specific Genomic Alterations and Related to Transcriptional Class," Clin Cancer Res, 19:4951-4960 (2013).
Sabado et al., "Preparation of Tumor Antigen-loaded Mature Dendritic Cells for Immunotherapy," J Vis Exp, 78:50085 (2013).
Sadelain, "Eliminating Cells Gone Astray," New Engl J Med, 365:1735-1737 (2011).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity," J Immunother, 28(3):220-228 (2005).
Sampson et al., "An epidermal growth receptor variant III-targeted vaccine is safe and immunogenic in patients with glioblastomas multiforme," Mol Cancer Ther, 8(10):2773-2779 (2009).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).
Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Samuels et al., "Oncogenic PI3K and its role in cancer," Curr Opin Oncol, 18:77-82n (2006).
Sancho, "The Block in Assembly of Modified Vaccinia Virus Ankara in HeLa Cells Reveals New Insights into Vaccinia Virus Morphogenesis," J Virol, 76(16):8313-8334 (2002).
Sato et al., "Discovery of Novel Targets for Aberrant Methylation in Pancreatic Carcinoma Using High-Throughput Microarrays," Cancer Res, 63(13):3735-3742 (2003).
Saturno et al., "Combining TRAIL with PI3 Kinase or HSP90 inhibitors enhances apoptosis in colorectal cancer cells via suppression of survival signaling," Oncotarget, 4(8):1185-1198 (2013).
Saunders et al., "Strelka: accurate somatic small-variant calling from sequenced tumor-normal sample pairs," Bioinformatics, 28(14):1811-1817 (2012).
Schmitt et al., "Transcriptional Profiling of Human Endogenous Retrovirus Group HERV-K(HML-2) Loci in Melanoma," Genome Biol Evol, 5(2):307-328 (2013).
Schneider et al, "Induction of CD8+ T cells using heterologous prime-boost immunisation strategies," Immunol Rev, 170(1):29-38 (1999).
Schreiber et al., "Cancer Immunoediting: Integrating Immunity's Roles in Cancer Suppression and Promotion," Science, 331 (6024):1565-1570 (2011).

(56) References Cited

OTHER PUBLICATIONS

Schumacher et al., "Prognostic Significance of Activated CD8+ T Cell Infiltrations within Esophageal Carcinomas," Cancer Res, 61(10):3932-3936 (2001).
Schuster et al., "Vaccination With Patient-Specific Tumor-Derived Antigen in First Remission Improves Disease-Free Survival in Follicular Lymphoma." J Clin Oncol, 29(20):2787-2794 (2011).
Scriba et al., "Modified vaccinia Ankara expressing Ag85A, a novel tuberculosis vaccine, is safe in adolescents and children, and induces polyfunctional CD4+ T cells," Eur J Immunol, 40(1):279-290 (2010).
Seberg et al., "How Many Loci Does it Take to DNA Barcode a Crocus?," PLoS One 4(2):e4598 (2009).
Secchiero et al., "Aberrant expression of TRAIL in B chronic lymphocytic leukemia (B-CLL) cells," J Cell Physiol, 205(2):246-252 (2005).
Sedegah et al., "Protection against malaria by immunization with plasmid DNA encoding circumsporozoite protein," PNAS, 91(21):9866-9870 (1994).
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).
Shalek et al., "Single-cell RNA-seq reveals dynamic paracrine control of cellular variation." Nature, 510(7505):363-369 (2014).
Shannon, "A Mathematical Theory of Communication," Bell System Technical Journal, 27(3):379-423 (1948).
Shao et al., "Clonally related histiocytic/dendritic cell sarcoma and chronic lymphocytic leukemia/small lymphocytic lymphoma: a study of seven cases," Mod Pathol, 24:1421-1432 (2011).
Sharei et al., "Ex Vivo Cytosolic Delivery of Functional Macromolecules to Immune Cells," Plos One, 10(4):e0118803 (2015).
Shida, "Effects and virulences of recombinant vaccinia viruses derived from attenuated strains that express the human T-cell leukemia virus type I envelope gene," J Virol, 62(12):4474-4480 (1988).
Shipony et al., "Dynamic and static maintenance of epigenetic memory in pluripotent and somatic cells," Nature, 513:115-119 (2014).
Sidney et al., "HLA class I supertypes: a revised and updated classification," BMC Immunol, 9:1 (2008).
Siegel et al., "Cancer statistics, 2013," CA, 63(1):11-30 (2013).
Simmons et al., "Local secretion of anti-CTLA-4 enhances the therapeutic efficacy of a cancer immunotherapy with reduced evidence of systemic autoimmunity," Cancer Immunol Immunother, 57(8):1263-1270 (2008).
Simpson et al., "Cancer/testis antigens, gametogenesis and cancer," Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Sizemore, "Attenuated Shigella as a DNA Delivery Vehicle for DNA-Mediated Immunization," Science, 270(5234):299-303 (1995).
Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).
Slingluff et al., "Randomized Multicenter Trial of the Effects of Melanoma-Associated Helper Peptides and Cyclophosphamide on the Immunogenicity of a Multipeptide Melanoma Vaccine," J Clin Oncol, 29(21):2924-2932 (2011).
Smith et al., "Comparison of biosequences," Adv Appl Math, 2(4):482-489 (1981).
Smith et al., "Construction and characterization of an infectious vaccinia virus recombinant that expresses the influenza hemagglutinin gene and induces resistance to influenza virus infection in hamsters," PNAS, 80(23)7155-7159 (1983).
Smith et al. "Infectious vaccinia virus recombinants that express hepatitis B virus surface antigen," Nature, 302:490-495 (1983).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Soares et al. "A subset of dendritic cells induces CD4+ T cells to produce IFN-gamma by an IL-12-independent but CD70-dependent mechanism in vivo," J Exp Med, 2215(11):1095-1106 (2007).
Soininen et al., "Analysing diet of small herbivores: the efficiency of DNA barcoding coupled with high-throughput pyrosequencing for deciphering the composition of complex plant mixtures," Front Zool, 6:16 (2009).
Sommnerfeit et al., "Receptor interference groups of 20 retroviruses plating on human cells," Virol, 176:58-59 (1990).
Song et al., "c-Cbl acts as a mediator of Src-induced activation of the PI3K-Akt signal transduction pathway during TRAIL treatment," Cellular Signalling, 22(3):377-385 (2010).
Sosman et al., "A phase 2 trial of complete resection for stage IV melanoma: results of Southwest Oncology Group Clinical Trial S9430," Cancer, 117(20):4740-4706 (2011).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Speiser et al., "Molecularly defined vaccines for cancer immunotherapy, and protective T cell immunity," Semin Immunol, 22(3):144-154 (2010).
Spencer et al., "Non-genetic origins of cell-to-cell variability in TRAIL-induced apoptosis," Nature, 459:428-432 (2009).
Spranger et al., "Up-regulation of PD-LI, IDO, and Tregs in the melanoma tumor microenvironment is driven by CD8+ T cells," Sci Transl Med, 5(200):200ra116 (2013).
Staehler et al., "An open label study to evaluate the safety and immunogenicity of the peptide based cancer vaccine IMA901," ASCO meeting 2007; Abstract No. 3017.
Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stover et al., "New Use of BCG for Recombinant Vaccines," Nature, 351 (6326): 456-460 (1991).
Stransky et al., "The Mutational Landscape of Head and Neck Squamous Cell Carcinoma," Science, 333:1157-1160 (2011).
Subramanian et al., "Gene set enrichment analysis: a knowledge-based approach for interpreting genome-wide expression profiles," PNAS, 102:15545-15550 (2005).
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Tang et al., "The landscape of viral expression and host gene fusion and adaptation in human cancer," Nat Commun, 4:2513 (2013).
Tartaglia et al., "NYVAC: A highly attenuated strain of vaccinia virus," Virology, 188(1):217-232 (1992).
Ten Bosch et al., "Keeping Up With the Next Generation: Massively Parallel Sequencing in Clinical Diagnostics," J Mol Diagn, 10(6):484-492 (2008).
Teng et al., "A human TAPBP (TAPASIN)-related gene, TAPBP-R," Eur J Immunol, 32:1059-1068 (2002).
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).

(56) References Cited

OTHER PUBLICATIONS

Timp et al., "Cancer as a dysregulated epigenome allowing cellular growth advantage at the expense of the host," Nat Rev Cancer, 13:497-510 (2013).
Tjoa et al., "Follow-Up Evaluation of Prostate Cancer Patients Infused with Autologous Dendritic Cells Pulsed with PSMA Peptides," Prostate, 32(4): 272-278 (1997).
Topalian et al., "Safety, Activity, and Immune Correlates of Anti-PD-1 Antibody in Cancer," N Engl J Med, 366(26):2443-2454 (2012).
Topalian et al., "Survival, Durable Tumor Remission, and Long-Term Safety in Patients With Advanced Melanoma Receiving Nivolumab," J Clin Oncol, 32(10):1020-1030 (2014).
Tough et al., "Induction of bystander T cell proliferation by viruses and type I interferon in vivo," Science, 272(5270):1947-1950 (1996).
Tran et al., "Cancer Immunotherapy Based on Mutation-Specific CD4+ T Cells in a Patient with Epithelial Cancer," Science, 344(6184):641-645 (2014).
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ T cell immunity together with a dendritic cell targeted vaccine," PNAS, 105(7):2574-2579 (2008).
Tucker et al., "Massively Parallel Sequencing: The Next Big Thing in Genetic Medicine," Am J Hum Genet, 85(2):142-154 (2009).
Uderhardt et al., "12/15-lipoxygenase orchestrates the clearance of apoptotic cells and maintains immunologic tolerance," Immunity, 36(5):834-846 (2012).
Ushijima et al., "Fidelity of the methylation pattern and its variation in the genome," Genome research, 13:868-874 (2005).
Uyttenhove et al., "Evidence for a tumoral immune resistance mechanism based on tryptophan degradation by indoleamine 2,3-dioxygenase," Nature medicine, 9:1269-1274 (2003).
Vaishampayan et al., "Active immunotherapy of metastatic melanoma with allogeneic melanoma lysates and interferon alpha," Clin Cancer Res, 8(12):3696-3701 (2002).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).
Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor Exome Analysis Reveals Neoantigen-Specific T-Cell Reactivity in an Ipilimumab- Responsive Melanoma," Journal of Clinical Oncology, 31(32):e439-e442 (2013).
Verardi et al., "A vaccinia virus renaissance: new vaccine and immunotherapeutic uses after smallpox eradication," Human vaccines & immunotherapeutics, 8(7):961-970 (2012).
Vermeij et al., "Potentiation of a p53-SLP vaccine by cyclophosphamide in ovarian cancer: a single-arm phase II study," Int J Cancer, 131(5):E670-680 (2012).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
Von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Wahl et al., "[43] Molecular hybridization of immobilized nucleic acids: Theoretical concepts and practical considerations," Methods in enzymology, Academic Press, 152:399-407 (1987).
Walter et al., "Multipeptide immune response to cancer vaccine IMA901 after single-dose cyclophosphamide associates with longer patient survival," Nature medicine, 18(8):1254 (2012).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Watson et al., "SHP-1: the next checkpoint target for cancer immunotherapy?," Biochem Soc Trans, 44(2):356-362 (2016).
Weber et al., "Assembly of Designer TAL Effectors by Golden Gate Cloning." PLoS ONE, 6:e19722 (2001).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies-a review," Vaccine, 27(51):7198-7201 (2009).
Wheatley et al., "Does adjuvant interferon-alpha for high-risk melanoma provide a worthwhile benefit?A meta-analysis of the randomised trials," Cancer treatment reviews, 29(4):241-252 (2003).
Whelan et al., "Safety and immunogenicity of boosting BCG vaccinated subjects with BCG: comparison with boosting with a newTB vaccine, MVA85A," PLoS One, 4(6):e5934 (2009).
Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Wiktor et al., "Protection from rabies by a vaccinia virus recombinant containing the rabies virus glycoprotein gene," Proceedings of the National Academy of Sciences, 81(22):7194-7198 (1984).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Winzeler et al., "Functional characterization of the S. cerevisiae genome by gene deletion and parallel analysis," science, 285(5429):901-906 (1999).
Wolchok et al., "Nivolumab plus ipilimumab in advanced melanoma," N Engl J Med, 369(2):122-133 (2013).
Wolff et al., "Direct Gene Transfer into Mouse Muslce in Vivo," Science, 247(4949):1465-1468 (1990).
Wong et al., "Module map of stem cell genes guides creation of epithelial cancer stem cells," Cell Stem Cell. 2:333-344 (2008).
Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Wyatt et al. "Marker rescue of the host range restriction defects of modified vaccinia virus Ankara," Virology, 251(2):334-342 (1998).
Wyatt et al., "Multiprotein HIV type 1 clade B DNA and MVA vaccines: construction, expression, and immunogenicity in rodents of the MVA component," AIDS research and human retroviruses, 20(6):645-653 (2004).
Xi et al., "BSMAP: whole genome bisulfite sequence MAPping program," BMC bioinformatics, 10:232 (2009).

(56) References Cited

OTHER PUBLICATIONS

Xie et al., "Stepwise reprogramming of B cells into macrophages," Cell, 117(5):663-676 (2004).
Xu et al., "Design of 240,000 orthogonal 25mer DNA barcode probes," Proceedings of the National Academy of Sciences, pnas-0812506106 (2009).
Yan et al., "PBAF chromatin-remodeling complex requires a novel specificity subunit, BAF200, to regulate expression of selective interferon-responsive genes," Genes & development, 19(14):1662-1667 (2005).
Yang et al. "CML66, a broadly immunogenic tumor antigen, elicits a humoral immune response associated with remission of chronic myelogenous leukemia," PNAS, 98(13):7492-7497 (2001).
Yilma, "Prospects for the total eradication of rinderpest," Vaccine, 7(6):484-485 (1989).
Yoshihara et al., Inferring tumour purity and stromal and immune cell admixture from expression data,: Nature communications 4:2612 (2013).
Yoshitake et al., "Cross-linking of GPI-80, a possible regulatory molecule of cell adhesion, induces up-regulation of CD11b/CD18 expression on neutrophil surfaces and shedding of L-selectin," Journal of leukocyte biology, 71 (2):205-211 (2002).
Young et al., "Resurrection of endogenous retroviruses in antibody-deficient mice," Nature, 491(7426):774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zeestraten et al., "Addition of interferon-alpha to the p53-SLP(R) vaccine results in increased production of interferon-gamma in vaccinated colorectal cancer patients: a phase I/11 clinical trial," Int J Cancer, 132(7):1581-1591 (2013).
Zhang et al., "Machine learning competition in immunology-prediction of HLA class I binding peptides," J Immunol Methods 374:1-4 (2009).
Zhou et al., "A hypermorphic missense mutation in PLCG2, encoding phospholipase C gamma2, causes a dominantly inherited autoinflammatory disease with immunodeficiency," Am J Hum Genet, 91:713-20 (2012).
Zhou et al., "Long-term outcome after haploidentical stem cell transplant and infusion of T cells expressing the inducible caspase 9 safety transgene," Blood, 123(25):3895-3905 (2014).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Ziller et al., "Charting a dynamic DNA methylation landscape of the human genome," Nature, 500:477-481 (2013).
Zitvogel et al., "Immunological aspects of cancer chemotherapy," Nature reviews immunology, 8:59 (2008).
Zorn et al., "A natural cytotoxic T cell response in a spontaneously regressing human melanoma targets a neoantigen resulting from a somatic point mutation," Eur J Immunol, 29(2):592-601 (1999).
Zwaveling et al., "Established human papillomavirus type 16-expressing tumors are effectively eradicated following vaccination with long peptides," J Immunol, 169(1):350-358 (2002).
"A Phase 1 Study of Nivolumab (BMS-936558) in Subjects With Advanced or Recurrent Malignancies (MDX1106-03)," National Library of Medicine, First posted: Aug. 8, 2008 and last updated Mar. 24, 2020. https://clinicaltrials.gov/ct2/show/NCT00730639. Clinical Trials Identifier NCT00730639, 11 pages.
"Dose-escalation Study of Combination BMS-936558 (MDX-1106) and Ipilimumab in Subjects With Unresectable Stage III or Stage IV Malignant Melanoma," National Library of Medicine, First posted: Dec. 2, 2009 and last updated Mar. 22, 2021, 11 pages https://www.clinicaltrials.gov/ct2/show/NCT01024231, Clinical Trials Identifier NCT01024231.

"Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001) (KEYNOTE-001)," National Library of Medicine, First posted: Feb. 15, 2011 and last updated Dec. 13, 2019, 23 pages https://clinicaltrials.gov/ct2/show/NCT01295827, Clinical Trials Identifier NCT01295827.
Adam Piore., "Custom Cancer Vaccines," Feb. 27, 2019 edition of MIT Technology Review, 24 pages.
Akinleye et al., "Ibrutinib and novel BTK inhibitors in clinical development," Journal of Hematology & Oncology, 6(59): 1-9 (2013).
Aiderton G. "Research Highlights" from vol. 13 of Nature Reviews, *Cancer* (Apr. 2013), 1 page.
Aranda et al. "Motely Malignancies" p. 1565 from vol. 19, No. 12 of *Nature Medicine* (Dec. 2013), entitled "Notable advances 2013", 2 pages.
Blackwell HE, Grubbs RH (1998). "Highly Efficient Synthesis of Covalently Cross-Linked Peptide Helices by Ring-Closing Metathesis". Angewandte Chemie International Edition. 37(23): 3281-3284.
Callahan et al., "Nivolumab Plus Ipilimumab in Patients With Advanced Melanoma: Updated Survival, Response, and Safety Data in a phase I Dose-Escalation Study," J Clin Oncol, 36(4): 391-398 (2018).
CNBC news article posted online on Mar. 1, 2019 entitled "Bill Gates: These breakthrough technologies are going to profoundly change the world", 9 pages.
Dana-Farber Cancer Institute; Feb. 20, 2013 publication of the Dana-Farber Cancer Institute entitled, Inside the Institute; and the article "Study tracks evolution of leukemia.", 2 pages.
Datasheet for the decision of May 31, 2007, Boards of Appeal of The European Patent Office, T 1396/06, 26 pages.
Diaz et al., "The molecular evolution of acquired resistance to targeted EGFR blockade in colorectal cancers," Nature, 486: 537-540 (2012).
Duarte "Milestone 21 Individualized neoantigen vaccines" Nature Milestones, Nov. 2020: S3-S25, 25 pages.
Fackler et al., "Quantitative Multiplex Methylation-Specific PCR Assay for the Detection of Promoter Hypermethylation in Multiple Genes in Breast Cancer," Cancer Research, 64(13): 4442-4452 (2004).
History of Changes for Study: NCT01176461, Vaccine Therapy and Monoclonal Antibody Therapy in Treating Patients with Stage III or Stage IV Melanoma That Cannot Be Ren by Surgery, (6 pages) (2010).
Hofmann et al., "Presence of the BCR-ABL mutation Glu255Lys prior to STI571 (imatinib) treatment in patients with Ph+ acute lymphoblastic leukemia," Blood, 102(2): 659-661 (2003).
Kyte et al., "A Simple Method for Displaying the Hydropathic Character of a Protein," J. Mol. Biol., 157: 105-132 (1982).
Lavranos Declaration dated Jan. 12, 2022, 6 pages.
Lavranos Declaration dated Jan. 17, 2022, 12 pages.
Lee et al., "Monocyte-derived dendritic cells from HLA-matched allogenic donors showed a greater ability to induce leukemic cell-specific T cells in comparison to leukemic cell-derived dendritic cells or monocyte-derived dendritic cells from AML patients." Leukemia Research, 32: 1653-1660 (2008).
Peters et al., "A Community Resource Benchmarking Predictions of Peptide Binding to MHC-I Molecules," PLoS Computational Biology, 2(6): e65 (2006), 11 pages.
Sigalotti et al., "Intratumor Heterogeneity of Cancer/Testis Antigens Expression in Human Cutaneous Melanoma Is Methylation-Regulated and Functionally Reverted by 5-Aza-2?-deoxycytidine," Cancer Research, 64(24): 9167-9171 (2004).
Singh et al., "CIMT 2010: Report on the eighth annual meeting of the association for cancer immunotherapy, May 26-28, 2010, Mainz, Germany," Cancer Immunol. Immunother., 60: 443-450 (2011).
Somasundaram et al., "Human Leukocyte Antigen-A2-Restricted CTL Responses to Mutated BRAF Peptides in Melanoma Patients," Cancer Res, 66(6): 3287-3293 (2006).
Tjernberg et al., "DMSO-Related Effects in Protein Characterization," Journal of Biomolecular Screening, 11(2): 131-137 (2006).

(56) References Cited

OTHER PUBLICATIONS

Topalian et al., "Five-Year Survival and Correlates Among Patients With Advanced Melanoma, Renal Cell Carcinoma, or Non-Small Cell Lung Cancer Treated With Nivolumab," JAMA Oncol., 5(10): 1411-1420 (2019).

Turke et al.. "Preexistence and Clonal Selection of MET Amplification in EGFR Mutant NSCLC," Cancer Cell, 17: 77-88 (2010).

Velez et al., "BNT221, an Autologous Neoantigen-Specific T cell Product for Adoptive Cell Therapy of Metastatic Ovarian Cancer" poster presented Oct. 2021 at SITC, 1 page.

Vonderheide et al, "Immunotherapy at Large: The road to personalized cancer vaccines," Nature Medicine 19(9) 1098-1100 (2013).

Wu et al., "Heterogeneity of Breast Cancer Metastases: Comparison of Therapeutic Target Expression and Promoter Methylation Between Primary Tumors and Their Multifocal Metastases," Clinical Cancer Research, 14(7): 1938-1946 (2008).

Wu et al., "Structure-based engineering of a monoclonal antibody for improved solubility," Protein Engineering, Design & Selection, 23(8): 643-651 (2010).

Carlino et al., "Immune checkpoint inhibitors in melanoma," Lancet, 398: 1002-1014 (2021).

Coulie et al., "Genes Coding for Antigens Recognized on Human Tumors by Autologous Cytolytic T Lymphocytes," Annals of New York Academy of Sciences: 113-119 (1993).

Coulie et al., "Tumour antigens recognized by T lymphocytes: at the core of cancer immunotherapy," Nature Review, 14: 135-146 (2014).

Extended European Search Report for EP Application No. 22162718.5 dated Jul. 1, 2022.

Gaynor et al., "GATA3 Mutations Found in Breast Cancers May Be Associated with Aberrant Nuclear Localization, Reduced Transactivation and Cell Invasiveness", Hormones and Cancer, 4: 123-139 (2013).

Kantoff et al., "Sipuleucel-T Immunotherapy for Castration-Resistant Prostate Cancer," The New England Journal of Medicine, 363: 411-422 (2010).

Kirstensen et al., "The Antigenicity of the Tumor Cell—Context Matters." The New England Journal of Medicine, 376(5): 491-493 (2017).

McGranahan et al., "Clonal neoantigens elicit T cell immunoreactivity and sensitivity to immune checkpoint blockade," Science, 351(6280): 1463-1469 (2016).

Melief., "Cancer Immunotherapy by Dendritic Cells" Immunity, 29: 372-383 (2008).

Melief., "Precision T-cell therapy targets tumours," Nature, 547(7662): 165-167 (2017).

Reck et al., "First-Line Immunotherapy for Non-Smalll-Cell Lung Cancer," Journal of Clinical Oncology, 40(6): 586-597 (2022).

Shrock et al., "Tumor mutational burden is predictive of response to immune checkpoint inhibitors in MSI-high metastatic colorectal cancer," Annals of Oncology, 30:1096-1103 (2019).

POLYMORPHIC GENE TYPING AND SOMATIC CHANGE DETECTION USING SEQUENCING DATA

RELATED APPLICATIONS AND INCORPORATION BY REFERENCE

This application claims benefit of U.S. provisional application Ser. No. 61/912,305 filed Dec. 5, 2013.

FEDERAL FUNDING LEGEND

This invention was made with government support under Grant No. CA155010 awarded by the National Institutes of Health. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This disclosure relates generally to gene typing and mutation detection of polymorphic genes using sequencing data, including whole exome sequencing data.

BACKGROUND OF THE INVENTION

The human genome comprises multiple highly polymorphic gene loci such as the Human Leukocyte Antigen (HLA) locus. Human leukocyte antigens (HLAs) are highly polymorphic proteins that present peptides to T cell receptors to initiate the adaptive immune response and to set the boundaries between self and non-self. Exact determination of an individual's gene type for these highly polymorphic genes has numerous applications including identification of compatible organ donors, understanding autoimmunity and immune biology, and design of personalized medicines. Gene typing is typically a focused effort informed by directed experimental protocols. This is commonly performed by sequencing exons 2-4 of Class I genes (HLA-A, -B and -C) and exons 2 and/or 3 of Class II genes (HLA-DRB1 and -DQB1) (Chang et al., ATHLATES: accurate typing of human leukocyte antigen through exome sequencing. Nucleic Acids Research, 2013, 1-8; Lind et al., Next-generation sequencing: the solution for high-resolution, unambiguous human leukocyte antigen typing. Hum. Immunol. 2010; 71:1033-1042.). Due to the extreme diversity of HLA alleles in the population, sequence ambiguities frequently arise when the polymorphisms are outside the regions being typed and when different allelic combinations share the same sequence. Additional steps such as polymerase chain reaction (PCR) with sequence-specific primers are necessary to resolve these ambiguities (Erlich, HLA DNA typing: past, present, and future. Tissue Antigens. 2012; 80:1-11). Although this workflow determines the HLA genotypes at high resolution, it is laborious and expensive.

Next-generation sequencing has been applied to sequencing short-range amplicons of informative exons (Gabriel C, et al., Rapid high-throughput human leukocyte antigen typing by massively parallel pyrosequencing for high-resolution allele identification. Hum. Immunol. 2009; 70:960-964; Bentley et al., High-resolution, high-throughput HLA genotyping by next-generation sequencing. Tissue Antigens. 2009; 74:393-403.) It has also been applied to sequencing long-range amplicons of whole HLA genes on various platforms (Erlich, et al., Next-generation sequencing for HLA typing of class I loci. BMC Genomics 2011; 12:42; Wang et al., High-throughput, high-fidelity HLA genotyping with deep sequencing. Proc. Natl Acad. Sci. USA 2012; 109:8676-8681; Shiina et al., Super high resolution for single molecule-sequence-based typing of classical HLA loci at the 8-digit level using next generation sequencers. Tissue Antigens 2012; 80:305-316.), suggesting a potential for parallel high-throughput HLA typing. Illumina sequencing of captured HLA genes is a cost-effective alternative that can bypass long-range PCRs. However, this is challenging because reads specific to target HLA genes are not readily available, read coverage may vary substantially among different exons and between heterozygous alleles owing to capturing bias, and the typical short read length and the level of polymorphism within the region increase the difficulty of differentiating near-identical alleles. Currently, there is no method to reliably accomplish this task given the challenges. Moreover, poor allelic HLA typing results from exome-seq data even at high coverage has been demonstrated (Warren et al., Derivation of HLA types from shotgun sequence datasets. Genome Med. 2012; 4:95).

Whole exome sequencing (WES, capture sequencing), is a widely used technique for high-throughput sequencing of the coding regions of genes across the genome. Although the use of WES as a research and clinical tool is expanding, the non-specificity and relative low-fidelity of WES compared to directed experimental protocols makes it challenging to use this strategy for gene typing. Gene typing must be generated de novo for each subject. Accordingly, methods for producing high precision polymorphic gene typing from these types of sequencing data, such as WES data, are needed.

Citation or identification of any document in this application is not an admission that such document is available as prior art to the present invention.

SUMMARY OF THE INVENTION

In one aspect this disclosure is directed to methods for determining polymorphic gene types that may comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

In certain example embodiments the sequencing data set is from massively parallel sequencing. This includes any high-throughput approach to DNA sequencing using the concept of massively parallel processing. That is technologies utilizing parallelized platforms for sequencing more than about 1 million to 43 billion short reads (50-400 bases each) per instrument run. In more specific embodiments the sequencing data is from massive parallel sequencing via spatially separated, clonally amplified DNA templates or single DNA molecules in a flow cell. In preferred embodiments sequencing data is whole exome sequencing data, RNA-Seq data, whole genome data, or targeted exome sequencing data.

In certain example embodiments, the reads in the sequencing data set may consist of reads that map to a reference genetic sequence of the polymorphic gene within a threshold base number value. The threshold base number value may be between approximately 0.5 Kb and approximately 5 Kb. In one example embodiment, the threshold base number value is 1 Kb.

In certain embodiment reads are extracted from the sequencing data set. In one embodiment the data is extracted by assembly of the short sequences de novo. In another embodiment the data is extracted by mapping to a known sequence from a subject of the same species.

In certain embodiments an alignment is generated using the extracted reads. The alignment may utilize a non-naturally occurring reference genetic sequence. The reference genetic sequence may be constructed from a library of known or inferred genomic and or cDNA sequences of the polymorphic gene or polymorphic genes to be typed. In one embodiment every extracted read is aligned with every sequence within the reference library. In certain example embodiments, the reads in the sequencing data set may consist of reads that match one or more sequences from a reference genetic sequence. The reads may match one or more sequences from the reference genetic sequence in the 5' to 3' direction or the 3' to 5' orientation. In certain example embodiments, the reads have between approximately 90% and approximately 100% sequence identity to one or more sequences in the reference genetic sequence. In one example embodiment the reads have approximately 100% sequence identity to one or more sequences in the reference genetic sequence.

In certain example embodiments, the reads in the sequencing data set may consist of reads that match one or more probes from a polymorphic gene probe set. The reads may match one or more probes from the polymorphic gene set in the 5' to 3' direction or the 3' to 5' orientation. In one example embodiment, the probes are derived from a library of known or inferred genomic and or cDNA sequences of the polymorphic gene. In certain example embodiments, the reads have between approximately 90% and approximately 100% sequence identity to one or more probes in the polymorphic gene probe set. In one example embodiment the reads have approximately 100% sequence identity to one or more probes in the polymorphic gene probe set. In certain example embodiments, the probes in the polymorphic gene probe set have a size between approximately 25 mer and approximately 100 mer. In one example embodiment, the probes in the polymorphic gene probe set have a size of 38 mer. In another example embodiment, the probes in the polymorphic gene probe set have a size equal to half the read length in the sequencing experiment.

In certain embodiments the sequencing data sets, reference genetic sequence, or polymorphic gene probe set correspond to an animal. In one embodiment the sequencing data sets, reference genetic sequence, or polymorphic gene probe set correspond to a mammal. In another embodiment the sequencing data sets, reference genetic sequence, or polymorphic gene probe set correspond to a rodent. In a preferred embodiment the sequencing data sets, reference genetic sequence, or polymorphic gene probe set correspond to a human.

In certain example embodiments, the first and second posterior probability or posterior probability derived scores are determined based at least in part on base quality scores and an insert size probability value for each read in the alignment. The insert size probability value may be based at least in part on an insert size distribution of all reads in the data set. In one example embodiment, the first and second posterior probabilities or posterior probability derived scores are calculated based at least in part on population-based allele probability observed in a known population data set.

In certain example embodiments, the weighing factor for a given read mapping to the identified first allele variant and the other allele variant is equal to the contribution of the read to the overall posterior probability or posterior probability derived score of the other allele variant ($s_1$) divided by a sum of that contribution and a similar contribution of the read to the overall posterior probability or posterior probability derived score of the first identified allele variant ($s_2$). In one example embodiment the weighting factor $w=s_1/(s_1+s_2)$, and the new contribution of the read to the overall posterior probability or posterior probability derived score of other allele variant$=w*s_1$.

In one embodiment the polymorphic gene is any gene in an animal that has more than one allele. In certain example embodiments, the polymorphic gene is Type I and II human leukocyte antigen gene (HLA) such as HLA-A, HLA-B, HLA-C, HLA-DPA1, HLA-DPB1, HLA-DQA1, HLA-DQB1, HLA-DRA, HLA-DRB1, MICA and MICB, TAP1 and TAP2, KIR, or the IGHV genes. In one example embodiment, the polymorphic gene is a human leukocyte antigen gene.

In another aspect the disclosed invention is directed to methods for determining mutations in polymorphic genes comprising extracting a first set of gene-specific reads from a first sequencing data set obtained from normal tissue of a subject, extracting a second set of gene-specific reads from a second sequencing data set obtained from diseased tissues of the subject, determining a genotype sequence from the reads extracted from the first sequencing set using the genotyping methods disclosed herein, aligning the first set of gene-specific reads and the second set of gene-specific reads to the determined genotype sequence, detect mutations based at least in part on the generated sequence alignment. In certain example embodiments, the sequencing data may be whole exome sequencing data.

In certain embodiments an output that includes data is generated. In one embodiment the output provides data that indicates the first and second allele variants for the individual. In one embodiment the output provides data that indicates the mutations for the inferred alleles. In one embodiment the output is electronic. In one embodiment the output is printed.

In certain embodiments the methods are incorporated into a method to formulate a neoantigen immunogenic composition. The invention comprehends performing methods as in U.S. patent application No. 20110293637, incorporated herein by reference, e.g., a method of identifying a plurality of at least 4 subject-specific peptides and preparing a subject-specific immunogenic composition that upon administration presents the plurality of at least 4 subject-specific peptides to the subject's immune system, wherein the subject has a tumor and the subject-specific peptides are specific to the subject and the subject's tumor, said method comprising:

(i) identifying, including through nucleic acid sequencing of a sample of the subject's tumor and nucleic acid sequencing of a non-tumor sample of the subject, a plurality of at least 4 tumor-specific non-silent mutations not present in the non-tumor sample; and (ii) selecting from the identified non-silent mutations the plurality of at least 4 subject-specific peptides, each having a different tumor neo-epitope that is an epitope specific to the tumor of the subject, from the identified plurality of tumor specific mutations, wherein each neo-epitope is an expression product of a tumor-specific non-silent mutation not present in the non-tumor sample, each neo-epitope binds to a HLA protein of the subject, and selecting includes determining binding of the subject-specific peptides to the HLA protein, and (iii) formulating the subject-specific immunogenic composition for administration to the subject so that upon administration the plurality of at least 4 subject-specific peptides are presented to the subject's immune system, wherein the selecting or formulating comprises at least one of:

including in the subject-specific immunogenic composition a subject-specific peptide that includes an expression product of an identified neo-ORF, wherein a neo-ORF is a tumor-specific non-silent mutation not present in the non-tumor sample that creates a new open reading frame, and including in the subject-specific immunogenic composition a subject-specific peptide that includes an expression product of an identified point mutation and has a determined binding to the HLA protein of the subject with an IC50 less than 500 nM, or any other metric such as the differential of the IC50 values between the native and corresponding mutated peptide being greater than a pre-defined value, whereby, the plurality of at least 4 subject-specific peptides are identified, and the subject-specific immunogenic composition that upon administration presents the plurality of at least 4 subject-specific peptides to the subject's immune system, wherein the subject-specific peptides are specific to the subject and the subject's tumor, is prepared; or a method of identifying a neoantigen comprising:

a. identifying a tumor specific mutation in an expressed gene of a subject having cancer;

b. wherein when said mutation identified in step (a) is a point mutation:

i. identifying a mutant peptide having the mutation identified in step (a), wherein said mutant peptide binds to a class I HLA protein with a greater affinity than a wild-type peptide; and has an IC50 less than 500 nm, or any other metric such as the differential of the IC50 values between the native and corresponding mutated peptide being greater than a pre-defined value;

c. wherein when said mutation identified in step (a) is a splice-site, frameshift, read-through or gene-fusion mutation:

i. identifying a mutant polypeptide encoded by the mutation identified in step (a), wherein said mutant polypeptide binds to a class I HLA protein; or a method of inducing a tumor specific immune response in a subject comprising administering one or more peptides or polypeptides identified and an adjuvant; or a method of vaccinating or treating a subject for cancer comprising:

a. identifying a plurality of tumor specific mutations in an expressed gene of the subject wherein when said mutation identified is a:

i. point mutation further identifying a mutant peptide having the point mutation; and/or ii. splice-site, frameshift, read-through or gene-fusion mutation further identifying a mutant polypeptide encoded by the mutation;

b. selecting one or more mutant peptides or polypeptides identified in step (a) binds to a class I HLA protein;

c. selecting the one or more mutant peptides or polypeptides identified in step (b) that is capable of activating anti-tumor CD8 T-cells; and d. administering to the subject the one or more peptides or polypeptides, autologous dendritic cells or antigen presenting cells pulsed with the one or more peptides or polypeptides selected in step (c); or preparing a pharmaceutical composition comprising one identified peptide(s), and performing method(s) as herein discussed. Thus, the neoplasia vaccine or immunogenic composition herein can be as in U.S. patent application No. 20110293637.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. Nothing in this disclosure is to be construed as a promise.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

DETAILED DESCRIPTION OF THE INVENTION

In one aspect, embodiments herein provide computer-implemented techniques for gene typing polymorphic genes using sequencing data. In certain example embodiments the sequencing data is whole exome sequencing data (WES), RNA-Seq data, whole genome data, targeted exome sequencing data, or any form of sequencing data that covers the polymorphic loci at either the exome, genome, or RNA levels. In a preferred embodiment the present invention provides novel computer-implemented techniques for transforming next generation sequencing or massively parallel sequencing data into allelic data for polymorphic genes. For ease of reference, the example embodiments will be described below with reference to WES data, but other sequencing data as described above may be used interchangeably. Example polymorphic genes include the Type I and II HLA loci such as HLA-A, HLA-B, HLA-C, HLA-DPA1, HLA-DPB1, HLA-DQA1, HLA-DQB1, HLA-DRA, HLA-DRB1 the MICA and MICB genes, the TAP1 and TAP2 genes, KIR, and the IGHV genes. In one example embodiment, the polymorphic gene is an HLA gene.

Polymorphic gene typing can be used, for example, in identifying compatible organ donors and selecting appropriate personalized medicine treatment regimes, such as an immunogenic composition or vaccine that includes neoepitopes. Whole genome/exome sequencing may be used to identify all, or nearly all, mutated neoantigens that are uniquely present in a neoplasia/tumor of an individual patient, and that this collection of mutated neoantigens may be analyzed to identify a specific, optimized subset of neoantigens for use as a personalized cancer vaccine or immunogenic composition for treatment of the patient's neoplasia/tumor. For example, a population of neoplasia/tumor specific neoantigens may be identified by sequencing the neoplasia/tumor and normal DNA of each patient to identify tumor-specific mutations, and the patient's HLA allotype can be identified. The population of neoplasia/tumor specific neoantigens and their cognate native antigens may then be subject to bioinformatic analysis using validated algorithms to predict which tumor-specific mutations create epitopes that could bind to the patient's HLA allotype. Based on this analysis, a plurality of peptides corresponding to a subset of these mutations may be designed and synthesized for each patient, and pooled together for use as a cancer vaccine or immunogenic composition in immunizing the patient.

Figure 1:
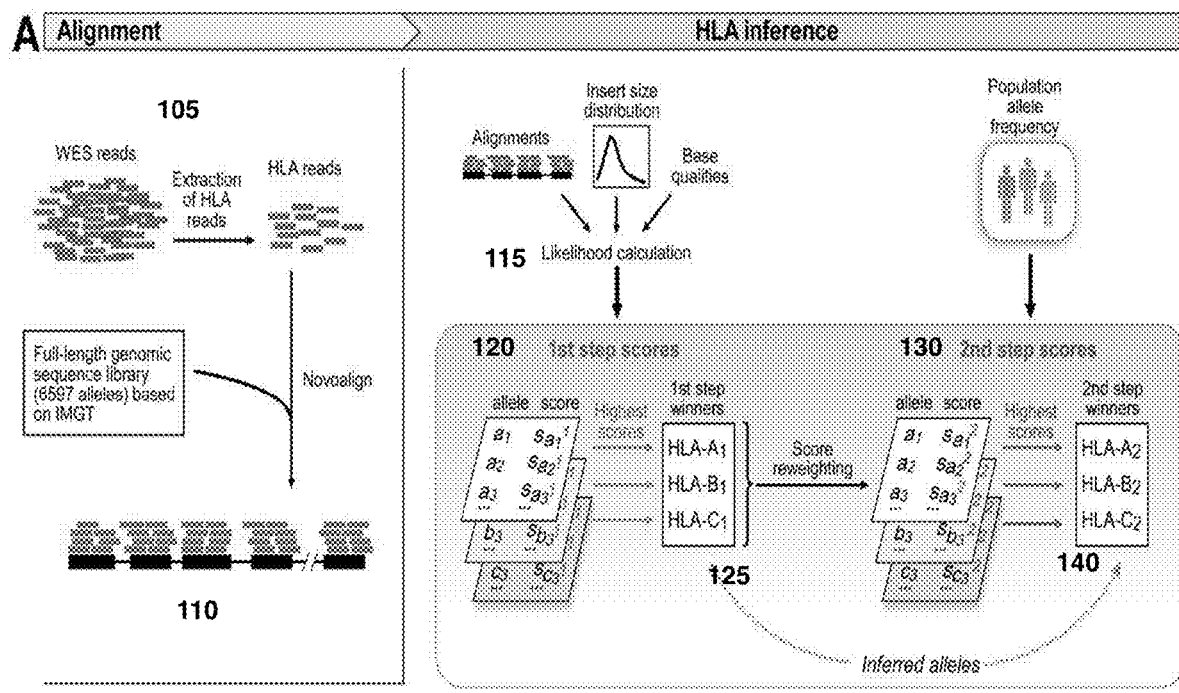
FIG. 1 is a process flow diagram of a method for gene typing polymorphic genes using whole exome sequence data, in accordance with certain example embodiments.

An overview of the process for determining polymorphic gene types is provided with reference to FIG. 1. The process starts by extracting reads from a set of whole exome sequencing (WES) data that map to the polymorphic gene of interest ("target polymorphic gene") 105. In one embodiment the data is extracted by assembly of the short sequences de novo. In another embodiment the data is extracted by mapping to a known sequence from a subject of the same species. More than one polymorphic gene may be analyzed at the same time. In one embodiment, multiple genes, such as the HLA-A, HLA-B, and HLA-C can be analyzed concurrently.

The extracted reads are then aligned to a reference genetic sequence set constructed with known allele variants of the target polymorphic gene and/or genes 110. The reference genetic sequence may be constructed from a library of known or inferred genomic and or cDNA sequences of the polymorphic gene or polymorphic genes to be typed. In one embodiment every extracted read is aligned with every allele sequence corresponding to the extracted read within the reference library. In certain example embodiments, the reads in the sequencing data set may consist of reads that match one or more sequences from a reference genetic sequence. The reads may match one or more sequences from the reference genetic sequence in the 5' to 3' direction or the 3' to 5' orientation. In certain example embodiments, the reads have between approximately 90% and approximately 100% sequence identity to one or more sequences in the reference genetic sequence. In one example embodiment the reads have approximately 100% sequence identity to one or more sequences in the reference genetic sequence.

The generated sequence alignment and other information 115, such as an insert size distribution for the aligned reads, alignment quality scores and population frequencies, are used to calculate a first posterior probability or posterior probability derived score for each allele variant 120. The allele variant that maximizes the first posterior probability or posterior probability derived score is selected as the first allele variant of the target polymorphic gene type 125. A second posterior probability or posterior probability derived score is calculated for each allele by applying a heuristic weighting strategy to the score contribution of each of its aligned reads from the first stage, taking into consideration whether a read under consideration also mapped to the first inferred allele variant, 130. The allele variant that maximizes the second posterior probability or posterior probability derived score is selected as the second allele variant 140. The first and second allele variants define the polymorphic gene type and are provided as an output. In one embodiment the allele variants are displayed on a computer screen.

Figure 2:
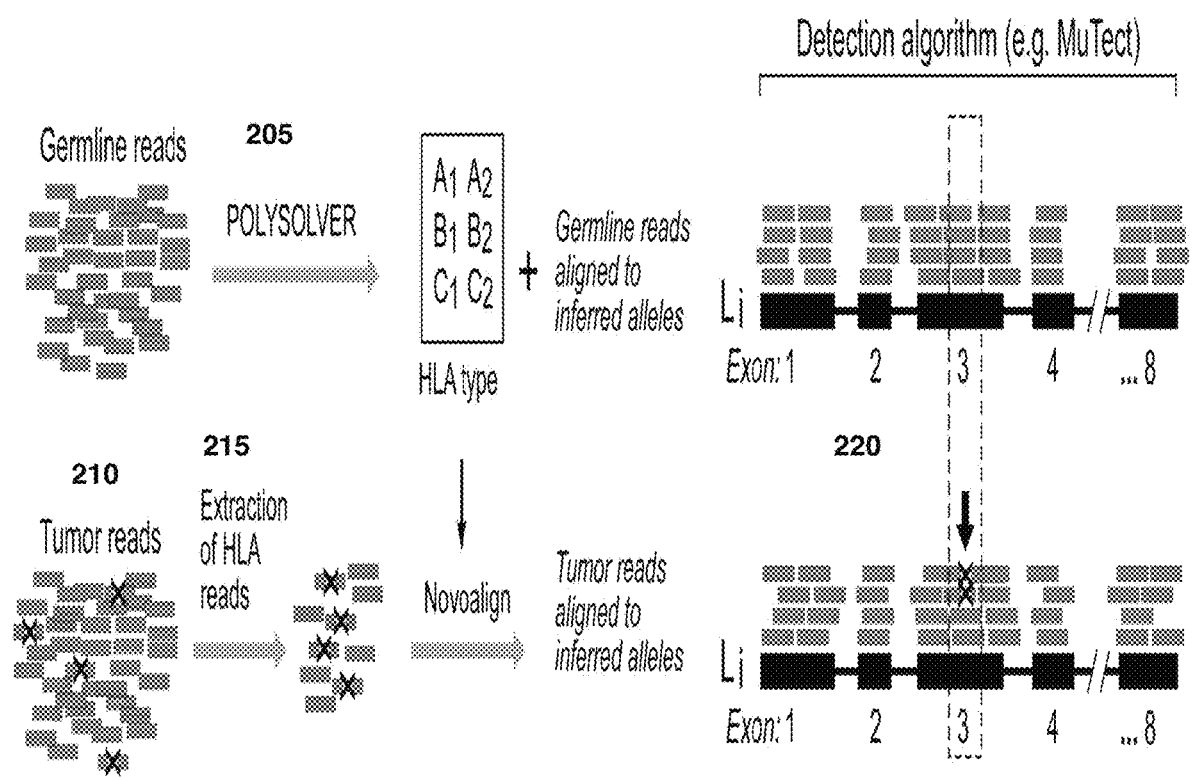
FIG. 2 is a process flow diagram of a method for mutation detection in polymorphic genes using whole exome sequencing data, in accordance with certain example embodiments.

In another aspect, embodiments herein provide computer-implemented techniques for detecting mutations in polymorphic genes by generating polymorphic allele data from sequencing data obtained from normal tissue and comparing the extracted reads of the normal tissue aligned to a reference set of alleles of the polymorphic gene to the extracted reads of disease tissue aligned to a reference set of allelles of the polymorphic gene. As described herein, example embodiments are described with reference to WES data, but other sequencing data types may be used interchangeably. An overview of the process for determining mutations in polymorphic genes is provided with reference to FIG. 2. A WES data set is obtained from normal germline cells of the subject to be tested and a polymorphic gene type is determined according to the polymorphic gene typing method described herein 205 (POLYSOLVER). A second WES data set is obtained from diseased cells, such as cancer cells, from the subject to be tested 210. Reads from the diseased tissue WES data set mapping to the target polymorphic gene are then extracted 215. The extracted reads are then aligned to the polymorphic gene type sequences determined at 205. The resulting alignment is then used to detect mutations in the sequences obtained from the diseased tissue sample based on the predicted polymorphic alleles.

Turning now to FIGS. 3-6, in which like numerals represent like (but not necessarily identical) elements throughout the figures, example embodiments are described in detail.

Example System Architectures

Figure 3:
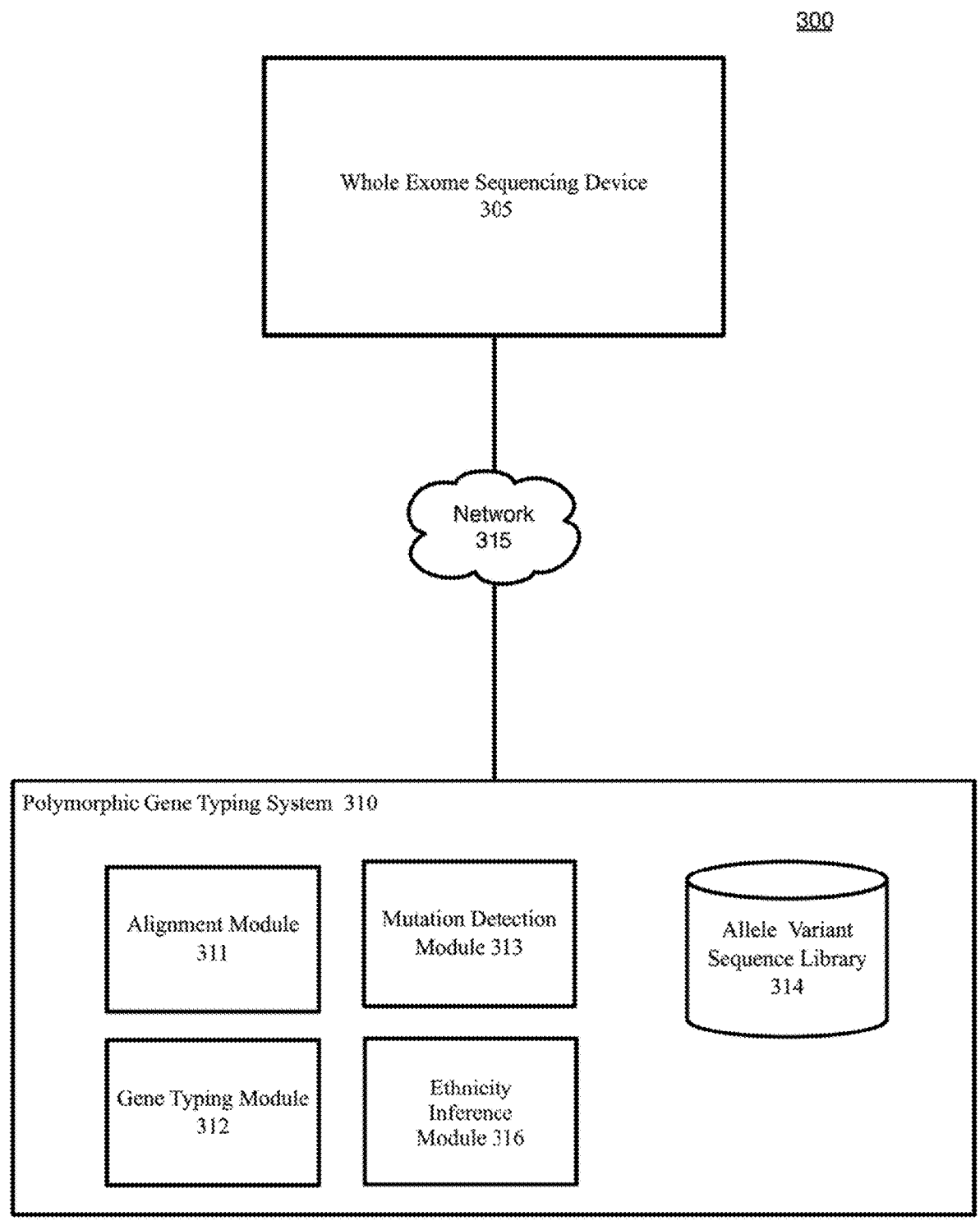
FIG. 3 is a block diagram depicting a system for genotyping polymorphic genes using whole exome sequencing data, in accordance with certain example embodiments.

FIG. 3 is a block diagram depicting a system for determining gene type and detecting mutations in polymorphic genes. As depicted in FIG. 3, the operating environment 300 includes network and 310 that are configured to communicate with one another via one or more networks 315. In some embodiments, a user associated with a device must install an application and/or make a feature selection to obtain the benefits of the techniques described herein.

Each network 315 includes a wired or wireless telecommunication means by which network devices (including devices 305 and 310) can exchange data. For example, each network 315 can include a local area network ("LAN"), a wide area network ("WAN"), an intranet, an Internet, a mobile telephone network, or any combination thereof. Throughout the discussion of example embodiments, it should be understood that the terms "data" and "information" are used interchangeably herein to refer to text, images, audio, video, or any other form of information that can exist in a computer-based environment.

Each network device 305 and 310 includes a device having a communication module capable of transmitting and receiving data over the network 315. For example, each network device 305 and 310 can include a server, desktop computer, laptop computer, tablet computer, a television with one or more processors embedded therein and/or coupled thereto, smart phone, handheld computer, personal digital assistant ("PDA"), or any other wired or wireless, processor-driven device.

The whole exome sequencing device 305 sequences nucleic acid material extracted from a biological sample to generate a whole exome sequencing data file containing information on the coding regions of genes across the sample genome. In one example embodiment, the whole exome sequencing device 305 may directly communicate the WES data file to the polymorphic gene typing system 310 across the network 310 and the gene typing or mutation detection analysis is conducted in line with the sequencing analysis. In another example embodiment, the WES data file may be stored on a data storage medium and later uploaded to the polymorphic gene typing system 310 for further analysis.

The polymorphic gene typing system 310 may comprise an alignment module 311, gene typing module 312, a mutation detection module 313, an ethnicity inference module 316, and an allele variant sequence library 314. The alignment module 311 extracts and aligns reads from the whole exome sequencing data file to a gene reference set. The gene reference set comprises reference sequences for the polymorphic gene being analyzed. The sequence information for the gene reference set is stored in the allele sequence library 314. The ethnicity inference module 316 infers the ethnicity of the individual which then serves as the basis for selection of prior probabilities by the gene typing module. The gene typing module 312 performs a two-stage posterior probability based analysis on the aligned reads to identify the gene type of the sample, optionally using population derived allele frequencies as prior probabilities. The mutation detection module 313 identifies mutations based on an analysis of the gene type and WES data obtained from a diseased tissue sample.

It will be appreciated that the network connections shown are example and other means of establishing a communications link between the computers and devices can be used. Moreover, those having ordinary skill in the art having the benefit of the present disclosure will appreciate that whole exome sequencing device 305 and polymorphic gene typing system 310, can have any of several other suitable computer system configurations.

Example Processes

Figure 4:
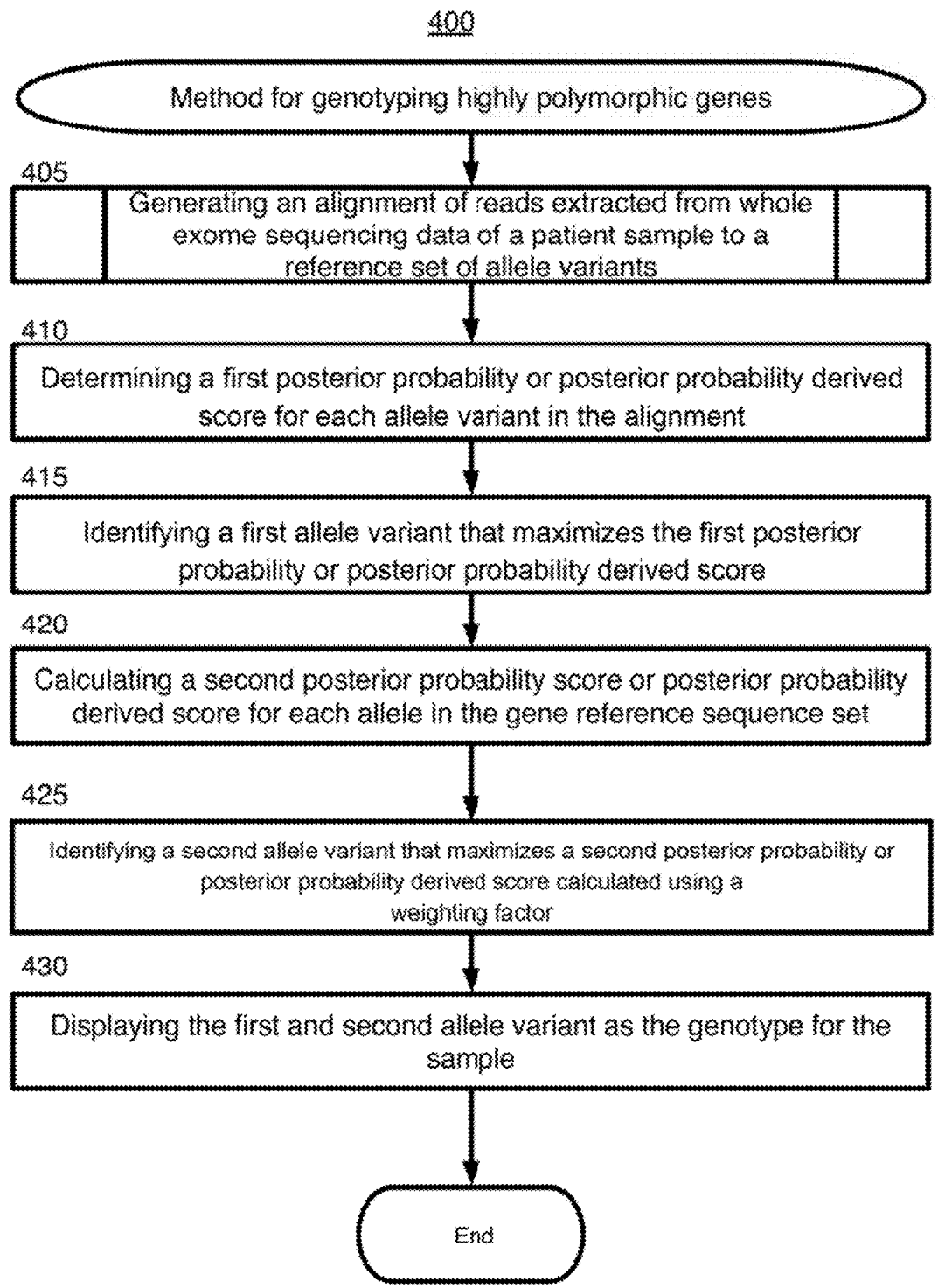
FIG. 4 is a block flow diagram depicting a method to determine a gene type of a polymorphic gene using whole exome sequencing data, in accordance with certain example embodiments.
Figure 5:
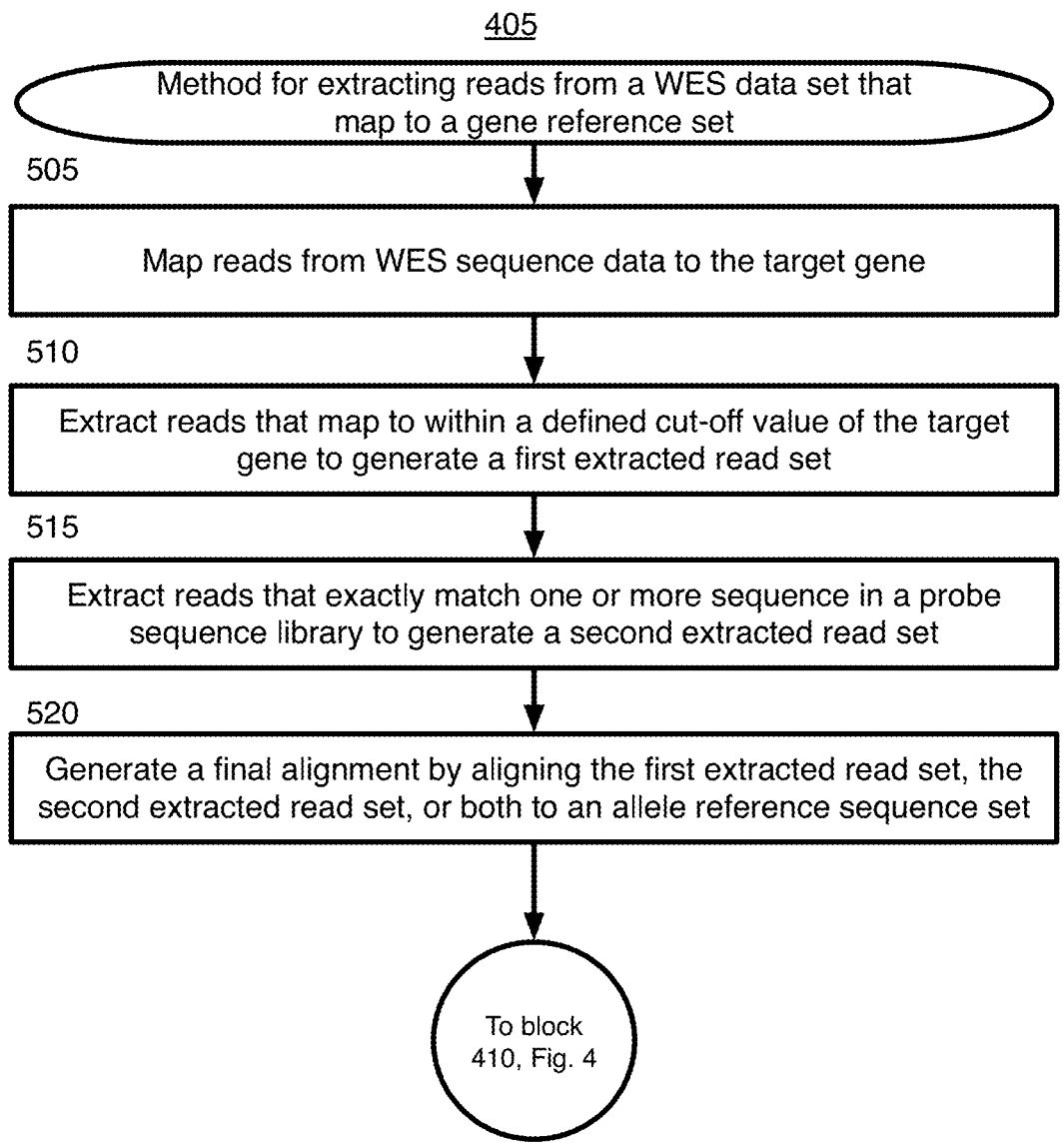
FIG. 5 is a method for extracting reads from a WES data set that map to a gene reference set, in accordance with certain example embodiments.
Figure 6:
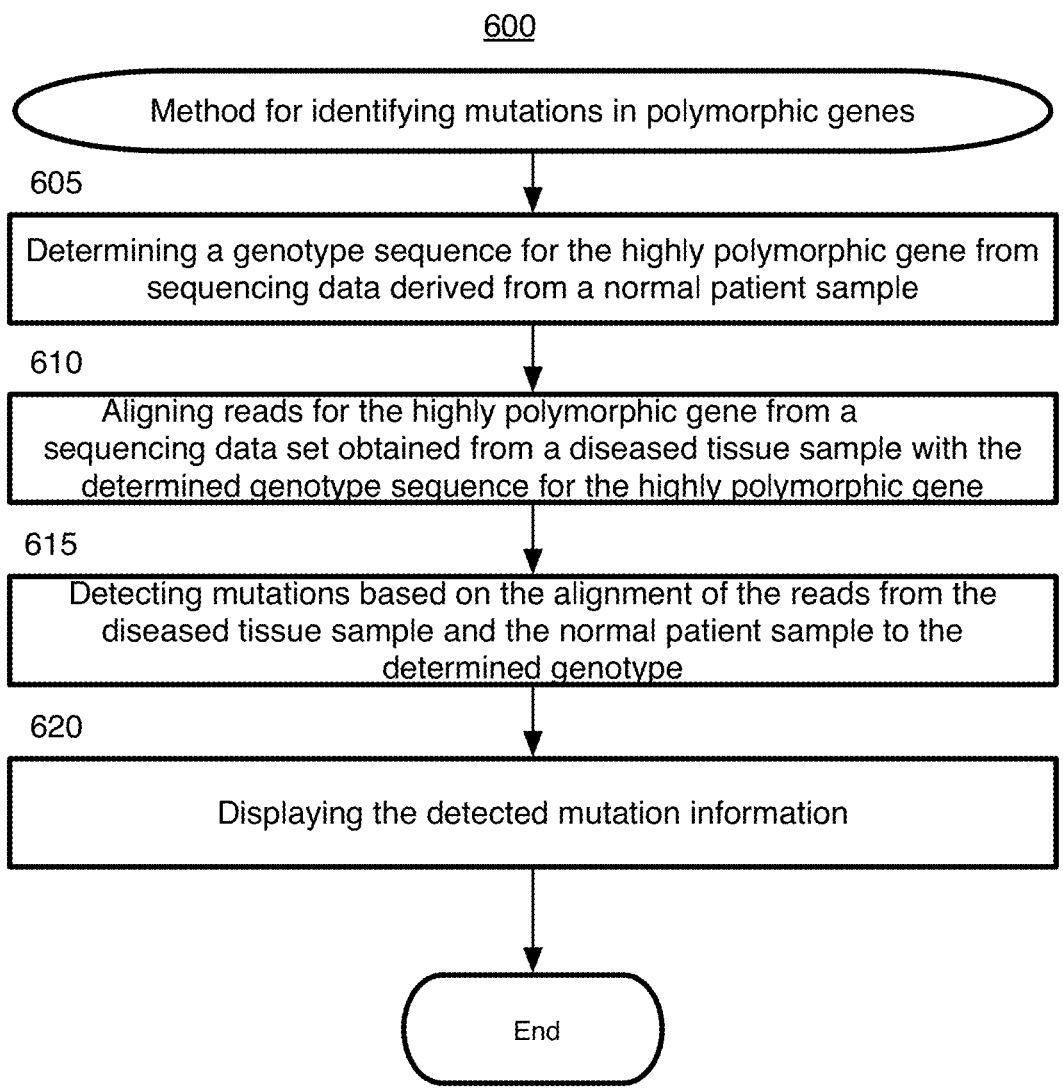
FIG. 6 is a block flow diagram depicting a method to detect mutations in a polymorphic gene using whole exome sequencing data, in accordance with certain example embodiments.

The example methods illustrated in FIG. 4-6 are described herein with respect to the components of the example operating environment 300. The example methods of FIG. 4-6 may also be performed with other systems and in other environments.

FIG. 4 is a block flow diagram depicting a method 400 to determine a polymorphic gene type of one or more polymorphic gene bases on whole exome sequencing data, in accordance with certain example embodiments.

Method 400 begins at block 405, wherein the alignment module 311 generates an alignment of gene reads from WES sequencing data that map to a gene reference sequence for the target gene. Block 405 will be described in further detail with reference to FIG. 5.

FIG. 5 is a block diagram depicting a method 405 to align reads from the WES sequence data with a gene reference set. The method 405 begins at block 505 where the alignment module 311 maps all the reads in the WES sequence data to a reference target gene sequence. The reference target gene sequence may be downloaded directly from a public resource such as IMGT and may comprise genomic or cDNA sequences. It may also be a set of full length genomic sequences along with inferred full length genomic sequences. Missing exons for incompletely sequenced allele cDNAs may be deduced by multiple sequence alignment of the missing allele with all available cDNA sequences. Missing introns may be inferred by alignment of the cDNA sequence with the nearest full-length genomic sequence.

At block 510, the alignment module 311 then extracts all reads that map within a defined cut-off value of the target gene to generate a first extracted read set. In one example embodiment, reads that mapped within 200 to 2000 bases, 200 to 1750 bases, 200 to 1500 bases, 200 to 1250 bases, 200 to 1000, 200 to 750, 200 to 500, 500 to 750, 500 to 1000, 500 to 1250, 500, to 1500, 500 to 1750, 500 to 2000, or 1000 to 2000 bases are extracted. In one example embodiment, the reads mapping to within 1000 bases of the target polymorphic gene are extracted. In certain example embodiments, the alignment module 311 further determines an insert size distribution based on all aligned reads in the sequence data file. This empirical insert size distribution is then utilized by the gene typing module 312 in determining a posterior probability or posterior probability derived score as described in further detail herein.

At block 515, the alignment module 311 extracts reads from the original sequence data file or the completed set of reads in a sequencing run based on comparing each read to a probe sequence set. The probe sequence set may include short probe sequences derived from a library of known genomic and/or cDNA sequences of the target polymorphic gene. Reads that match one or more short probe sequences in a probe sequence set are included in second extracted read set. The reads may match the one or more probes in the 5' to 3' or '3' o 5' orientation. The probe sequences have a size between approximately 25 to approximately 100 mer, approximately 25 to approximately 75 mer, approximately 25 mer to 50 mer, approximately 50 mer to 100 mer, approximately 50 mer to approximately 75 mer and any combination in between. In one example embodiment the probe sequences in the probe sequence library have a size of 38 mer. In one example embodiment, the aligned reads have between 90% and 100% sequence identity with one or more the probe sequences in the probe sequence library. In another example embodiment, the aligned reads have 100% sequence identity with one or more probes in the probe sequence library. A final extracted read set is then used for further analysis and may comprise both extracted read sets 1 and 2, or either of them exclusively.

At block 520, the reads in the final extracted read set are aligned to an allele variant sequence library for the target gene to generate a final alignment. The reads may be aligned to the allele variant sequence library using a standard alignment algorithm. The allele sequence information is stored in the allele variant sequence library 314 and may contain all available allele genomic and cDNA sequences for the target gene, or inferred full length genomic sequences as described herein. In one example embodiment, the alignment algorithm is the "Novoalign" alignment algorithm (Novocraft Selengor, Malaysia). In another example embodiment, the parameters are set to report all best-scoring alignments. In another example embodiment, all alignments that meet a score threshold will be reported. Any new optical or PCR duplicates that are unmasked as a result of the final alignment may or may not be removed. For example, duplicates can be identified and removed using Picard's MarkDuplicates module (picard.sourceforge.net/). The process then proceeds to block 410 of FIG. 4.

Returning to block 410 of FIG. 4, where the gene typing module 312 uses the final alignment to calculate a first posterior probability or posterior probability derived score for each allele variant of the polymorphic gene. The gene typing module 312 first determines a likelihood calculation for each allele variant of the polymorphic gene. In certain example embodiments, a log likelihood score is calculated for each allele variant as follows:

Let:
$N_A$=# alleles corresponding to the HLA gene
$M$=# alleles corresponding to the polymorphic gene
$N$=# reads aligning to at least one allele
$N_m$=# reads aligning to allele $a_m$
$N_T$=# reads in the sequencing run
$f_m$=population based prior probability of allele m
$r_{k1}$=first segment of read pair $r_k$
$r_{k2}$=second segment of read pair $r_k$
$d_k$=insert length of read pair $r_k$
$l_{k1}$=length of first segment of read pair $r_k$
$l_{k2}$=length of second segment of read pair $r_k$ $q_i$=quality of sequenced base i
$e_i$=probability that the sequenced base i is an error $$e_i = 10^{-\frac{q_i}{10}}$$

The quality scores of the alignment can be used to build a model for the sequencing process. Let) $Y_{Ai}$, $Y_{Ci}$, $Y_{Gi}$ and $Y_{Ti}$ denote random variables corresponding to observing bases A, C, G and T respectively at position i in read $r_k$ in its alignment to allele $a_m$. Then $$Y_{Ai}, Y_{Ci}, Y_{Gi}, Y_{Ti} \sim \text{Multinomial}(n = 1; \alpha_{Ai}, \alpha_{Ci}, \alpha_{Gi}, \alpha_{Ti})$$

where $$\alpha_{Bi} = 1 - e_i \text{ if reference base at position } i \text{ in } a_m \text{ is } B$$
$$= e_i/3 \text{ otherwise}$$

D denotes a random variable for the observed insert length of a paired read in the sequencing run based on alignment to the complete genome. For a given read pair $r_k$, the empirical insert size distribution can be used to calculate the probability of observing the insert length $d_k$ as $$P(D = d_k) = \frac{\sum_{l=1}^{N_T} I(d_l = d_k)}{N_T}$$

Assuming positional independence of quality scores, and independence of generated reads and their insert sizes, the probability of observing $r_k$ given allele $a_m$ is then $$P(r_k | a_m) = \begin{cases} \prod_{i=1}^{l_{k1}} a_i \prod_{j=1}^{l_{k2}} a_j \cdot P(D = d_k) & \text{if } r_k \text{ aligns to } a_m \\ s_k & \text{otherwise} \end{cases}$$

where $s_k$ corresponds to the lowest theoretical probability achievable for read pair $r'_k$ with perfect base qualities and segment lengths equal to those of $r_k$. Since 93 is the maximum achievable base quality under Illumina 1.8+ format, $s_k$ is computed as $$s_k = (l_{k1} + l_{k2}) \cdot \log \frac{10^{-9.3}}{3} \approx -23 \cdot (l_{k1} + l_{k2})$$

The posterior probability of allele $a_m$ using all reads that align to it is given by $$P(a_m | r_1, r_2, \ldots, r_N) = \frac{\prod_{k=1}^{N} P(r_k | a_m) \cdot f_m}{\prod_{k=1}^{N} P(r_k)}$$

Log transformation of the above equation yields $$L_m = \sum_{k=1}^{N_m} \sum_{i=1}^{l_{k1}} \log \alpha_i + \sum_{k=1}^{N_m} \sum_{j=1}^{l_{k2}} \log \alpha_j + \sum_{k=1}^{N_m} \log P(D = d_k) + (N - N_m)s_k + \log f_m - \sum_{k=1}^{N} \log P(r_k)$$

Note that the terms $N \cdot s_k$ and $\Sigma_{k=1}^{N} \log P(r_k)$ are constants for all alleles and can be ignored.

The likelihoods of all aligned read pairs to a given allele variant may be computed based on their respective alignments, quality scores, and insert size probabilities based on the empirical insert size distribution of all read pairs in the sequencing run. Population-based allele probabilities may be used as priors in the model. For example, allele frequencies for Caucasian, Black, and Asian ethnicities may be calculated taking a sample-size weighted average of all relevant population studies in the Allele Frequency Net Database (Gonzalez-Galarza et al., 2011).

At block 415, the gene typing module 312 selects the allele variant that maximizes the log posterior probability score or the log of the posterior probability derived score from the calculations determined in block 410 as the first allele variant for the polymorphic gene type.

$$a_w = \underset{a_m}{\text{argmax}} L_m$$

The log posterior probability or the log of the posterior probability derived score calculated in the first stage shall henceforth be referred to as $L_1$ score.

At block 420, the gene typing module 312 calculates a second posterior probability score or posterior probability derived index (either of which will henceforth be referred as the $L_2$ score) for each allele in the database based on the overlap of reads that each allele shares with the first identified allele. A read may have mapped to a position of the first identified allele sequence and also mapped to the same position in a second allele under consideration whose $L_2$ score is being evaluated but with a variance in alignment quality or insert size. The read may also map to a different position in the first and second allele variant with close sequence similarity. The gene typing module 312 computes the $L_2$ score for an allele $a_m$ by applying a heuristic weighting strategy to each of its aligned reads. For a given allele $a_m$, the log likelihood $l_m^k$ of a read $r_k$ that also maps to the first identified allele variant $a_w$ with likelihood $l_w^k$ is weighted by a factor equal to $l_m^k/(l_m^k+l_w^k)$. If only the best-scoring alignments for each read are preserved, this ratio will always be 0.5 (FIG. 1, 140). Reads mapping exclusively to $a_m$ with respect to $a_w$ are assigned a weight of 1. The read insert size and allele prior probability components of the $L_1$ score are preserved from the first stage. Alternatively, the read insert size component may also be included in the heuristic reweighting.

At block 425, the gene typing module 312 identifies the second allele variant for the gene as the allele with the maximal $L_2$ score.

At block 430, the gene typing module 312 displays genotyping information comprising the first allele and second allele variant with maximal $L_1$ and $L_2$ scores as the gene type for the analyzed sample. The gene typing module may additionally display information such as the associated scores, and the alleles with the second highest $L_1$ and $L_2$ scores. The difference in scores between the first and second-highest scoring alleles, or some other derivative metric such as the percentage increase in score between the second-highest and highest scoring alleles in the two stages, may also be displayed. An empirical p-value based on the chosen metric may also be part of the output. The gene typing module 312 may also generate a report comprising the genotyping information. The report may be in electronic format, hard copy format, or both.

FIG. 6 is a block flow diagram depicting a method 600 for identifying mutations in polymorphic genes, in accordance with certain example embodiments.

Method 600 begins at block 605, where the gene typing module 312 determines the gene type of a target polymorphic gene based on an analysis of WES data obtained from a normal tissue sample of a subject. The process for determining the gene type from the normal tissue sample is substantially the same as that described above with reference to blocks 405 to 430 of FIG. 4.

At block 610 the alignment module 311 extracts reads from WES data obtained from a diseased tissue sample of the same subject and aligns the extracted reads with the sequence of the polymorphic gene types determined in block 430. The procedure for extracting and aligning the reads from the diseased tissue WES data is substantially the same as that described above with reference to blocks 505 through 520 of FIG. 5.

At block 615 a mutation module 313 detects mutations or other somatic changes including insertions, deletions, copy number changes and translocations based on the alignment generated at block 610. The mutation module may utilize standard mutation detection or other somatic change detection algorithms known in the art. In certain example embodiments, the "MuTect" method as described in International Patent Application Publication No. WO2014036167 A1 to Cibulskis et al., and hereby incorporated by reference, is used to detect mutations from the alignment data. In certain embodiments, the Strelka software (Saunders et al., 2012) may be used to detect insertions and deletions in the diseased sample.

Figure 17:
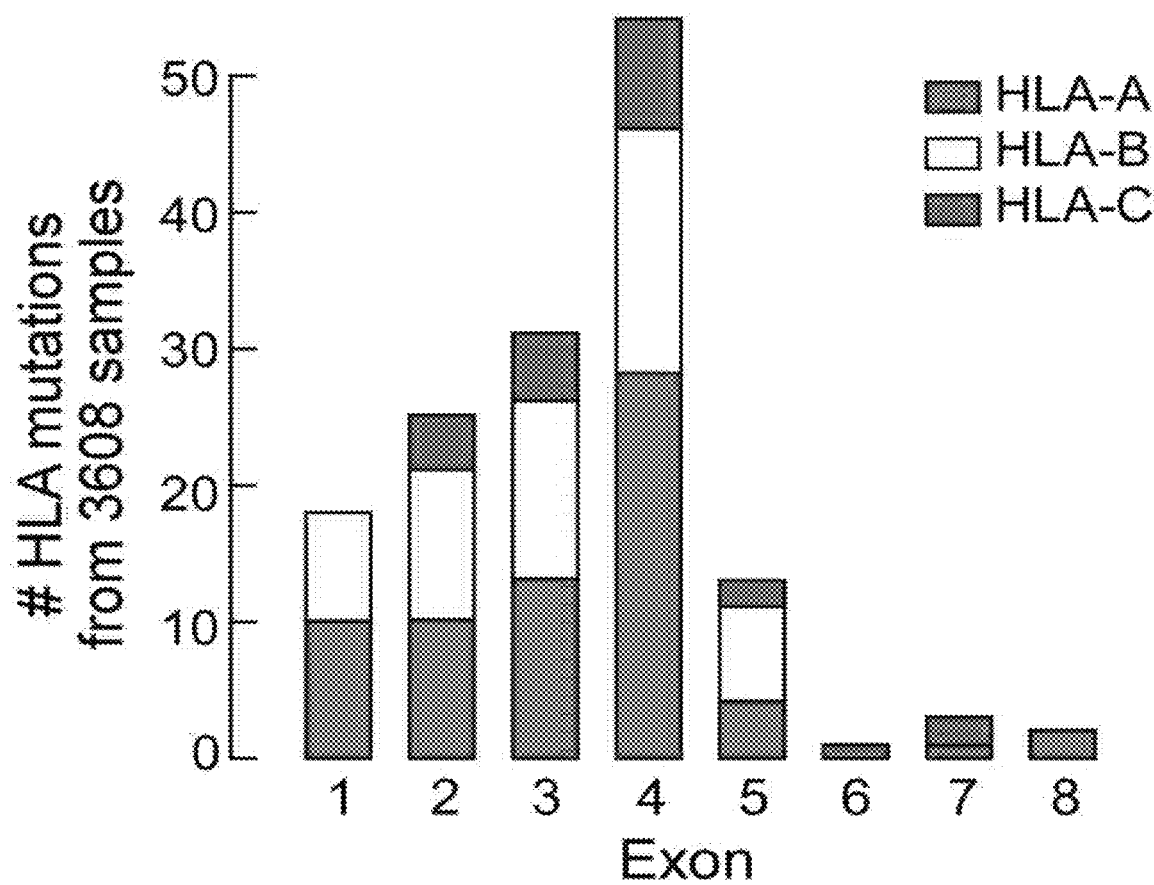
FIG. 17 is a graph showing the distribution of HLA mutations across exons.

At block 620, the mutation module 313 displays the detected mutation information. The detected mutation information may include the position, mutated or alternate bases, reference bases, sequence context, codon changes, protein changes, number of reads supporting the reference and alternate bases in the tumor and normal samples, a goodness score such as a log odds score for the change. The detected mutation information may include a mapping of the mutations positions in a two-dimensional or three-dimensional schematic of the corresponding transcribed protein. For example, the detection mutation information may include a schematic like that shown in FIG. 17 that maps the mutations to key contact points between the corresponding protein and one or more binding partners of the protein. The mutation module 313 may generate a report comprising the detected mutation information described above. The report may be generated in electronic format, hard copy format, or both.

Other Example Embodiments

Figure 7:
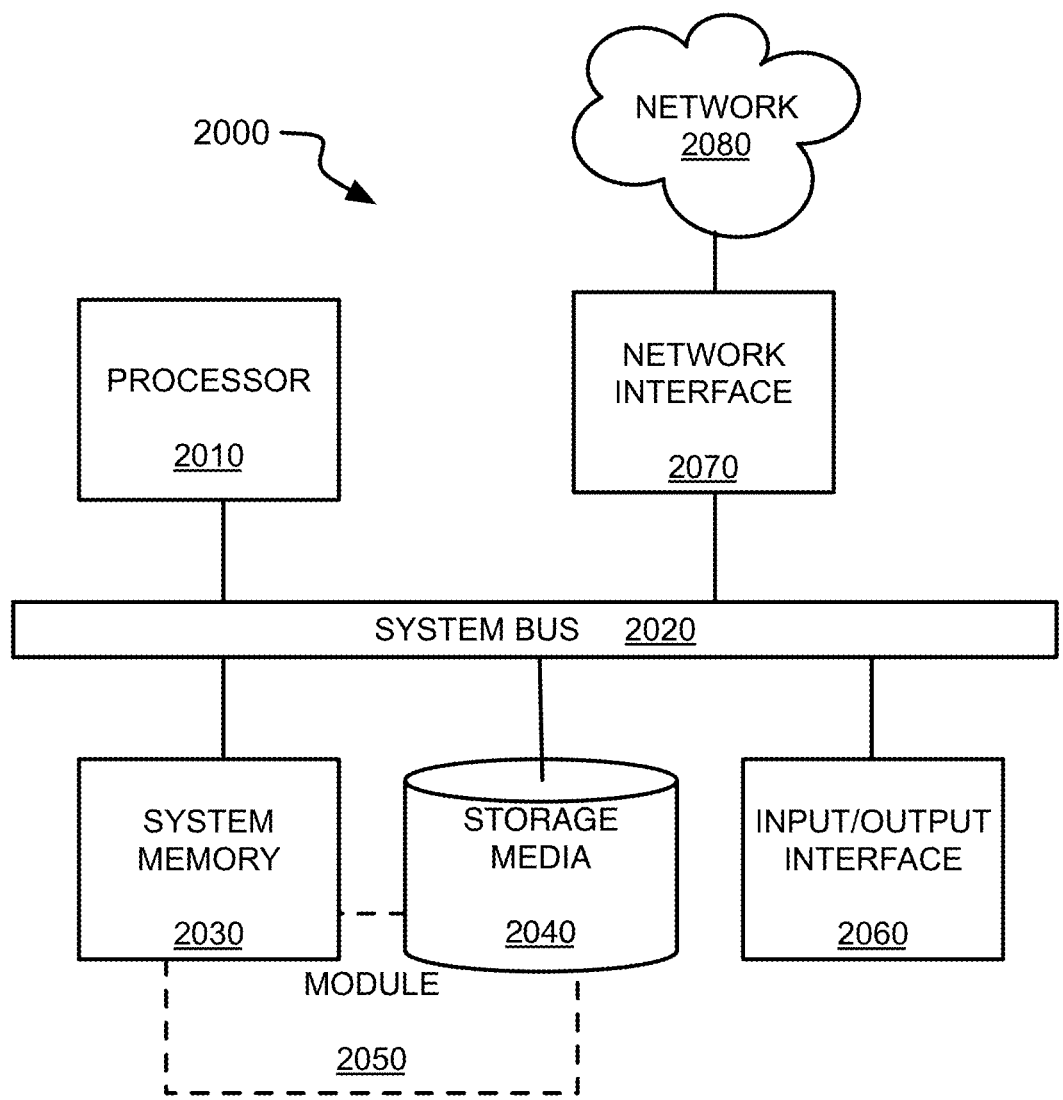
FIG. 7 is a block diagram depicting a computing machine and a module, in accordance with certain example embodiments.

FIG. 7 depicts a computing machine 2000 and a module 2050 in accordance with certain example embodiments. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one or more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCP"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, biometric readers, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement an embodiment of the disclosed embodiments based on the appended flow charts and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described herein. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The present method advantageously provides a method to allele type any polymorphic gene using the sequencing data produced by massively parallel sequencing without the use of time consuming and expensive additional experimentation. The present invention advantageously provides the ability to transform the sequencing data into allele information when a sample has been exhausted and does not exist any longer. This advantage provides, for example, the ability to analyze neoantigens that will bind to a specific HLA allele in a sample derived from a subject without having to conduct additional experimentation on a sample. In one embodiment HLA type and neoantigen presence can be obtained from sequencing data in a single sequencing run. The present invention also provides an improved method to detect mutations within polymorphic loci.

The present invention will be further illustrated in the following Examples which are given for illustration purposes only and are not intended to limit the invention in any way.

EXAMPLES

Example 1

WES from cases of chronic lymphocytic leukemia. (CLL) patients has been previously reported (Landau et aL, Cell. 2013, 152(4):714-26). A subset of cases within this cohort with available experimental HLA typing information (HLA-A, HLA-C) were selected for further analysis, A set of 133 HapMap samples comprising 15 Caucasians, 42 Black, 4.1 Chinese and 35 Japanese individuals with known HLA types (Erlich et al, 2011; found on the World Wide Web at 1000genomes.org) was used as a validation set. For detection of somatic mutation of the HLA loci, the gene typing method described above was applied to data from 10 tumor types curated from the TCGA project including lung squamous, lung adenocarcinoma, bladder, head and neck, colon, rectum, uterine, glioblastoma, ovarian, and breast, Two additional data, sets: a melanoma data set (Hodis et al. Cell, 2012, 150(2):251-63) and a chronic lymphocytic leukemia set (Wang et. al, NEJM. 201 1. 365:2497-2506), was also analyzed for mutations in the HLA-A, HLA-B and HLA-C genes. For ease of reference, the example embodiment disclosed in this section is referred to hereafter as POLYSOLVER.

A reference library of known HLA alleles (6597 unique entries) based on the IMGT database ((v3.10; found on the World Wide Web at ebi.ac.uk/ipd/imgt hla/) was constructed. Missing exons for incompletely sequenced allele cDNAs were deduced by multiple sequence alignment of the missing allele with all available cDNA sequences. Missing introns were inferred by alignment of the cDNA sequence with the nearest full-length genomic sequence. The final library comprised full-length genomic sequences of 2129 HLA-A, 2796 HLA-B and 1672 HLA-C alleles.

To generate efficiency in alignment, all reads mapping within 1 Kb of the HLA genes from the processed bam files were extracted. A further extraction was performed using a secondary 38-mer HLA sequence library to 'fish' for any reads that perfectly matched at least one tag in either orientation. Reads selected by this process are subjected to several post-processing filters (see below) prior to inference of alleles. The choice of 38 mers for creation of HLA tag library was based on maximizing the specificity of the library for HLA genes while maintaining 100% sensitivity in the context of downstream read filtering.

To assess the specificity of tag libraries of different lengths derived from the polymorphic genes, a sequence set of 21,000 non-polymorphic genes was created and the fraction non-polymorphic genes that matched at least one tag from the library was recorded for different tag lengths. Specificity was defined as 1 minus this fraction, see the table 1.

TABLE 1

Specificity of tag libraries of different lengths

| length | # tags | # non poly genes | Specificity |
| --- | --- | --- | --- |
| 20 | 697364 | 17505 | 15.72% |
| 24 | 788407 | 17184 | 17.26% |
| 28 | 877670 | 16931 | 18.48% |
| 32 | 965304 | 16623 | 19.96% |
| 36 | 1051894 | 16212 | 21.94% |
| 38 | 1095054 | 15922 | 23.34% |
| 40 | 1138288 | 15550 | 25.13% |
| 44 | 1224676 | 14662 | 29.40% |
| 48 | 1310772 | 13309 | 35.92% |
| 50 | 1353714 | 12600 | 39.33% |
| 60 | 1568396 | 8749 | 57.87% |
| 70 | 1785652 | 6003 | 71.10% |

The downstream filtering worked under the hypothesis that any alignment that had more than one event (an event being any of the following: mismatch, insertion or deletion) was likely a mis-alignment and was discarded. Under this hypothesis, 100% sensitivity for picking up all HLA reads in the sequencing run would require that the maximum tag length used for extracting reads should not exceed half the read length which in this case was 76. A choice of 38 for the tag length library assured that all reads with no more than one mismatch or deletion event would be captured, while delivering a specificity of −23% as defined above.

HLA allele names comprise the name of the gene (i.e. A, B, C) suffixed by successive sets of digits that indicate increasing sequence-level and functional resolution. The first set specifies the serological activity of the allele (allele level resolution, ex. A*01 or A*02) while the second set of digits, in conjunction with the first set of digits, specifies the protein sequence (protein level resolution, ex. A*02:01). Alleles were resolved up to the protein level resolution. A two-step inference procedure was applied; detecting the most-likely allele first and then, given the first allele, determining the second most likely allele. Inference is based on a Bayesian calculation that takes into account: (i) the qualities of the bases comprising each aligned read; (ii) the observed insert sizes of reads aligned to the allele; (iii) the number of reads aligned to the allele; and (iv) the prior probability of each allele (FIG. 1b). Previous studies have suggested that knowledge of the ethnicity of the individual under consideration can increase the probability of correct typing since the population-level allele frequencies differ based on race. (Erlich et al. BMC genomics. 2001, 12, 42); Gonzalez-Galarza et al. Nucleic Acids Research. 2011 39, D913-919). These known population-level allele frequencies were harnessed and ethnicity-dependent prior probabilities were used. The posterior probability was calculated for each allele which aggregates evidence from both the likelihood computation and the prior probability. The allele with the highest posterior probability ('the winner') was inferred to be the correct first allele.

Figure 8:
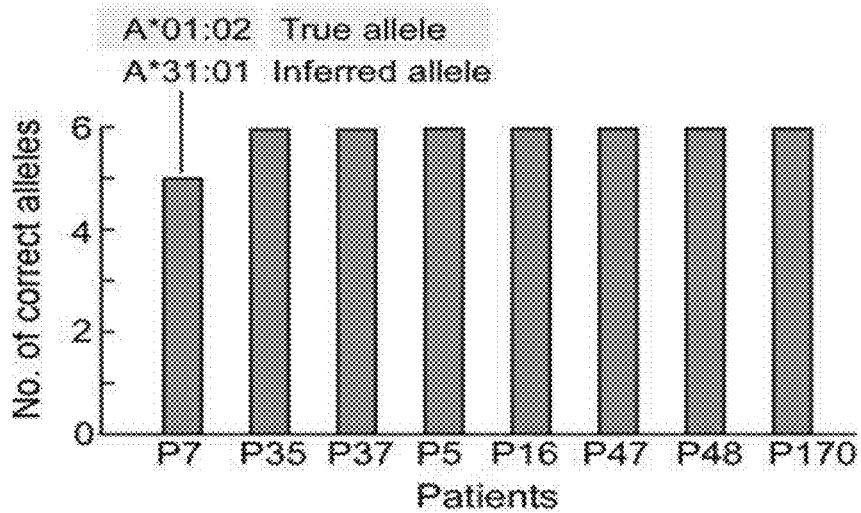
FIG. 8 is a graph showing the number of correctly inferred alleles using an example embodiment of the genotyping methods disclosed herein and applied to a training set of 8 CLL samples of known HLA type.

In the second step of the inference it was taken into account that: (i) an individual may be either homozygous or heterozygous for any of the HLA genes; and (ii) alleles encoding for the same protein sequence tend to have highly similar DNA sequences, thereby artificially inflating the posterior probabilities of alleles that bear significant sequence similarity to the first inferred allele. It was observed that selecting the top two alleles when the posterior probabilities were simply sorted in order was incorrectly biased in favor of declaring homozygous winners, with 23 out of 24 HLA loci in the training set being miscalled in this fashion. On the other hand, a complete depletion of reads mapping to the first inferred allele followed by a recalculation of the posterior probability-derived scores yielded only heterozygous calls. To balance between the two extremes, a strategy that shrank allele scores in proportion to their sequence similarity with the first inferred allele was devised as disclosed herein. The allele with the highest recalculated score was then inferred as the second true allele. By using this strategy, 47 of 48 (97.9%) alleles were correctly identified at the protein level. See FIG. 8.

Example 2

Validation of Genotyping Method

Figure 9:
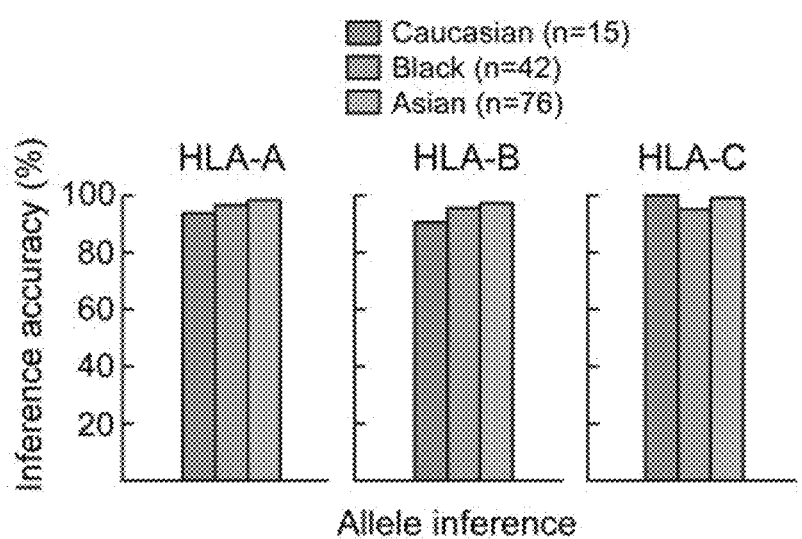
FIG. 9 is a graph showing the percent accuracy of an example embodiment of the genotyping methods disclosed herein in determining the HLA genotype of 133 HapMap samples.
Figure 10:
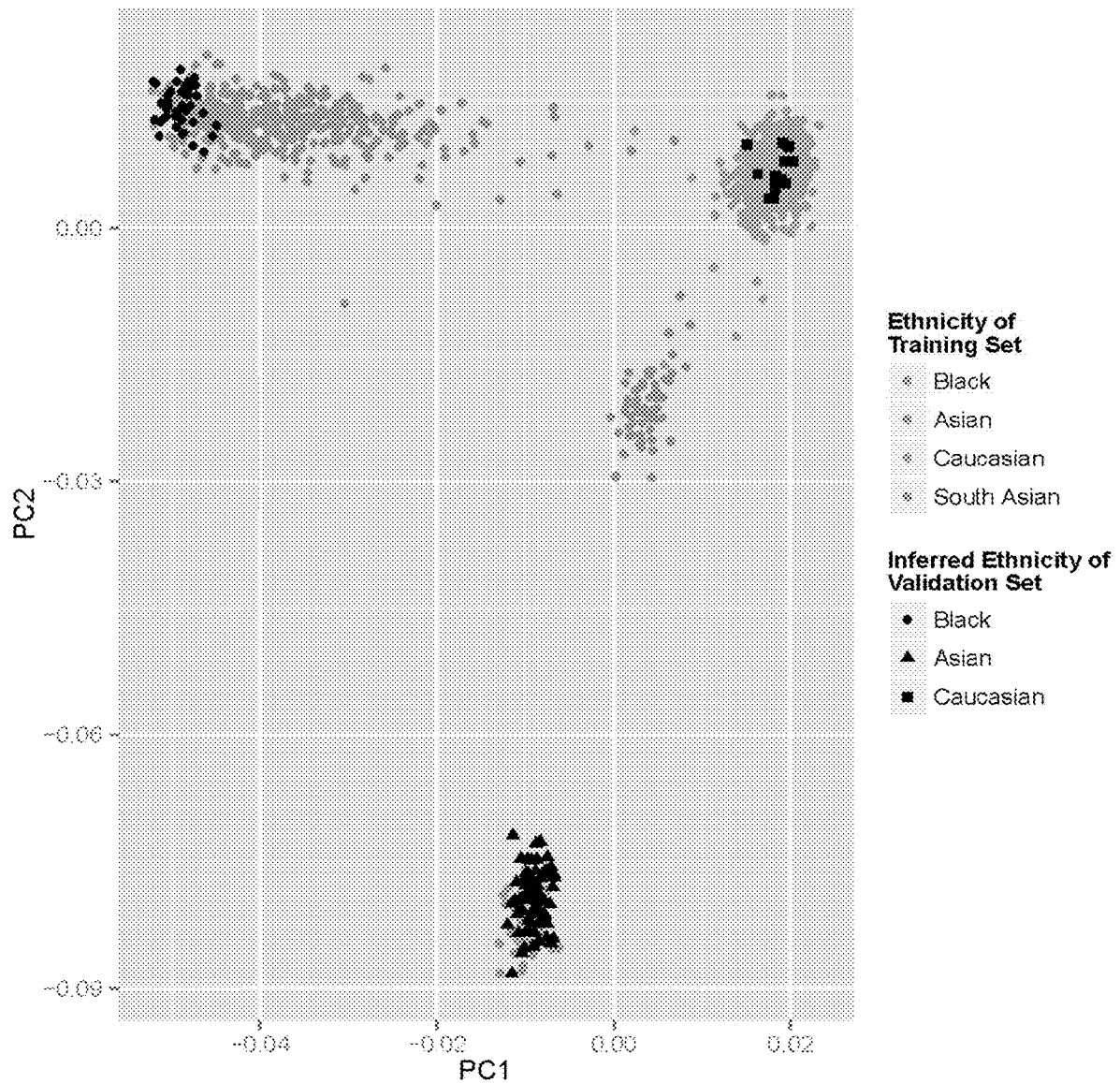
FIG. 10 is a plot showing the ethnicities of 133 HapMap samples correctly inferred based on their projection in the 2-dimensional space defined by two principal components. The colored icons show the clustering of the 1,398 training samples belonging to four different ethnic groups. The black icons depict the projection of 132 HapMap samples in this space (one sample was removed as an outlier). The success rate for attributing the correct ethnicity to each sample was 100%.

The method disclosed herein was applied to WES data from a set of 133 HapMap samples with known HLA genotypes. 774 of 798 (97%) alleles from this validation set were correctly resolved at the protein level while allele groups were correctly typed in 787 of 798 (98.7%) instances All 42 homozygous alleles in this set were correctly identified, and no significant differences in performance were observed based on ethnicity or HLA gene (chi-squared test P-values 0.043 and 0.314 respectively, 95% Bonferroni corrected P-value threshold=0.025). See FIG. 9. However, when this method was applied to the HapMap samples without using population-level allele frequencies, only 89% accuracy was observed. To accommodate use of the method with samples of unknown ethnic origin, the following principal components (PC)-based method for exome-based ethnicity inference, which can be used prior to analysis by the genotyping method disclosed herein.

4-digit allele frequencies for different ethnicities were calculated by taking a sample-size weighted average of all relevant population studies in the Allele Frequency Net Database (found on the World Wide Web at allelefrequencies.net/). A rapid principal components analysis (PCA) based method was developed to infer ethnicity for samples of unknown racial origin (Kiezun et al, manuscript in preparation). Exome data for samples of known (self-described) ethnicity from the 1000 Genomes and HapMap projects (n=1,398, with 911 Caucasians, 375 Blacks, 54 Asians, and 58 South Asians) was genotyped at a predefined set of 5,845 loci chosen based on considerations related to known linkage disequilibrium between different loci, representation on population genotyping platforms and consistency between genome releases. A. PCA revealed distinct segregation of Caucasian, Black, Asian, and South Asian samples in the 2-dimensional space defined by the first two principal components. Any new sample of unknown ethnicity may be projected in this space and its Euclidean distance from the clusters centroids can be computed, Ethnicity is inferred based on the cluster of minimal distance from the sample projection.

As an alternative to applying the PC-based ethnicity inference module, it was also observed that restricting inference of alleles to those having at least a 0.05% frequency in each of Caucasian, Black and Asian populations also resulted in 96% protein-level accuracy. Consistent with this finding, re-review of the sole misidentified allele within the original training set of CLL cases revealed it to be A*01:02, whose minor allele frequency is <0.05% in Caucasians.

Example 3

Comparison to Other HLA Typing Methods

Figure 11:
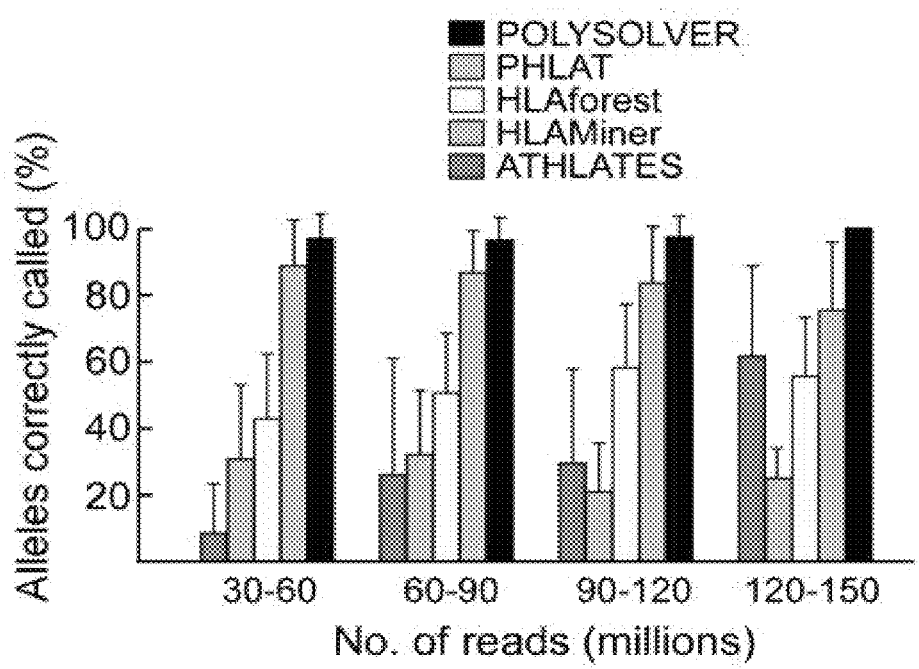
FIG. 11 is graph showing the overall accuracy of an example embodiment of the genotyping methods disclosed herein in determining the HLA genotype of 133 HapMap samples as compared to other known genotyping methods.

Using the 133 HapMap samples, the HLA typing method disclosed herein was compared to four recently reported algorithms for HLA typing. Overall accuracy, i.e. the percentage of alleles that were correctly called, for comparing the different approaches was used. Ambiguous calls or failure to make a call were both assessed as mistakes. ATHLATES (Liu et al. Nucleic Acid Research. 2013 41, e142) had an overall accuracy of 17% although its performance improved with increasing number of reads (which is a proxy for the average sequence coverage). HLAminer (Warren et al. Genomic Medicine. 2012, 4, 95) and HLAforest (Kim et al. PloS One. 2013, 8, e67885) 30% and 47% overall accuracies respectively, while PHLAT (Bai et al. BMC Genomics. 2014, 15) was able to correctly identify 87% of the 798 alleles. POLYSOLVER had an overall accuracy of 97% and >96% accuracy across the range of sequencing depths. See FIG. 11.

Example 4

Detection of Somatic Mutations within the HLA Region

The standard approach for detection of somatic mutations is to first align both tumor and normal reads to a reference genome and then scan the genome and identify mutational events observed in the tumor but not in the matched normal. An example of this approach is disclosed in Cibukskis et al. Nature Biotechnology. 2013, 31, 213-219. The genotyping method disclosed above was used to significantly improve alignment of reads (in both tumor and normal) and hence improve the sensitivity and specificity of somatic mutation calling within the HLA region. An overview of the method is diagrammed in FIG. 2. In this setting, the two inferred alleles for each HLA gene would serve as patient-specific reference 'chromosomes' against which pre-selected HLA reads from the tumor and germline samples are aligned separately followed by standard mutation calling. An analysis pipeline to call somatic mutations in the HLA genes was built that includes the following steps: (i) ethnicity detection using the normal sample; (ii) HLA typing by applying HLA typing method disclosed herein on the normal sample; (iii) re-alignment of the HLA reads in both tumor and normal to the inferred HLA-alleles while filtering out likely erroneous alignments; (iv) applying a mutation detection tool, such as MuTect (Cibukskis et al. and Saunders et al. Bioinformatics. 2012 28, 1811-1817) to detect somatic mutations by comparing the re-aligned tumor and normal HLA reads.

Regarding step (iii), prior to detection of somatic changes using the mutation detection method by comparison of tumor and normal HLA read aligned to the inferred patient-specific HLA alleles, the following changes and filters were implemented: (i) NotPrimaryAlignment bit flag was turned off from all alignments since several reads mapped to multiple alleles; (ii) mapping quality was changed to a non-zero value (=70) for all reads; (iii) alignments where both mates did not align to the same reference allele were discarded; and (iv) alignments where at least one mate had more than one mutation, insertion or deletion event compared to the reference allele were discarded. Soft-clipping of the reads was not allowed during the alignment. Alleles with multiple detected somatic changes were removed from the analysis. In cases where both inferred alleles are identical in the region of detected somatic mutation, the mutation was assigned to the more common allele in the population. All somatic events were visualized using IGV (Mutect: 'KEEP' entries in call_stats file, Strelka: All entries in all.somatic.indels.vcf file) and the ones that passed manual review were further annotated for the gene compartment (intron, exon, splice site) and protein change. Splice sites were defined as the set of splice consensus sequence positions that had a bit score of at least 1 in either the human major/U2 or human minor/U12 introns at the exon/intron boundaries (9 positions at the 5' splice donor end of the intron including the ultimate base in the upstream exon, and 2 positions at the 3' splice acceptor end of the intron. (Irimia et al. Cold Spring Harbor perspectives in biology 6 (2014).

Figure 12:
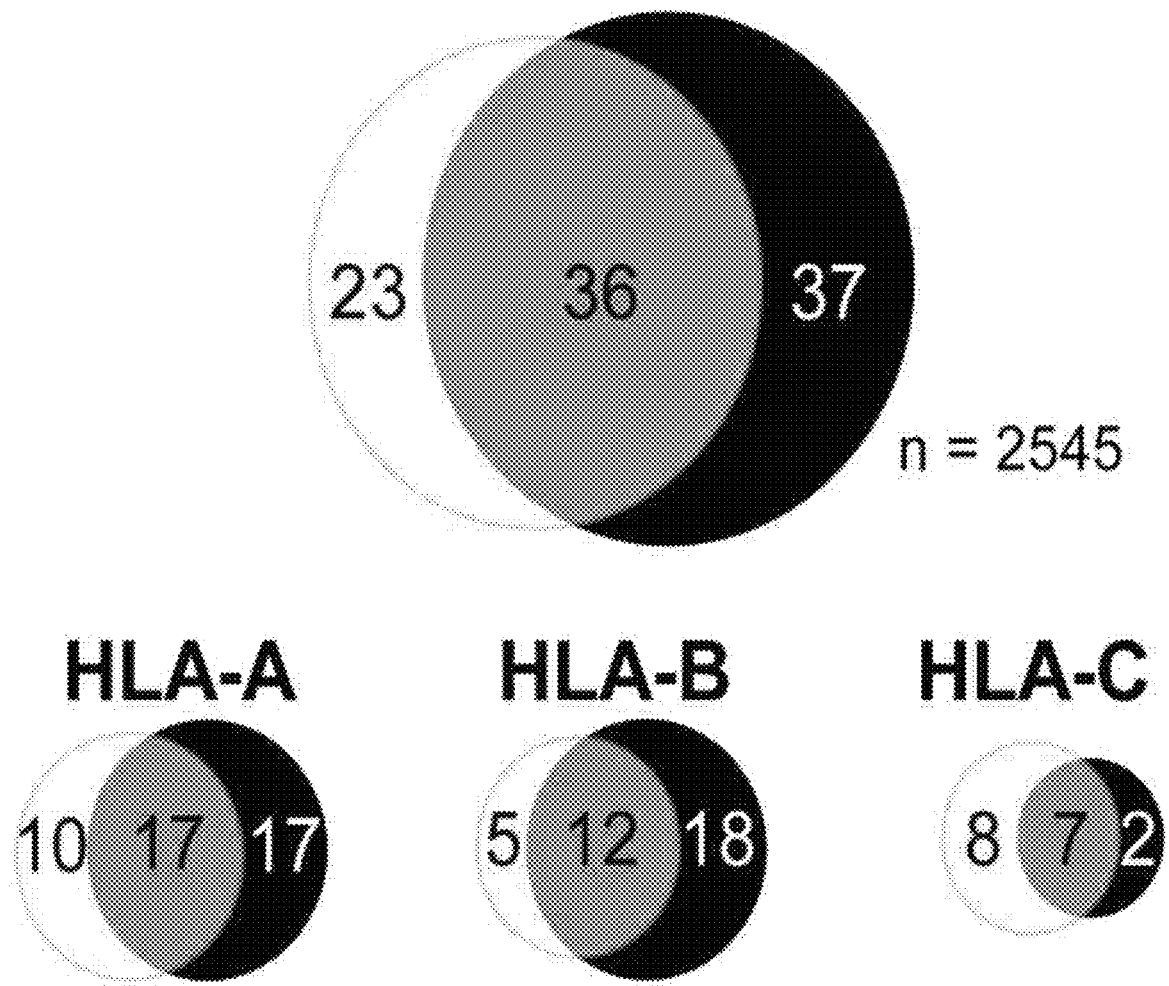
FIG. 12 is a diagram providing a comparison of somatic HLA mutations identified across cancers using standard approaches (TCGA) and an example embodiment of the mutation detection methods disclosed herein (POLYSOLVER).
Figure 13:
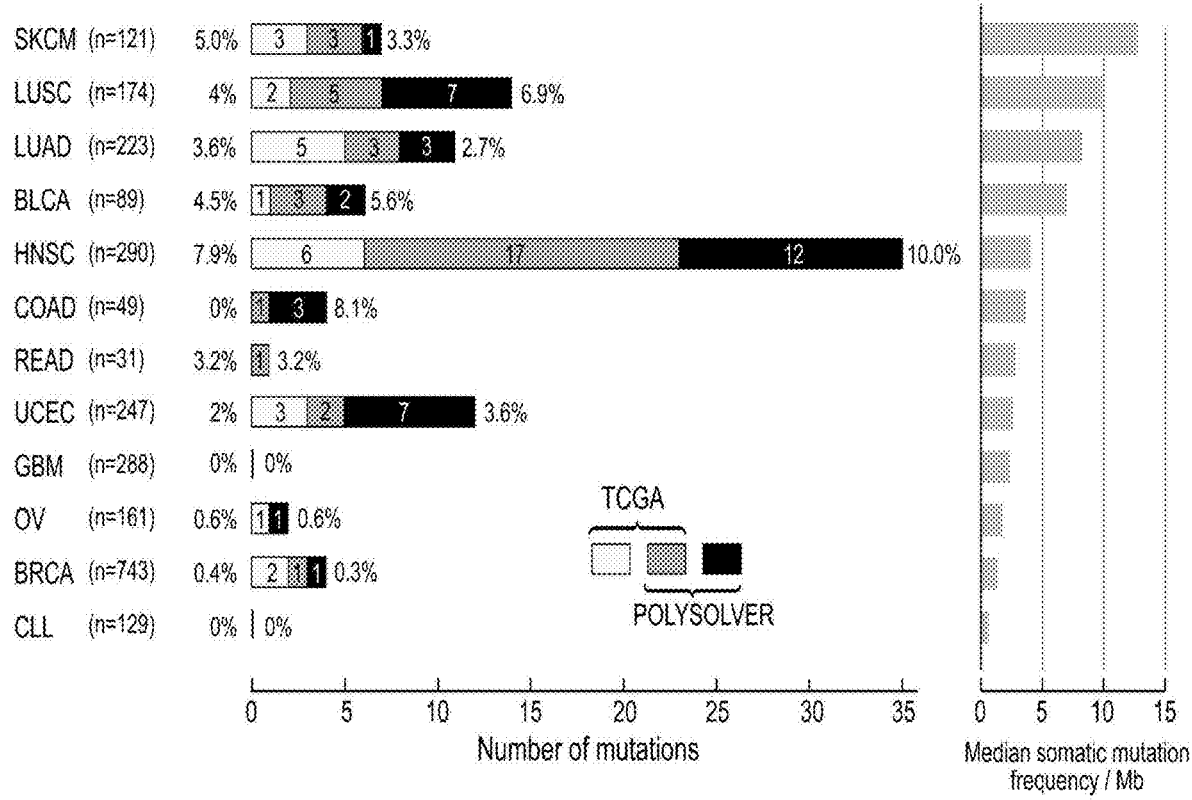
FIG. 13 is a graph showing the number of HLA mutations and the percentage of sample bearing HLA mutations per cancer type identified using standard methods (TGCA) and an example embodiment of the mutation detections methods disclosed herein (POLYSOLVER). (SKCM=melanoma, LUSC=lung squamous cell carcinoma, LUAD=lung adenocarcinoma, BLCA=bladder, HNSC=head and neck, COAD=colon adenocarcinoma, READ=rectum adenocarcinoma, UCEC=uterine, GBM=glioblastoma multiforme, OV=ovarian, BRCA=breast, CLL=chronic lymphocyte leukemia.

To test this approach, a dataset of 2,545 cases of matched tumor and germline DNA spanning 12 tumor types was assembled –10 from the The Cancer Genome Atlas project (TCGA), and two separate genomic studies focusing on chronic leukocytic leukemia and melanoma. 59 HLA gene (including HLA-A, B and C) somatic mutations were previously detected using standard methods and reported as part of a pan-cancer analysis effort (Omberg et al., Nature genetics. 2013 45, 1121-1126; Wang et al., The New England Journal of Medicine. 2011, 365:2497-2506; Hodis et al., Cell. 2012, 150:251-263). On re-analysis of these cases with mutation detection pipeline disclosed herein, 36 of the 59 (61%) previously reported HLA mutations were detected, as well as 37 novel HLA somatic mutations; in total, 73 mutations in 64 of the 2,545 cases. See FIGS. 12 and 13. Manual review of all HLA mutation events using IGV (Robinson et al., Nature biotechnology. 2011, 29:24-26), suggested that 9 of the 23 mutations identified exclusively by TCGA were true events, of which 6 were just below the detection limit of the initial pipeline and were identified once the read filtering criteria used prior to mutation calling were slightly relaxed.

Figure 14:
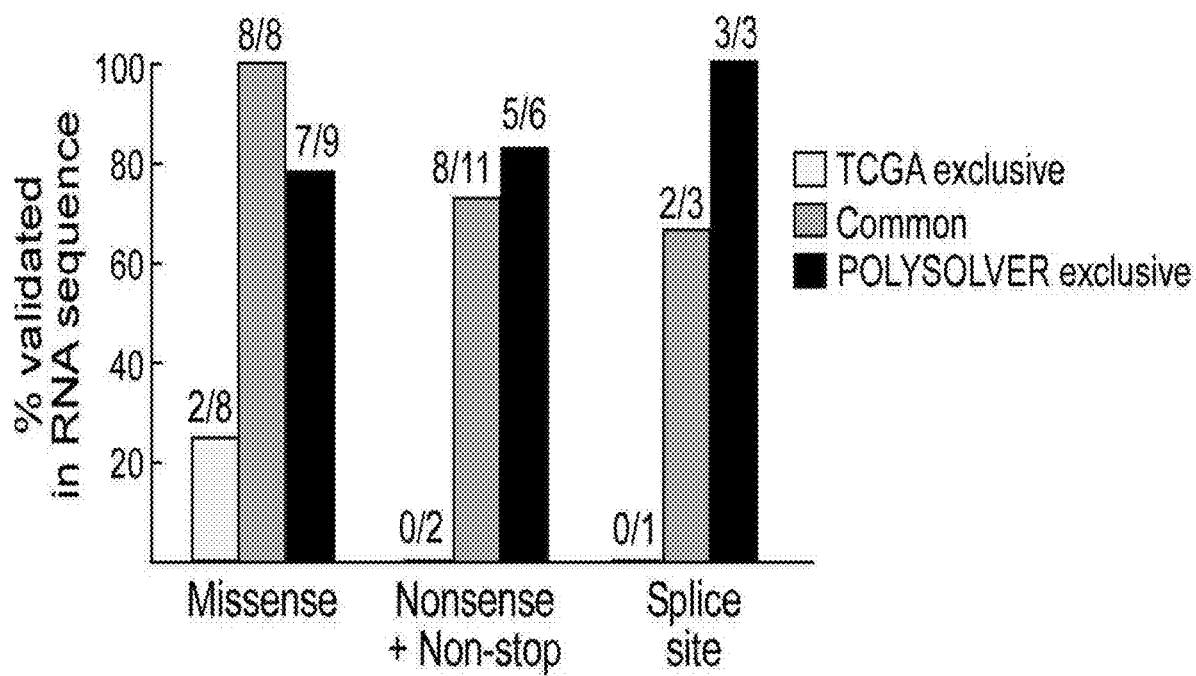
FIG. 14 is a graph showing validation of mutations at the transcriptome level using standard methods (TCGA) and an example embodiment of the mutation detection methods disclosed herein (POLYSOLVER).

When available, matching RNA-Sequencing data was examined for orthogonal evidence of expression of the somatically mutated HLA allele that was detected by WES (indel calls were excluded from this analysis due to low reliability of indel alignment and detection by RNA-Seq). In total, RNA-Seq data for 51 of 96 mutations was evaluated, including 11 that were exclusively reported by TCGA, 18 detected only by the methods disclosed herein and 22 that were detected by both. A high rate of RNA-Seq based validation of missense, nonsense and splice-site mutations in the 22 common set was observed (8 of 8; 8 of 11; and 2 of 3 events, respectively. FIG. 14. Similar high rates of validation for events identified exclusively by mutation detection methods disclosed herein were likewise observed. (7 of 9; 5 of 6; and 3 of 3 events respectively). By contrast, only 2 of the 11 mutations uniquely identified by TCGA were validated using RNA-Seq. These results support that the mutation detection methods disclosed herein provide both sensitive and specific somatic mutation detection within the highly polymorphic HLA loci.

Example 5

Patterns of Somatic HLA Mutation Across Tumor Types

The mutation detection method disclosed herein was extended to a total of 3,608 TCGA tumor/normal pairs (including the original collection of 2,545 and 1,063 additional cases). In total, 147 somatic HLA mutations in 121 of the 3,608 (3.3%) individuals were detected.

Consistent with the expected loss-of-function consequence, the somatic HLA mutations were distributed across the entire gene. See FIG. 15. Interestingly, differences amongst the cancer types in frequency, localization and types of somatic HLA mutations were observed. HLA mutations in HNSC (HLA-A, HLA-B) and LUSC (HLA-A) have previously been found to be significant by MutSig (Mutation Significance) analysis. (Lawrence et al. Nature. 2014 505, 495-501). Using the mutation detection methods disclosed herein, HLA-A (FDR q=2.3×10$^{-08}$) and HLA-B (FDR q=3.9×10$^{-07}$) were identified to be significantly mutated in colon adenocarcinoma. On the other hand, CLL (n=129) and OV (n=300) entirely lacked HLA mutations, and only a single mutation was detected in GBM (n=320).

It was also observed that 70 of the 147 total HLA mutations (47.6%) fell in 23 recurrent positions (amino acids that were mutated at least twice). The recurrent sites were distributed across the HLA gene (median of 2 mutated cases/recurrent site (range 2-10). See bottom of FIG. 15.

Example 6

Figure 15:
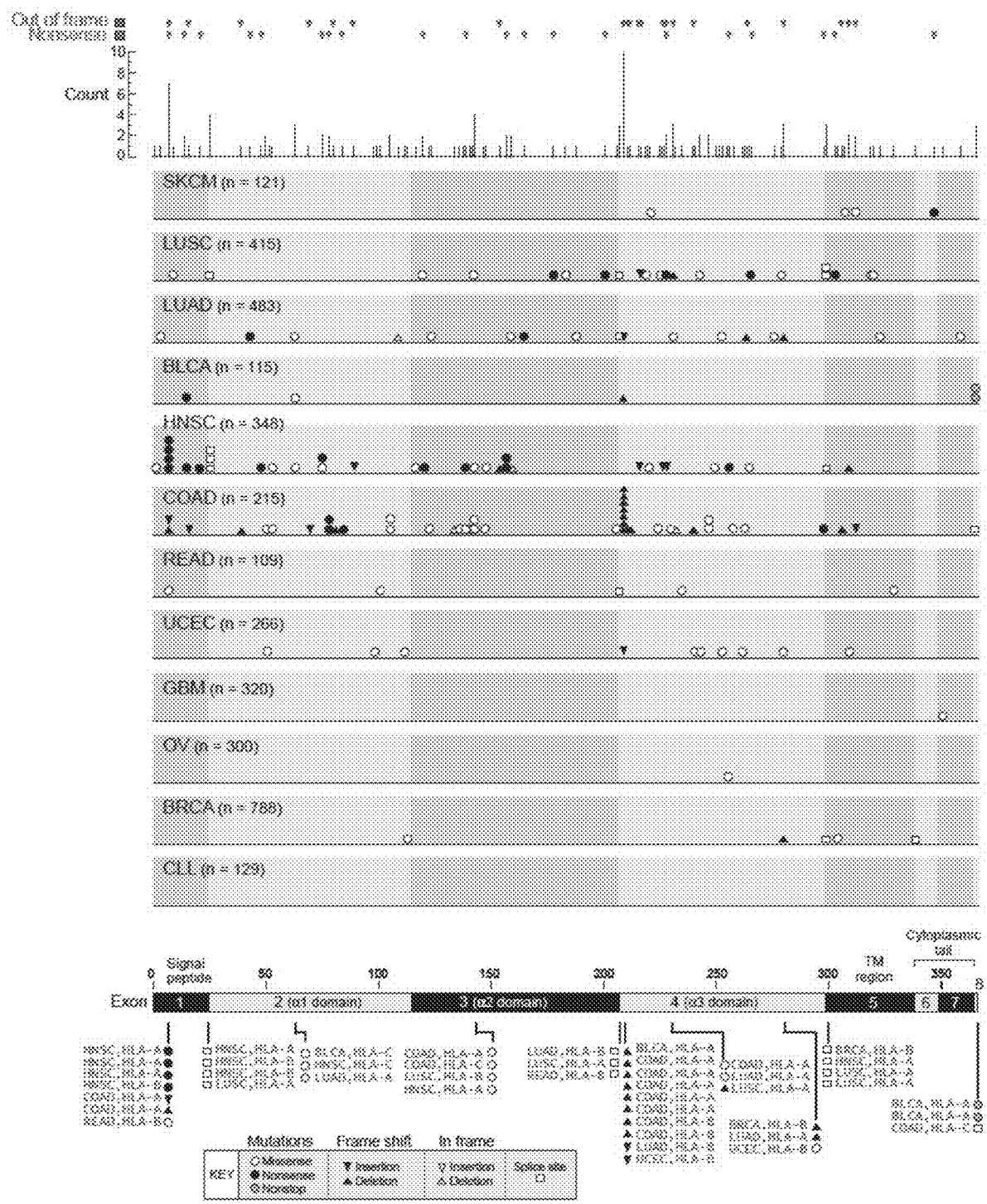
FIG. 15 is graph showing the distribution of HLA mutations across functional domains and tumor types detected using a mutation detection method in accordance with an example embodiment. Top—Distribution of potential loss-of-function events; out of frame (blue) and nonsense mutations (red). The histogram summarizes the number of events identified at each position. Central Panel—Pattern of mutations detected in each tumor type. Bottom—Recurrent events; recurrent positions (with disease, allele group) with frequence≥3 cases/recurrent site are shown.
Figure 16:
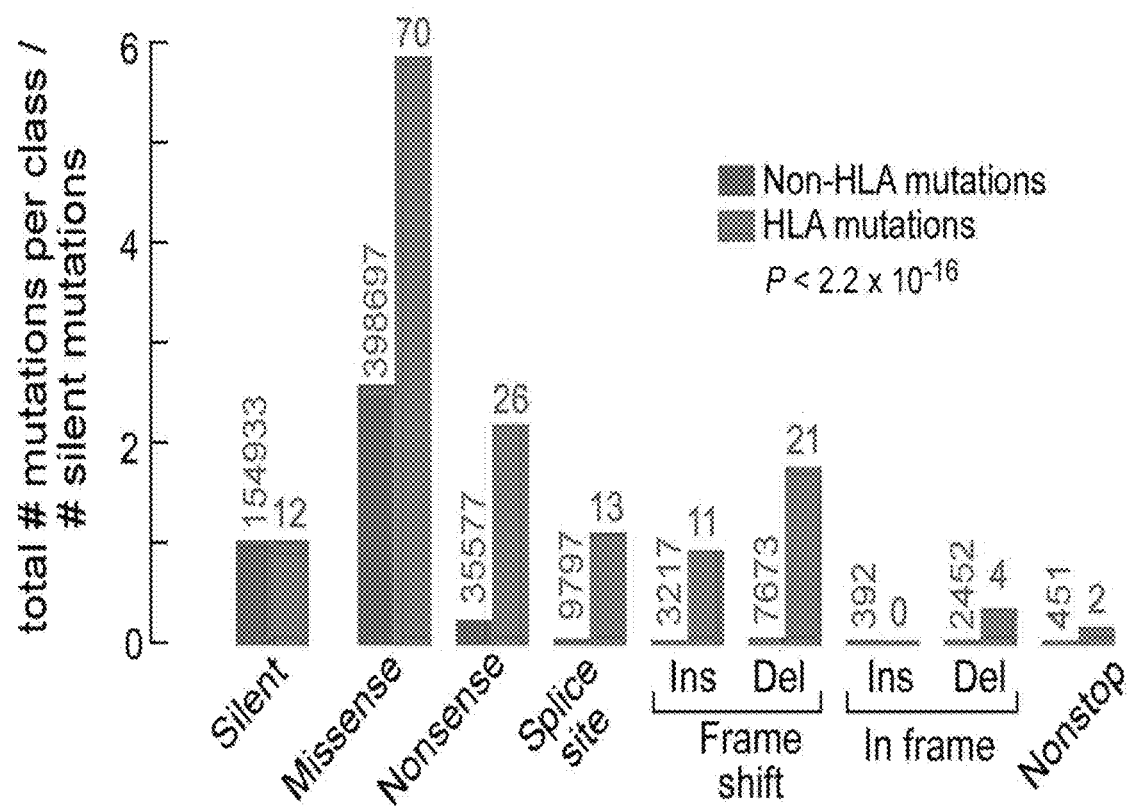
FIG. 16 is a graph showing a comparison of spectrum of mutations in non-HLA genes and HLA genes. The ratio of number of mutations to a particular type to the number of silent mutations is compared between the non-HLA and HLA genes for all mutation types (chi-square test, $P<2.2\times 10^{-16}$).

Somatic Class I HLA Mutations are Enriched for Localization at Sites Affecting Peptide-MHC Interactions Alterations highly likely to have a functional effect, including loss-of-function events (nonsense or frameshift mutations), were significantly enriched in HLA mutations compared to non-HLA mutations (FIG. 16, chi-squared test P<2.2×10$^{16}$) and were distributed throughout the gene (FIG. 15).

The highest frequency of mutations occurred in exon 4 (54 mutations, 36.7%) which encodes the α3 domain of the HLA protein that binds to the CD8 co-receptor of T cells. (Fayen et al. Molecular Immunology, 1995 32, 267-275 (1995), See FIG. 17. Abrogation of this function could lead to a loss of T cell recognition and thereby a loss of immune reactivity. The second highest frequency of mutations occurred in exon 3 (31 mutations, 21%) followed by exon 2 (25 mutations, 17%), which encode the α1 and α2 peptide binding domains of the HLA molecule respectively which conventionally bind 9- and 10-mer peptides for antigen presentation. (Brusic et al. Immunol Cell Biol 80, 280-285 (2002).

Figure 18:
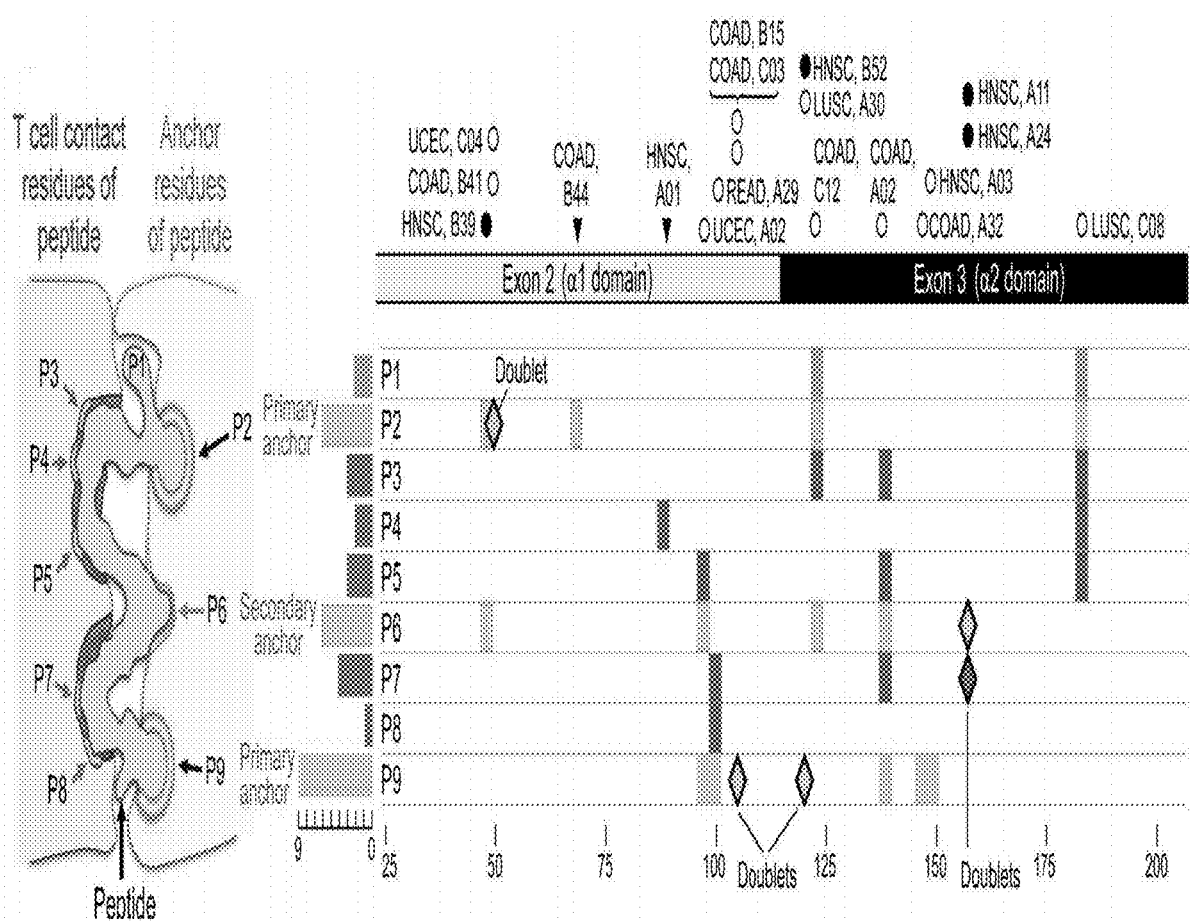
FIG. 18 is a diagram and graph mapping detected mutations in HLA positions that are in actual physical contact with the peptide (contact residues). Left panel—The relative orientation of a 9-mer peptide with respect to the HLA and T cell molecules. Positions 2 and 9 constitute the primary anchors while position 6 forms the secondary anchor with HLA. The remaining positions interact with the T cell molecule. Right Panel—The 9 amino acids of the peptide and their corresponding HLA contact residues are indicated along the rows (orange—HLA interacting anchor positions, blue—T cell interacting positions). The histogram depicts the frequency of observed HLA mutations in contact residues corresponding to each peptide position.

Analysis of the position of the mutated residues within exons 2 and 3 in relationship to their predicted interaction with binding peptide further strongly suggest alteration of immune function by these somatic HLA mutations. The two major anchor grooves in the HLA molecule bind to positions 2 and 9 respectively of the peptide and mutation in either groove would be expected to profoundly effect on the biochemical stability of the MHC-peptide complex (Brusic et al.). A secondary anchor groove that interacts primarily with the sixth amino acid of the peptide lies between the two primary anchor grooves. (Ruppert et al. Cell 74, 929-937 (1993). Overall, 32% of mutations (18 of 56) in the peptide binding domains were in residues that come in contact with the peptide and 83% (15 of 18) of these were in positions that comprised one of the two primary anchor grooves. See FIG. 18.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating cancer, comprising:
(i) identifying a polymorphic gene type that encodes a human leukocyte antigen (HLA) protein predicted to bind to a neo-epitope performing a computer-implemented method for genotyping polymorphic genes of a patient to identify the polymorphic gene type, the computer-implemented method comprising:
   (a) inputting sequence reads extracted from a target polymorphic gene of the patient into a non-transitory computer-executable storage device having a computer-readable and computer-executable program for gene typing and alignment analysis;
   (b) generating alignments of the sequence reads extracted from the target polymorphic gene of the patient to a gene reference sequence set having a plurality of gene reference sequences, each gene reference sequence in the gene reference sequence set corresponding to an allele variant of the target polymorphic gene;
   (c) determining a first posterior probability or first posterior probability derived score for each allele variant in the alignments based on the sequence reads aligned to each allele variant;
   (d) determining a second posterior probability or posterior probability derived score for each allele variant in the gene reference sequence set, wherein a weighting factor is applied to a score contribution of each aligned sequence read based on whether or not the sequence read was also aligned to a first allele variant with a maximum first posterior probability or posterior probability derived score, wherein the weighting factor is based on the corresponding first posterior probability or posterior probability derived score for each of one or more overlapping sequence reads that aligned with the first allele variant and also aligned with one or more other allele variants in the alignments; wherein the first allele variant and a second allele variant with a maximum second posterior probability or posterior probability derived score indicate the polymorphic gene type, and wherein the weighting factor for a given read mapping to the identified first allele variant and the other allele variant is equal to the contribution of the sequence read to an overall posterior probability or posterior probability derived score of other allele variant (s1) divided by a sum of that contribution and a contribution of the sequence read to an overall posterior probability or posterior probability derived score of the first allele variant (s2), wherein the weighting factor w=s1/(s1+s2), and a new contribution of the sequence read to the overall posterior probability or posterior probability derived score of the other allele variant=w*s1, and
   wherein the first and the second posterior probability or posterior probability derived scores are determined based on base quality scores and an insert size probability value for each sequence read in the alignment, and wherein the insert size probability value is based at least in part on an insert size distribution of all of the sequence reads extracted from the target polymorphic gene of the patient, or
   wherein the first and second posterior probabilities or posterior probability derived scores are calculated based at least in part on population-based allele probabilities observed in a known population data set;

(ii) predicting a human leukocyte antigen (HLA) encoded by the polymorphic gene type identified in (i) above that binds to the neo-epitope;
(iii) preparing a personalized treatment composition, wherein the personalized treatment composition comprises:
   (a) neo-epitopes predicted to bind to a protein encoded by the polymorphic gene type identified in (i) above;
   (b) a polynucleotide encoding neo-epitopes predicted to bind to the HLA protein predicted in (ii) above and encoded by the polymorphic gene type identified in (i) above;
   (c) antigen presenting cells (APCs) comprising neo-epitopes predicted to bind to the HLA protein encoded by a polymorphic gene type indicated in (ii) above or a polynucleotide encoding neo-epitopes predicted to bind to the HLA protein predicted in (ii) above and encoded by a polymorphic gene type identified in (i) above; or
   (d) T cells stimulated with APCs comprising neo-epitopes predicted to bind to the HLA protein predicted in (ii) above and encoded by the polymorphic gene type identified in (i) above or a polynucleotide encoding neo-epitopes predicted to bind to a protein encoded by a polymorphic gene type identified in (i) above, and
(iv) administering an effective amount of the personalized treatment composition to the patient, wherein the neo-epitopes and the identified polymorphic gene type are both present in the patient.

2. The method of claim 1, wherein the sequence reads extracted from the target polymorphic gene consist of reads that map to the target polymorphic gene within a threshold base number value, wherein the threshold base number value is between approximately 0.5 Kb bases and approximately 5 Kb bases, or where the threshold base number value is 1 Kb.

3. The method of claim 1, wherein the sequence reads extracted from the target polymorphic gene consist of sequence reads that match one or more probes from a polymorphic gene probe set, wherein the sequence reads match the one or more probes in a 5' to 3' or 3' to 5' orientation, and wherein the one or more probes are derived from a library of known or inferred genomic and/or cDNA sequences for the polymorphic gene, or
   wherein the sequence reads have between approximately 90% sequence identity and approximately 100% sequence identity to one or more probes in the polymorphic gene probe set, or
   wherein the sequence reads have approximately 100% sequence identity to one or more probes in the polymorphic gene probe set, or
   wherein the one or more probes in the polymorphic gene probe set have a size between approximately 25 mer and approximately 100 mer, or
   wherein the one or more probes in the polymorphic gene probe set have a size of 38 mer, or
   wherein the length of one or more probes in the polymorphic gene probe set is less than or equal to half the length of each sequence read.

4. The method of claim 1, wherein the sequence reads extracted from the target polymorphic gene are obtained by whole exome sequencing or whole genome sequencing of a biological sample of the subject.

* * * * *